United States Patent [19]

Komazawa et al.

[11] Patent Number: 5,106,871
[45] Date of Patent: Apr. 21, 1992

[54] ANTI-ULCER AGENT COMPRISING CHALCONE DERIVATIVE AS EFFECTIVE INGREDIENT AND NOVEL CHALCONE DERIVATIVE

[75] Inventors: Yukio Komazawa; Shigefumi Takeda; Kunio Hosaka; Hiroshi Mitsuhashi; Toshihiko Watanabe, all of Tokyo, Japan

[73] Assignee: Tsumura & Co., Tokyo, Japan

[21] Appl. No.: 733,003

[22] PCT Filed: Dec. 12, 1987

[86] PCT No.: PCT/JP87/00973

§ 371 Date: Jul. 20, 1988

§ 102(e) Date: Jul. 20, 1988

[87] PCT Pub. No.: WO88/04288

PCT Pub. Date: Jun. 16, 1988

Related U.S. Application Data

[63] Continuation of Ser. No. 436,088, Nov. 9, 1989, abandoned, which is a continuation of Ser. No. 237,850, Jul. 20, 1988, abandoned.

[30] Foreign Application Priority Data

Dec. 12, 1986 [JP] Japan .................. 61-294952
Aug. 10, 1987 [JP] Japan .................. 62-198197

[51] Int. Cl.$^5$ .................................................. A61K 31/19
[52] U.S. Cl. ................................. 514/571; 514/685; 562/464; 568/334; 568/325
[58] Field of Search .............. 514/571, 685; 562/464; 568/334, 325

[56] References Cited

U.S. PATENT DOCUMENTS

| 3,137,621 | 6/1964 | Lafon ...................... | 568/334 |
| 3,598,840 | 8/1971 | Majoie ..................... | 568/334 |
| 3,686,319 | 8/1972 | Lafon ...................... | 568/334 |
| 3,743,716 | 7/1973 | Rizyi et al. ............... | 568/334 |
| 4,279,930 | 7/1981 | Hall et al. ................ | 568/334 |
| 4,605,674 | 8/1986 | Fujiu et al. ............... | 568/334 |

FOREIGN PATENT DOCUMENTS

| 0013960 | 8/1980 | European Pat. Off. ........ | 568/334 |
| 48-08485 | 2/1973 | Japan . | |
| 50-24257 | 3/1975 | Japan . | |
| 50-70346 | 6/1975 | Japan .................. | 568/334 |
| 50-101342 | 8/1975 | Japan .................. | 568/334 |
| 50-101343 | 8/1975 | Japan .................. | 568/334 |
| 75-140429 | 12/1976 | Japan . | |
| 54-19947 | 2/1979 | Japan . | |
| 55-62044 | 5/1980 | Japan . | |
| 56-7736 | 1/1981 | Japan .................. | 568/334 |
| 1445779 | 8/1976 | United Kingdom ........ | 568/334 |

OTHER PUBLICATIONS

Chem. Pharm. Bull. 18, pp. 602–607 (1970).
Agr. Biol. Chem. 39, pp. 667–672 (1975).
Chem. Pharm. Bull. 27, pp. 2943–2953 (1979).
Kyogoku, et al., "Isoprenylchalcones", *Chemical Abstracts*, vol. 85, No. 1, Abstract No. 5913q (Jul. 5, 1976), p. 478.
Miyazaki, "Antiulcer Agents in Licorice", *Chemical Abstracts*, vol. 80, No. 8, Abstract No. 41034j (Feb. 25, 1974), p. 269.
Kyogoku, et al., "Isoprenylchalcones", *Chemical Abstracts*, vol. 83, No. 21, Abstract No. 178567s (Nov. 24, 1975), p. 528.
"Dihydrochalcone Derivative", *Patent Abstracts of Japan*, vol. 4, No. 98 (1980), p. 580.
Kyogoku, et al., "Anti-Ulcer Effect of Isoprenyl Flavonoids. II.[1] Synthesis and Anti-Ulcer Activity of New Chalcones Related to Sophoradin", *Chem. Pharm. Bull.*, vol. 27, No. 12 (1979), pp. 2943–2953.
Hatayama, et al., "Anti-Ulcer Effect of Isoprenyl Flavonoids. III.[1] Synthesis and Anti-Ulcer Activity of Metabolites of 2′—Carboxymethoxy—4,4′—bis (3—methyl—2—butenyloxy)chalcone[2])", *Chemical & Pharmaceutical Bulletin*, vol. 33, No. 4 (Apr. 1985).
"Chalcone Derivatives", *Patent Abstracts of Japan*, vol. 3, No. 46 (Apr. 18, 1979), p. 19.

*Primary Examiner*—James H. Reamer
*Attorney, Agent, or Firm*—Burns, Doane, Swecker & Mathis

[57] ABSTRACT

The present invention relates to an anti-ulcer agent comprising a compound represented by the following general formula I as the effective ingredient, and a novel chalcone derivative included in the compound represented by this general formula I:

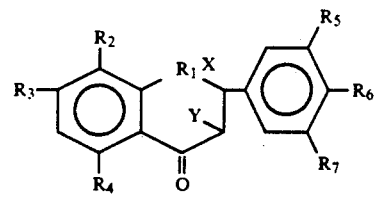

wherein X and Y independently stand for a hydrogen atom or together form a single bond, $R_1$ stands for a hydroxyl group, an acetoxy group, a carboxymethoxy group or a methoxycarbonylmethoxy group, $R_2$ stands for a hydrogen atom, an isoprenyl group, isopentyl group or a propyl group, $R_3$ stands for hydroxyl group or a methoxy group, $R_4$ stands for a hydrogen atom, a hydroxyl group or a methoxy group, $R_5$ stands for a hydrogen atom, a hydroxyl group, a methoxy group or an isopentyl group, $R_6$ stands for a hydroxyl group, a methoxy group or a carboxymethoxy group, and $R_7$ stands for a hydrogen atom or a methoxy group.

6 Claims, No Drawings

ANTI-ULCER AGENT COMPRISING CHALCONE DERIVATIVE AS EFFECTIVE INGREDIENT AND NOVEL CHALCONE DERIVATIVE

This application is a continuation of application Ser. No. 07/436,088, filed Nov. 9, 1989, which is a continuation of application Ser. No. 07/237,850, filed Jul. 20, 1988, now both abandoned.

TECHNICAL FIELD

The present invention relates to an anti-ulcer agent having, anti-ulcer action, which is effective for the medical treatment of diseases of digestive organs, such as a gastric ulcer and a duodenal ulcer, and a novel chalcone derivative having such an anti-ulcer action.

BACKGROUND ART $H_2$ receptor antagonists, anti-choline agents, gastric mucous membrane-protecting agents and antacids are now mainly used as anti-ulcer agent. Although these agents have medicinal effects, undesirable adverse side effects are also found. For example, the $H_2$ receptor antagonists most frequently used at the present are excellent in the action of controlling a secretion of gastric juice, but are defective in that, after discontinuation of the administration, a counteraction of promoting a secretion of gastic juice appears. Anti-choline agents often show an excessive action of controlling a secretion of gastric juice because they have a parasympatholytic action, and moreover, they blunt the activity of the stomach and impair digestion. Since antacids temporarily neutralize gastric acid, they show a counteraction of promoting a secretion of gastric juice and other various adverse side effects. In short, an agent having excellent anti-ulcer action and showing no adverse side effects has not been developed.

DISCLOSURE OF THE INVENTION

It is therefore a primary object of the present invention to provide an anti-ulcer agent having excellent anti-ulcer action and reduced adverse side effects, which can be continuously administered for a long time.

The present inventors carried out research with a view to attaining this object, and as a result, found that a chalcone derivative represented by the following general formula I (hereinafter referred to as "compound of formula I") has a remedial effects for ulcers and the present invention was completed based on this finding:

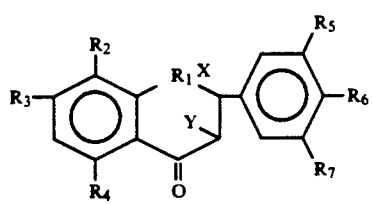

wherein X and Y independently stand for a hydrogen atom or together form a single bond, $R_1$ stands for a hydroxyl group, an acetoxy group, a carboxymethoxy group or a methoxycarbonylmethoxy group, $R_2$ stands for a hydrogen atom, an isoprenyl group, isopentyl group or a propyl group, $R_3$ stands for a hydroxyl group or a methoxy group, $R_4$ stands for a hydrogen atom, a hydroxyl group or a methoxy group, $R_5$ stands for a hydrogen atom, a hydroxyl group, a methoxy group or an isopentyl group, $R_6$ stands for a hydroxyl group, a methoxy group or a carboxymethoxy group, and $R_7$ stands for a hydrogen atom or a methoxy group.

More specifically, in accordance with the present invention, there is provided an anti-ulcer agent comprising a compound of formula I as the effective ingredient.

Of the compounds of formula I valuable for use as the anti-ulcer agent of the present invention, compounds represented by the following general formula I' are novel, and therefore, in accordance with the present invention, there is provided a novel chalcone derivative represented by the following general formula I':

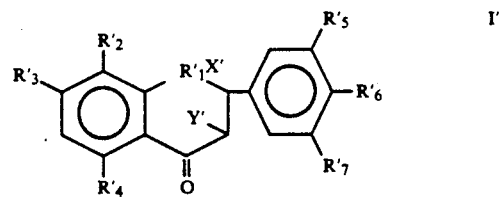

wherein X' and Y' independently stand for a hydrogen atom or together form a single bond, $R'_1$ stands for a hydroxyl group or a carboxymethoxy group, $R'_2$ stands for a hydrogen atom, an isoprenyl group, an isopentyl group or a propyl group, $R'_3$ stands for a hydroxyl group or a methoxy group, $R'_4$ stands for a hydrogen atom, a hydroxyl group or a methoxy group, $R'_5$ stands for a hydrogen atom, a hydroxyl group, a methoxy group or an isopentyl group, $R'_6$ stands for a hydroxyl group, a methoxy group or a carboxymethoxy group, and $R'_7$ stands for a hydrogen atom or a methoxy group, provided that (1) when $R'_2$ is a hydrogen atom, at least one of $R'_3$, $R'_4$, $R'_5$ and $R'_6$ is not a methoxy group, (2) when $R'_2$ is an isoprenyl group, $R'_1$ is a carboxymethoxy group, (3) when $R'_2$ is an isopentyl group and each of $R'_5$ and $R'_7$ is a hydrogen atom, $R'_4$ is a hydrogen atom and one of $R'$ and $R'_6$ is a carboxymethoxy group, (4) when $R'_4$ is not a hydrogen atom, $R'_3$ and $R'_4$ commonly stand for a hydroxyl group or a methoxy group, (5) when $R'_5$ is a hydroxyl group, $R'_6$ is a methoxy group, (6) when $R'_5$ is a methoxy group, $R'_6$ is a hydroxyl group, and (7) when $R'_6$ is a carboxymethoxy group, $R'_1$ is a hydroxyl group.

BEST MODE FOR CARRYING OUT THE INVENTION

A compound of formula I is prepared, for example, according to the following process.

A compound represented by the following general formula II (hereinafter referred to as "compound of formula II):

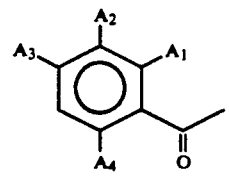

wherein $A_1$ stands for a hydroxyl group, a methoxymethoxy group, a methoxyethoxymethoxy group, a carboxymethoxy group, a methoxycarbonylmethoxy group, an ethoxycarbonylmethoxy group, a propoxycarbonylmethoxy group, a benzyloxy group, a p- nitrobenzyloxy group, a 2,4-dinitrobenzyloxy group, an o-nitrobenzyloxy group or a p-bromobenzyloxy group, $A_2$ stands for a hydrogen atom, an allyl group, an isoprenyl group or an isopentyl group, and A and $A_4$ independently stand for a hydrogen atom, a hydroxyl group, a methoxy group, a methoxymethoxy group, a methoxyethoxymethoxy group, a benzyloxy group, a p-nitrobenzyloxy group, a 2,4-dinitrobenzyloxy group, an o-nitrobenzyloxy group or a p-bromobenzyloxy group, is condensed with a compound represented by the following general formula III:

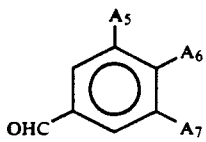

wherein $A_5$ stands for a hydrogen atom, an isoprenyl group, an isopentyl group, a hydroxyl group, a methoxy group, a methoxymethoxy group, a methoxyethoxymethoxy group, a benzyloxy group, a p-nitrobenzyloxy group, a 2,4-dinitrobenzyloxy group, an o-nitrobenzyloxy group or a p-bromobenzyloxy group, $A_6$ stands for a hydrogen atom, a hydroxyl group, a methoxy group, a methoxymethoxy group, a methoxyethoxymethoxy group, a benzyloxy group, a p-nitrobenzyloxy group, a 2,4-dinitrobenzyloxy group, an o-nitrobenzyloxy group or a p-bromobenzyloxy group, and $A_7$ stands for a hydrogen atom or a methoxy group, in an organic solvent by using a base, or the obtained condensation product is subjected to at least one operation selected from reduction, acetylation, alkoxycarbonylmethylation, ester hydrolysis and removal of a protecting group, whereby a compound of formula I is obtained.

The starting compound of formula II can be obtained by using commercially available 2',4',6'-trihydroxyacetophenone or 2',4'-dihydroxyacetophenone as the starting material and substituting the starting material with an isoprenyl group, an isopentyl group, a hydroxyl group, an acetyl group, a methyl group, a methoxymethyl group, a methoxyethoxymethyl group, a carboxymethyl group, a methoxycarbonylmethyl group, an allyl group, an ethoxycarbonylmethyl group, a propoxycarbonylmethyl group, a benzyl group, a p-nitrobenzyl group, a 2,4-dinitrobenzyl group, an o-nitrobenzyl group or a p-bromobenzyl group according to the intended substance.

More specifically, where 2',4',6'-trihydroxyacetophenone is used as the starting material, 2',4',6'-trihydroxyacetophenone is reacted with an allyl halide directly or after addition of a base such as sodium hydroxide, potassium hydroxide, sodium carbonate, potassium carbonate, metallic lithium, sodium hydride, potassium hydride or metallic sodium in an organic solvent such as tetrahydrofuran, acetone or dimethylformamide to effect allylation at the 3'-position, and the allylation product is reacted with dimethyl sulfate, methyl iodide, chloromethyl methyl ether, methoxyethoxymethyl chloride, benzyl bromide, p-nitrobenzyl chloride, 2,4-dinitrobenzyl chloride, o-nitrobenzyl chloride or p-bromobenzyl chloride after addition of a base such as N,N-diisopropylethylamine, sodium hydride, potassium hydride, sodium carbonate, potassium carbonate or triethylamine in an organic solvent such as anhydrous tetrahydrofuran, acetone or dimethylformamide, whereby a compound of formula II is obtained.

Alkoxycarbonylmethylation at the 2'-position is accomplished by reaction with a lower alkyl ester of an α-monohalogenoacetic acid in the presence of a base. As the solvent to be used, there can be mentioned organic solvents such as acetone, dimethylformamide and tetrahydrofuran, and as the base, there can be mentioned sodium hydride, potassium hydride, sodium carbonate, potassium carbonate, sodium methylate and sodium ethylate. As the lower alkyl ester of the α-monohalogenoacetic acid, there can be mentioned esters formed by substituting the hydrogen atom at the α-position with a halogen in a lower alkyl ester of acetic acid, such as methyl acetate, ethyl acetate, propyl acetate, butyl acetate or pentyl acetate.

The isoprenyl group at the 3'-position can be reduced to an isopentyl group according to an ordinary reduction process customarily adopted.

As specific examples of the allyl halide, there can be mentioned 1-chloro-3-methyl-2-butene and 1-bromo-3-methyl-2-butene. Since the reaction is a substitution of the hydrogen at the 3'-position, the reaction is similarly advanced regardless of the kind of the allyl halide. The reaction is ordinarily carried out at a temperature of from about −10° to about 80° C.

Where 2',4'-dihydroxyacetophenone is used as the starting material, 2',4'-dihydroxyacetophenone is reacted with an allyl halide directly or after addition of a base such as sodium hydroxide, potassium hydroxide, sodium carbonate, potassium carbonate, metallic lithium, sodium hydride, potassium hydride or metallic sodium in an organic solvent such as anhydrous tetrahydrofuran, acetone, dimethylformamide or tetrahydrofuran to effect allylation at the 3'-position, and the allylation product is reacted with dimethyl sulfate, methyl iodide, chloromethyl methyl ether, methoxyethoxymethyl chloride, benzyl bromide, p-nitrobenzyl chloride, 2,4-dinitrobenzyl chloride, o-nitrobenzyl chloride or p-bromobenzyl chloride after addition of a base such as N,N-diisopropylethylamine, sodium hydride, potassium hydride, sodium carbonate, potassium carbonate or triethylamine in an organic solvent such as tetrahydrofuran, acetone or dimethylformamide, whereby a compound of formula II is obtained.

The same compounds as exemplified above can be mentioned as the allyl halide. Also, since this reaction is a substitution of the hydrogen atom at the 3'-position, the reaction is similarly advanced regardless of the allyl halide, but allyl chloride is preferred. The reaction is ordinarily carried out at a temperature of from about −10° to about 80° C.

A compound of formula III can be obtained by using commercially available vaniline, isovaniline, p-anisaldehyde, p-hydroxybenzaldehyde, 3,4-dihydroxybenzaldehyde or syringylaldehyde as the starting material and substituting the starting compound with an isoprenyl group, an isopentyl group, a hydroxyl group, an acetyl group, a methyl group, a methoxymethyl group, a methoxyethoxymethyl group, a carboxymethyl group, a methoxycarbonylmethyl group, a benzyl group, a p-nitrobenzyl group, a 2,4-dinitrobenzyl group, an o-nitrobenzyl group or a p-bromobenzyl group according to the intended substance.

More specifically, vaniline, isovaniline, p-anisaldehyde, p-hydroxybenzaldehyde, 3,4-dihydroxybenzaldehyde or syringylaldehyde is reacted with an allyl halide directly or after addition of a base such as sodium hydroxide, potassium hydroxide, sodium carbonate, potassium carbonate, metallic lithium, sodium hydride, potassium hydride or metallic sodium in an organic solvent such as tetrahydrofuran, acetone or dimethylformamide to effect allylation at the 3-position, and the allylation product is reacted with dimethyl sulfate, methyl iodide, chloromethyl methyl ether, methoxyethoxymethyl chloride, benzyl bromide, p-nitrobenzyl chloride, 2,4-dinitrobenzyl chloride, o-nitrobenzyl chloride or p-bromobenzyl chloride after addition of a base such as N,N-diisopropylethylamine, sodium hydride, potassium hydride, sodium carbonate, potassium carbonate or triethylamine in an organic solvent such as tetrahydrofuran, acetone or dimethylformamide, whereby a compound of formula III is obtained.

The same compounds as exemplified above can be mentioned as the allyl halide. Also, since this reaction is substitution of the hydrogen atom at the 3-position, the reaction is similarly advanced regardless of the kind of the allyl halide. Preferably, the reaction is carried out at a temperature of from $-10°$ C. to a level lower than the boiling point of the solvent used.

Examples of the production of compounds of formulae II and III will now be described.

Production Example 1

In tetrahydrofuran were dissolved and suspended 66.5 g of 2',4',6'-trihydroxyacetophenone and 173.0 g of potassium carbonate, and 56.0 ml of 1-chloro-3-methyl-2-butene was dropped into the solution. The mixture was stirred at room temperature for 2 hours and extracted with dimethyl ether, and the organic layer was washed with a 5% solution of potassium carbonate and then with water. The organic layer was shaken with a saturated solution of sodium chloride, dried with anhydrous sodium sulfate and concentrated under a reduced pressure. Recrystallization from benzene gave 31.8 g (yield=34.0%) of 2',4',6'-trihydroxy-3'-(3-methyl-2-butenyl)acetophenone.

Then, 30.0 g of 2',4',6'-trihydroxy-3'-(3-methyl-2-butenyl)acetophenone was dissolved in tetrahydrofuran and 131.7 ml of N,N-diisopropylethylamine was added to the solution, and the mixture was stirred for 1 hour. Then, 48.0 ml of chloromethyl methyl ether was dropped into the mixture and the mixture was stirred for 3 hours. The mixture was extracted with dimethyl ether, and the organic layer was washed with water, dried with anhydrous sodium sulfate and concentrated under reduced pressure. Crystallization from ethyl acetate gave 21.5 g of 2'-hydroxy-4',6'-bis(methoxymethoxy)-3'-(3-methyl-2-butenyl)acetophenone.

Production Example 2

In 750 ml of tetrahydrofuran was dissolved 149.9 g of 2',4'-dihydroxyacetophenone, and 409.2 g of anhydrous potassium carbonate and 150 ml of 1-chloro-3-methyl-2-butene were added to the solution and the mixture was stirred at room temperature in a nitrogen current for 5 days. After the reaction, the reaction mixture was made acidic by addition of hydrochloric acid and extracted with diethyl ether. The solvent was removed from the ether extract by distillation. Then, 800 ml of hexane was added to the obtained residue and the hexanesoluble substance was removed by decantation to obtain 2',4'-dihydroxy-3'-(3-methyl-2-butenyl)acetophenone in the form of a colorless solid. Then, 19.0 g of the so-obtained solid was dissolved in 160 ml of acetone, and 14.2 g of anhydrous potassium carbonate and 6.2 ml of methyl iodide were added to the solution and the mixture was stirred at room temperature overnight in a nitrogen current. After the reaction, the solvent was removed by distillation and the obtained residue was extracted with diethyl ether. The solvent was removed from the extract by distillation to obtain 20.0 g (yield =99.1%) of 2'-hydroxy-4'-methoxy-3'-(3-methyl-2-butenyl)acetophenone.

Infrared absorption spectrum $v_{max}^{KBr}$ cm$^{-1}$: 2964, 2916, 2844, 1632, 1500, 1418, 1370, 1336, 1312, 1272, 1234, 1166, 1132, 1090, 1022, 994, 960, 906, 880, 820, 788, 680, 652. 622.

Proton nuclear magnetic resonance spectrum ($\delta$ ppm in CDCl$_3$): 1.67 (3H, br, s), 1.78 (3H, br, s), 2.55 (3H, s), 3.35 (2H, d, J=6.8 Hz), 3.89 (3H, s), 5.19 (1H, brt, J=6.8 Hz), 6.45 (1H, d, J=8.8 Hz), 7.60 (1H, d, J=8.8 Hz),
12.74 (1H, s).

Mass spectrum: M/Z (%) 234 (M+, 28), 219 (13), 191 (24), 179 (52), 163 (14), 149 (12), 43 (100).

Production Example 3

In 250 ml of anhydrous tetrahydrofuran was dissolved 50.0 g of 2',4',6'-trihydroxyacetophenone, and 123.1 g of anhydrous potassium carbonate was added to the solution and the mixture was stirred at room temperature for 30 minutes. Then, 37.2 g of 1-chloro3-methyl-2-butene was added dropwise to the mixture over a period of 20 minutes and reaction was carried out at room temperature for 24 hours. After the reaction, the reaction mixture was extracted with 2 l of ethyl acetate and the solvent was removed from the ethyl acetate layer by distillation, and the residue was recrystallized from a benzene/petroleum ether mixed solvent to obtain 38.6 g (yield=55.0%) of 2',4',6'-trihydroxy-3'-(3-methyl-2-butenyl)acetophenone in the form of a yellow prism.

Then, 23.7 g of this 2',4',6'-trihydroxy-3'-(3-methyl-2-butenyl)acetophenone was dissolved in 400 ml of acetone, and 55.6 g of potassium carbonate was added to the solution and the mixture was stirred at 40° C. for 4 hours. Then, 19.5 ml of dimethyl sulfate was added to the mixture, and stirring was conducted for 4 hours. The reaction liquid was poured into 2.5 l of ice water, and the precipitated crystal was recovered by filtration, washed with 1 l of water, dried and recrystallized from hexane to obtain 19.5 g (yield=73.8%) of 2'-hydroxy-4',6'-dimethoxy-3'-(3-methyl-2-butenyl)acetophenone in the form of a light-yellow needle.

Melting point: 110.2° to 111.2° C.

Infrared absorption spectrum $v_{max}^{KBr}$ cm$^{-1}$: 2996, 2948, 2912, 2848, 1624, 1594, 1468, 1420, 1290, 1274, 1212, 1120, 1096, 892, 788.

Proton nuclear magnetic resonance spectrum ($\delta$ ppm in acetone-d$_6$): 1.62 (3H, d, J=1.5 Hz), 1.73 (3H, d), 2.56 (3H, s), 3.22 (2H, d, J=7.3 Hz), 3.93 (3H, s), 3.95 (3H, s), 5.16 (1H, t. sep, J=7.3, 1.5 Hz), 6.22 (1H, s), 14.04 (1H, s).

Mass spectrum:
M/Z (%) 264 (M+, 95), 249 (97), 221 (83), 209 (100, 207 (14), 196 (12), 193 (42), 191 (20), 181 (25), 179 (10), 43 (49), 41 (11)

Production Example 4

To a mixture of 43.6 g of 2'-hydroxy-4'-methoxy-3'-(3-methyl-2-butenyl)acetophenone obtained in Production Example 2 and 4.9 g of sodium hydride was added 400 ml of dimethylformamide, and the mixture was stirred at 0° C. for 1 hour. Then, 31.3 g of methyl α-bromoacetate was added to the mixture and stirring was conducted at room temperature for 4 hours, and after the reaction, the reaction mixture was extracted with diethyl ether and the solvent was removed by distillation. The residue was subjected to the silica gel column chromatography [230-400 mesh silica gel, eluting solvent=n-hexane/ethyl acetate (4/1)]. to obtain 46.7 g (yield=82.0%) of 2'-methoxycarbonylmethoxy-4'-methoxy-3'-(3-methyl-2-butenyl)acetophenone in the form of a colorless oil.

Infrared absorption spectrum $\nu_{max}^{KBr}$ cm$^{-1}$: 1764, 1680, 1590, 1462, 1440, 1358, 1270, 1206, 1178, 1132, 1094

Proton nuclear magnetic resonance spectrum (δ ppm in CDCl$_3$): 1.67 (3H, d, J=1.0 Hz), 1.74 (3H, s), 2.58 (3H, s), 3.41 (2H, d, J=6.8 Hz), 3.81 (3H, s), 3.88 (3H, s), 4.47 (2H, s), 5.13 (1H, t, q, J=6.8, 1.0 Hz), 6.72 (1H, d, J=8.8 Hz), 7.60 (1H, d, J=8.8 Hz).

Mass spectrum: M/Z (%) 306 (M+, 6), 234 (16), 233 (100), 217 (9), 215 (9), 203 (6), 191 (12), 179 (24), 175 (6), 163 (6), 161 (6), 149 (10), 127 (7), 43 (58).

Production Example 5

An ethyl acetate solution of 22.2 g of 2'-hydroxy4',6'-dimethoxy-3'-(3-methyl-2-butenyl)acetophenone was added into a sufficiently hydrogen gas-absorbed suspension of 1.5 g of 5% palladium-carbon in 20 ml of ethyl acetate, and the mixture was stirred at room temperature for 2 hours in a hydrogen gas atmosphere. After the reaction, the reaction mixture was filtered and the solvent was removed by distillation. The residue was recrystallized from n-hexane to obtain 20.4 g (yield=91.2%) of 2'-hydroxy-3'-isopentyl-4',6'-dimethoxyacetophenone in the form of a colorless needle.

Melting point: 100° to 100.5° C.

Infrared absorption spectrum $\nu_{max}^{KBr}$ cm$^{-1}$: 2952, 2868, 1634, 1590, 1468, 1424, 1382, 1360, 1296, 1276, 1228, 1206, 1146, 1106, 1080, 888, 794.

Proton nuclear magnetic resonance spectrum (δ ppm in CDCl$_3$): 0.93 (6H, d, J=6.8 Hz), 1.34 (2H, m), 1.56 (1H, m), 2.55 (2H, m), 2.61 (3H, s), 3.88 (3H, s), 3.89 (3H, s), 5.94 (1H, s), 13.92 (1H, s).

Mass spectrum: M/Z (%) 266 (M+, 20), 210 (23), 209 (100), 195 (8), 191 (21), 179 (4), 161 (5).

To 16.7 g of the so-obtained 2'-hydroxy-3'-isopentyl-4',6'-dimethoxyacetophenone and 1.5 g of sodium hydride was added 130 ml of dimethylformamide, and 9.9 g of methyl α-bromoacetate was further added and the mixture was stirred for 1.5 hours at 0° C. and for 2 hours at room temperature to effect reaction. After the reaction, the reaction mixture was made acidic by dilute hydrochloric acid, extracted with diethyl ether and filtered. The solvent was removed from the filtrate by distillation. The obtained residue was subjected to the silica gel column chromatography [230-400 mesh silica gel, eluting solvent=n-hexane/ethyl acetate (4/1)] to obtain 14.9 g (yield=70.3%) of 3'-isopentyl-4',6'-dimethoxy-2'-methoxycarbonylmethoxyacetophenone.

Melting point: 49.5° to 50.5° C.

Infrared absorption spectrum $\nu_{max}^{KBr}$ cm$^{-1}$: 2956, 1756, 1676, 1600, 1468, 1440, 1414, 1264, 1254, 1226, 1212, 1152, 1138, 1110, 1080, 810.

Proton nuclear magnetic resonance spectrum (δ ppm in CDCl$_3$): 0.92 (6H, d, J=6.4 Hz), 1.35 (2H, m), 1.41 (1H, m), 2.49 (3H, s), 2.52 (2H, m), 3.80 (3H, s), 3.82 (3H, s), 3.85 (3H, s), 4.49 (2H, s), 6.28 (1H, s).

Mass spectrum: M/Z (%) 338 (M+, 40), 323 (33), 282 (15), 281 (100), 265 (26), 239 (11), 209 (40) 179 (30), 45 (21), 43 (24).

Production Example 6

In 15 ml of anhydrous tetrahydrofuran was dissolved 3.0 g of 2',4',6'-trihydroxyacetophenone, and 7.4 g of anhydrous potassium carbonate was added to the solution and the mixture was stirred at room temperature for 30 minutes. Then, 2.5 g of 3-bromo-1-propene was added to the mixture and reaction was carried out at room temperature for 3 hours. After the reaction, the reaction mixture was extracted with 500 ml of diethyl ether, and the solvent was removed from the extract by distillation. The obtained residue was recrystallized from benzene to obtain 1.5 g (yield=41.5%) of 2',4',6'-trihydroxy-3'-(2-propenyl)acetophenone in the form of a colorless prism.

Melting point: 158° to 159° C.

Infrared absorption spectrum $\nu_{max}^{KBr}$ cm$^{-1}$: 3440, 3312, 1636, 1600, 1560, 1516, 1436, 1398, 1370, 1358, 1284, 1236, 1214, 1154, 1076, 1026, 910, 816, 588, 560, 540.

Proton nuclear magnetic resonance spectrum (δ ppm in acetone-d$_6$): 2.62 (3H, s), 3.29 (2H, dt, J=6.3, 1.5 Hz), 4.86 (1H, ddt, J=10.0, 2.2, 1.5 Hz), 4.98 (1H, ddt, J=17.1, 2.2, 1.5 Hz), 5.91 (1H, ddt, J=17.1, 10.0, 6.3 Hz), 6.08 (1H, s).

Mass spectrum: M/Z (%) 208 (M+, 74), 194 (12), 193 (100), 165 (21), 69 (15), 43 (15).

In 160 ml of anhydrous tetrahydrofuran were dissolved 18.4 g of the so-obtained 2',4',6'-trihydroxy3'-(2-propenyl)acetophenone and 57.1 g of N,N-diisopropylethylamine, and 28.4 g of chrolomethyl methyl ether was added to the solution under ice cooling and the reaction mixture was stirred under ice cooling for 1 hour, and further, stirred at room temperature for 4 hours to effect a reaction. The reaction mixture was extracted with diethyl ether and filtered, and the solvent was removed from the filtrate by distillation. The obtained residue was subjected to the silica gel column chromatography [eluting solvent=n-hexane/ethyl acetate (7/1)] to obtain 24.8 g (yield=94.7%) of 2'-hydroxy-4',6'-bismethoxymethoxy-3'-(2-propenyl-)acetophenone in the form of a colorless oil.

Infrared absorption spectrum $\nu_{max}^{KBr}$ cm$^{-1}$: 2924, 1620, 1598, 1454, 1444, 1428, 1412, 1376, 1270, 1232, 1204, 1154, 1126, 1104, 1070, 1046, 996, 970, 954, 918, 870.

Proton nuclear magnetic resonance spectrum (δ ppm in acetone-d$_6$): 2.66 (3H, s), 3.32 (2H, dt, J=6.4, 1.5 Hz), 3.45 (3H, s), 3.52 (3H, s), 4.88 (1H, ddt, J=9.8, 2.0, 1.5 Hz), 4.98 (1H, ddt, J=17.1, 2.0, 1.5 Hz), 5.29 (2H, s), 5.35 (2H, s), 5.90 (1H, ddt, J=17.1, 9.8, 6.4 Hz), 6.49 (1H, s), 13.95 (1H, s, disappeared by addition of D$_2$O).

Mass spectrum: M/Z (%) 296 (M+,5), 222 (3), 219 (3), 190 (5), 177 (5), 45 (100), 43 (5).

Production Example 7

To 50.1 g of 2',4',6'-trihydroxyacetophenone and 123.5 g of anhydrous potassium carbonate was added 500 ml of anhydrous acetone, and the mixture was stirred at room temperature for 30 minutes. Then, 78.9 g of dimethyl sulfate was added to the reaction mixture, and the mixture was stirred at room temperature for 1.5 hours to effect a reaction. After the reaction, the reaction mixture was neutralized with dilute hydrochloric acid, extracted with diethyl ether and filtered, and the solvent was removed from the filtrate by distillation.

The obtained residue was recrystallized from n-hexane to obtain 55.2 g (yield=94.4%) of 2'-hydroxy-4',6'-dimethoxyacetophenone in the form of a colorless prism.

Melting point: 77° to 78° C.

Infrared absorption spectrum $\nu_{max}^{KBr}$ cm$^{-1}$: 1622, 1596, 1574, 1460, 1440, 1424, 1368, 1272, 1222, 1206, 1156, 1110, 1080, 894, 834, 596.

Proton nuclear magnetic resonance (δ ppm in CDCl$_3$): 2.61 (3H, s), 3.82 (3H, s), 3.85 (3H, s), 5.92 (1H, d, J=2.4 Hz), 6.05 (1H, d, J=2.4 Hz), 14.03 (1H, s, disappeared by addition of D$_2$O).

Mass spectrum: M/Z (%) 196 (M+, 36), 182 (10), 166 (10), 138 (6), 95 (7), 69 (7).

Production Example 8

In 60 ml of dimethylformamide were dissolved 5.0 g of 2',4'-dihydroxyacetophenone and 6.37 g of N,N-diisopropylethylamine, and 2.72 ml of chloromethyl methyl ether was gradually added to the solution under ice cooling. The mixture was stirred under ice cooling for 20 minutes and a reaction was carried out at room temperature for 1.5 hours. After the reaction, the reaction mixture was extracted with 300 ml of diethyl ether, and the diethyl ether layer was washed with water (100 ml×2 times), shaken with a saturated aqueous solution of sodium chloride (50 ml×2 times), dried with anhydrous sodium sulfate and filtered. The solvent was removed from the filtrate by distillation and the residue was subjected to the silica gel chromatography (3.5 cm in diameter; 72.8 g; n-hexane/ethyl acetate=4/1; 0.3 kg/cm$^2$) to obtain 5.66 g (yield=87.8%) of 2'-hydroxy-4'-methoxymethoxyacetophenone in the form of a colorless oil.

Infrared absorption spectrum $\nu_{max}^{KBr}$ cm$^{-1}$: 1638, 1582, 1504, 1368, 1332, 1250, 1218, 1154, 1142, 1082, 1062, 994, 942, 922.

Proton nuclear magnetic resonance spectrum (δ ppm in CDCl$_3$): 2.56 (3H, s), 3.47 (3H, s), 5.20 (2H, s), 6.54 (1H, dd, J=8.8, 2.4 Hz), 6.59 (1H, d, J=8.8, 2.4 Hz), 7.65 (1H, d, J=8.8 Hz), 12.61 (1H, s, disappeared by addition of D$_2$O).

Mass spectrum: M/Z (%) 196 (M+, 100), 151 (35), 137 (10), 135 (12), 65 (12), 53 (12), 51 (10), 46 (22), 43 (47).

Production Example 9

In 750 ml of tetrahydrofuran was dissolved 149.95 g of 2',4'-dihydroxyacetophenone, and 409.26 g of anhydrous potassium carbonate and 150 ml of 1-chloro-3-methyl-2-butene were added to the solution and the mixture was stirred at room temperature in a nitrogen current for 5 days. After the reaction, 3N hydrochloric acid was added to the reaction liquid under cooling to make the aqueous layer acidic, and the aqueous layer was extracted with ether. The ether extract was washed with water and dried with anhydrous sodium sulfate and the solvent was removed by distillation. Then, 800 ml of hexane was added to the obtained residue and the hexane-soluble substances were removed by decantation to obtain 98.55 g (yield=45.4%) of 2',4'-dihydroxy-3-(3-methyl-2-butenyl)acetophenone in the form of a colorless solid.

Infrared absorption spectrum $\nu_{max}^{KBr}$ cm$^{-1}$: 3168, 2968, 2912, 1622, 1590, 1494, 1452, 1372, 1320, 1272, 1164, 1126, 1100, 1056, 1024, 1000, 980, 914, 888, 848, 834, 792, 778, 718, 614.

Proton nuclear magnetic resonance spectrum (δ ppm in acetone-d$_6$): 1.63 (3H, d, J=1.5 Hz), 1.76 (3H, d, J=1.5 Hz), 2.53 (3H, s), 3.34 (2H, d, J=7.3 Hz), 5.25 (1H, t, septet, J=7.3 Hz, J=1.5 Hz), 6.49 (1H, d, J=8.8 Hz), 7.63 (1H, d, J=8.8 Hz), 9.31 (1H, brs, disappeared by addition of D$_2$O), 13.10 (1H, s, disappeared by addition of D$_2$O).

Mass spectrum: M/Z (%) 220 (M+, 62), 205 (21), 177 (30), 165 (91), 149 (32), 147 (22), 43 (100).

Then, 19.00 g of 2',4'-dihydroxy-3'-(3-methyl-2-butenyl)acetophenone was dissolved in 160 ml of acetone, and 14.29 g of anhydrous potassium carbonate and 6.2 ml of methyl iodide were added to the solution and the mixture was stirred at room temperature in a nitrogen current overnight. After the reaction, the solvent was removed by distillation and the obtained residue was extracted with ether, the extract was washed with water, dried with anhydrous sodium sulfate, and filtered. The solvent was removed from the filtrate by distillation to obtain 20.02 g (yield=99.1%) of 2'-hydroxy-4'-methoxy-3'-(3-methyl-2-butenyl)acetophenone in the form of a colorless oil.

Infrared absorption spectrum $\nu_{max}^{KBr}$ cm$^{-1}$: 2964, 2916, 2844, 1632, 1500, 1418, 1370, 1336, 1312, 1272, 1234, 1166, 1132, 1090, 1022, 994, 960, 906, 880, 820, 788, 680, 652, 622.

Proton nuclear magnetic resonance spectrum (δ ppm in CDCl$_3$): 1.67 (3H, brs), 1.78 (3H, brs), 2.55 (3H, s), 3.35 (2H, d, J=6.8 Hz), 3.89 (3H, s), 5.19 (1H, brt, J=6.8 Hz), 6.45 (1H, d, J=8.8 Hz), 7.60 (1H, d, J=8.8 Hz), 12.74 (1H, s).

Mass spectrum: M/Z (%) 234 (M+, 28), 219 (13), 191 (24), 179 (52), 163 (14), 149 (12), 43 (100).

Production Example 10

In 3 ml of dimethylformamide was dissolved 456 mg of 2',4'-dihydroxyacetophenone, and the solution was cooled to 0° C. and 1.73 ml of N,N-diisopropylethylamine was added to the solution. Then, 0.61 ml of chloromethyl methyl ether was added to the mixture and reaction was carried out for 18 hours with stirring. After the reaction, the reaction mixture was poured in ice water and extracted with ethyl acetate. The organic layer was washed with water, dried with anhydrous sodium sulfate and filtered. The solvent was removed from the filtrate by distillation to obtain 707.9 mg (yield=98.3%) of 2',4'-bis(methoxymethoxy)acetophenone in the form of a colorless transparent liquid.

Infrared absorption spectrum $\nu_{max}^{KBr}$ cm$^{-1}$: 2952, 1668, 1604, 1574, 1494, 1398, 1358, 1258, 1218, 1206, 1156, 1134, 1084, 1058, 1008, 924, 844, 816.

Proton nuclear magnetic resonance spectrum (δ ppm in CDCl$_3$): 2.60 (3H, s), 3.47 (3H, s), 3.52 (3H, s), 5.19 (2H, s), 5.27 (2H, s), 6.71 (1H, dd, J=8.8, 2.4 Hz), 6.82 (1H, d, J=2.4 Hz), 7.77 (1H, d, J=8.8 Hz).

Mass spectrum: M/Z (%) 240 (M+, 5), 225 (1), 209 (1), 181 (1), 180 (3), 179 (2), 165 (2), 164 (2), 70 (2), 61 (3), 45 (100), 43 (22), 28 (3).

Production Example 11

In 200 ml of anhydrous tetrahydrofuran were dissolved 30 g of 2',4',6'-trihydroxyacetophenone and 115.0 g of N,N-diisopropylethylamine, and 50.2 g of chloromethyl methyl ether was gradually added to the solution under ice cooling over a period of 20 minutes and the reaction mixture was stirred under ice cooling for 1 hour and at room temperature for 4 hours to effect reaction. After the reaction, the reaction mixture was extracted with 3 l of ether, and the ether layer was washed with water (500 ml×3 times), shaken with a saturated aqueous solution of sodium chloride (300 ml×2 times), dried with anhydrous sodium sulfate, and filtered. The solvent was removed from the filtrate by distillation and the obtained residue was recrystallized from a mixed solvent of methanol and water to obtain 18.9 g (yield=41.4%) of 2'-hydroxy-4',6'-bis(methoxyacetophenone in the form of a colorless prism.

Infrared absorption spectrum $\nu_{max}^{KBr}$ cm$^{-1}$: 3000, 2960, 2908, 2832, 1622, 1594, 1484, 1468, 1448, 1436, 1418, 1362, 1318, 1270, 1222, 1208, 1150, 1108, 1080, 1064, 1026, 980, 946, 928, 866, 830, 648, 602, 534.

Proton nuclear magnetic resonance spectrum (δ ppm in acetone-d$_6$): 2.64 (3H, s), 3.45 (3H, s), 3.53 (3H, s), 5.24 (2H, s), 5.36 (2H, s), 6.19 (1H, d, J=2.4 Hz), 6.29 (1H, d, J=2.4 Hz), 13.73 (1H, s, disappeared by addition of D$_2$O).

Mass spectrum:
M/Z (%) 256 (M$^+$, 75), 183 (14), 182 (100, 69 (12), 46 (22), 43 (32).

Production Example 12

In 250 ml of anhydrous tetrahydrofuran was dissolved 50.0 g of 2',4',6'-trihydroxyacetophenone, and 123.15 g of anhydrous potassium carbonate was added to the solution and the mixture was stirred at room temperature for 30 minutes. Then, 37.23 g of 1-chloro-3-methyl-2-butene was dropped into the solution over a period of 20 minutes and a reaction was carried out at room temperature for 24 hours. After the reaction, the reaction mixture was extracted with 2 l of ethyl acetate, and the ethyl acetate layer was washed with water (500 ml×4 times), shaken with a saturated aqueous solution of sodium chloride (300 ml×2 times), dried with anhydrous sodium sulfate and filtered. The solvent was removed from the filtrate by distillation and the obtained residue was recrystallized from a mixed solvent of benzene and petroleum ether to obtain 38.6 g (yield=55.0%) of 2',4',6'-trihydroxy-3'-(3-methyl-2-butenyl)acetophenone in the form of a yellow prism.

Infrared absorption spectrum $\nu_{max}^{KBr}$ cm$^{-1}$: 3420, 3328, 2976, 2924, 1640, 1600, 1562, 1524, 1512, 1452, 1434, 1402, 1368, 1282, 1234, 1172, 1150, 1070, 816, 588.

Proton nuclear magnetic resonance spectrum (δ ppm in acetone-d$_6$): 1.62 (3H, d, J=1.2 Hz), 1.73 (3H, s), 2.60 (3H, s), 3.23 (2H, d, J=7.3 Hz), 5.22 (1H, dd, J=7.3 Hz, 1.2 Hz), 6.05 (1H, s).

Mass spectrum: M/Z (%) 236 (M$^+$, 64), 221 (33), 203 (14), 193 (30), 181 (100), 165 (37), 163 (28), 153 (24), 43 (57) .

Production Example 13

In 170 ml of anhydrous tetrahydrofuran were dissolved 20.64 g of the 2',4',6'-trihydroxy-3'-(3-methyl-2-butenyl)acetonhenone obtained in Production Example 12 and 67.5 of N,N-diisopropylethylamine, and 35.0 g of chloromethyl methyl ether was gradually added to the solution under ice cooling over a period of 25 minutes. The reaction mixture was stirred under ice cooling for 1 hour and at room temperature for 3 hours to effect a reaction. After the reaction, the reaction mixture was extracted with ethyl acetate (1500 ml), and the ethyl acetate layer was washed with water (500 ml×4 times), shaken with a saturated aqueous solution of sodium chloride (300 ml×2 times), dried with anhydrous sodium sulfate, and filtered. The solvent was removed from the filtrate by distillation to quantitatively obtain 28.22 g of 2'-hydroxy-4',6'-bis(methoxymethoxy)3'-(3-methyl-2-butenyl)acetophenone in the form of yellow oil.

Infrared absorption spectrum $\nu_{max}^{KBr}$ cm$^{-1}$: 2956, 2920, 2828, 1618, 1602, 1486, 1428, 1410, 1374, 1278, 1230, 1156, 1108, 1072, 1044, 1014, 992, 960, 924, 870.

Proton nuclear magnetic resonance spectrum (δ ppm in CDCl$_3$): 1.66 (3H, s), 1.77 (3H, s), 2.65 (3H, s), 3.30 (2H, d, J=7.0 Hz), 3.47 (3H, s), 3.51 (3H, s), 5.21 (1H, t, J=7.0 Hz), 5.23 (2H, s), 5.25 (2H, s), 6.39 (1H, s), 13.82 (1H, s, disappeared by addition of D$_2$O).

Mass spectrum: M/Z (%) 324 (M$^+$, 4), 291 (5), 279 (10), 247 (8), 217 (10), 205 (20), 69 (6), 45 (100), 43 (12), 41 (7).

Production Example 14

In 400 ml of acetone was dissolved 23.70 g of the 2',4',6'-trihydroxy-3'-(3-methyl-2-butenyl)acetophenone obtained in Production Example 12, and 55.68 g of potassium carbonate was added to the solution and the mixture was stirred at 40° C. for 30 minutes. Then, 19.5 ml of dimethyl sulfate was added to the mixture, and a reaction was carried out for 4 hours with stirring. After the reaction, the reaction mixture was poured into 2.5 l of ice water, and the precipitated crystal was recovered by filtration, washed with 1.0 l of pure water, and dried. The obtained crude crystal was dissolved in hot hexane and the solution was hot-filtered. Recrystallization from hexane gave 19.56 g (yield=73.8%) of 2'-hydroxy-4', 6'-dimethoxy-3'-(3-methyl-2-butenyl)acetophenone in the form of a light-yellow needle.

Infrared absorption spectrum $\nu_{max}^{KBr}$ cm$^{-1}$: 2996, 2948, 2912, 2848, 1624, 1594, 1468, 1420, 1290, 1274, 1212, 1120, 1096, 892, 788.

Proton nuclear magnetic resonance spectrum (δ ppm in acetone-d$_6$): 1.62 (3H, d, J=1.5 Hz), 1.73 (3H, d, J=1.5 Hz), 2.56 (3H, s), 3.22 (2H, d, J=7.3 Hz), 3.93 (3H, s), 3.95 (3H, s), 5.16 (1H, t, sept, J 7.3, 1.5 Hz), 6.22 (1H, s), 14.04 (1H, s, disappeared by addition of D$_2$O).

Mass spectrum: M/Z (%) 264 (M+, 95), 249 (97), 221 (83), 209 (100), 207 (14), 196 (12), 193 (42), 191 (20), 181 (25), 179 (10), 43 (49), 41 (11).

Production Example 15

In 250 ml of dimethylformamide was dissolved 40.00 g of the 2',4'-dihydroxy-3'-(3-methyl-2-butenyl-)acetophenone obtained as the intermediate in Production Example 9, and 27.61 g of anhydrous potassium carbonate and 24.0 ml of benzyl bromide were added to the solution and the mixture was stirred at −5° C. in a nitrogen current for 2 days. After the reaction, water was added to the reaction liquid and the formed precipitate was recovered by filtration and recrystallized from n-hexane to obtain 48.55 g (yield=86.1%) of 4'-benzyloxy-2'-hydroxy-3'-(3-methyl-2-butenyl)acetophenone in the form of a colorless needle.

Infrared absorption spectrum $\nu_{max}^{KBr}$ cm$^{-1}$: 3068, 3024, 2988, 2964, 2912, 2852, 1632, 1614, 1530, 1502, 1454, 1418, 1394, 1366, 1330, 1306, 1288, 1276, 1234, 1164, 1130, 1006, 1090, 1072, 1030, 1022, 966, 844, 808, 788, 752, 728, 690, 640.

Proton nuclear magnetic resonance spectrum (δ ppm in CDCl$_3$): 1.67 (3H, brs), 1.71 (3H, brs), 2.54 (3H, s), 3.41 (2H, d, J=7.3 Hz), 5.16 (2H, s), 5.23 (1H, brt, J=7.3 Hz), 6.48 (1H, d, J=8.8 Hz), 7.31-7.43 (5H, m), 7.56 (1H, d, J=8.8 Hz), 12.76 (1H, s).

Mass spectrum: M/Z (%) 310 (M$^+$, 14) 255 (5), 220 (6), 219 (41), 177 (9), 165 (9), 92 (8), 91 (100), 43 (37).

Production Example 16

A solution of 2.08 g of the 2'-hydroxy-4',6'-bis(methoxymethoxy)-3'-(3-methyl-2-butenyl)acetophenone obtained in Production Example 13 in ethanol (20 ml) was added to a sufficiently hydrogen gas-absorbed suspension of 1.0 g of 5% palladium-carbon in 30 ml of ethanol, and the mixture was stirred at room temperature under atmospheric pressure in a hydrogen atmosphere. After the reaction, the reaction mixture was filtered, and the solvent was removed from the filtrate by distillation. The obtained residue was subjected to the silica gel column chromatography (3.0 cm in diameter, 60 g of silica gel, 0.3 kg/cm$^2$) using a mixed solvent of n-hexane and ethyl acetate (n-hexane/ethyl acetate = 3/1). Fractions of 50 ml were recovered, and 1.73 g (yield = 82.8%) of 2'-hydroxy-3'-isopentyl-4',6'-bis(methoxymethoxy)acetophenone in the form of a yellow oil was obtained from the third to fifth fractions.

Infrared absorption spectrum $v_{max}^{KBr}$ cm$^{-1}$: 3000, 2952, 2928, 2864, 2828, 1614, 1592, 1486, 1468, 1452, 1426, 1412, 1376, 1360, 1306, 1276, 1230, 1206, 1156, 1132, 1106, 1086, 1064, 1042, 1024, 996, 972, 952, 940, 920, 858, 820.

Proton nuclear magnetic resonance spectrum ($\delta$ ppm in CDCl$_3$): 0.95 (6H, d, J = 6.3 Hz), 1.36 (2H, m), 1.59 (1H, m), 2.60 (1H, t, J = 7.8 Hz), 2.65 (3H, s), 3.49 (3H, s), 3.51 (3H, s), 5.22 (2H, s), 5.25 (2H, s), 6.38 (1H, s), 13.79 (1H, s).

Mass spectrum: M/Z (%) 326 (M$^+$, 7) 252 (4), 207 (9), 196 (5), 195 (5), 164 (7), 45 (100).

Production Example 17

To 14.0 g of vaniline and 51.0 g of potassium carbonate was added 280 ml of acetophenone, and chloromethyl methyl ether was further added and the mixture was refluxed for 1 hour. The reaction liquid was cooled to room temperature and filtered, and the filtrate was concentrated under reduced pressure. The reaction mixture was dissolved in ether, washed with water, shaken with a saturated aqueous solution of sodium chloride, dried with anhydrous sodium sulfate and concentrated under reduced pressure. The concentrate was subjected to the column chromatography [230–400 mesh Kieselgel; eluting solvent = hexane/ethyl acetate (2/1)] to obtain 9.6 g (yield = 53.1%) of 3-methoxy-4-methoxymethoxybenzaldehyde.

Melting point: 39.0° to 40.0° C.

Infrared absorption spectrum $v_{max}^{KBr}$ cm$^{-1}$: 2952, 2828, 2748, 1686, 1588, 1510, 1264, 1156, 1130, 1080, 980, 922, 732.

Proton nuclear magnetic resonance spectrum ($\delta$ ppm in CDCl$_3$): 3.53 (3H, s), 3.95 (3H, s), 5.32 (2H, s), 7.27 (1H, d, J = 8.3 Hz), 7.43 (1H, dd, J = 2.0, 8.3 Hz), 7.44 (1H, d, J = 2.0 Hz), 9.87 (1H, s).

Mass spectrum: M/Z (%) 197 (33), 196 (M$^+$, 100), 166 (99), 165 (58), 151 (28), 150 (28), 119 (30), 105 (28), 95 (21), 79 (35), 77 (51), 65 (26), 63 (27), 51 (52), 45 (91).

Production Example 18

In 400 ml of acetone were dissolved and suspended 19.9 g of syringylaldehyde and 80.5 g of potassium carbonate, and chloromethyl methyl ether was further added and the mixture was refluxed for 1 hour. The reaction liquid was filtered and the filtrate was concentrated under a reduced pressure, and the obtained syrup was subjected to the column chromatography [230–400 mesh Kieselgel; eluting solvent = hexane/ethyl acetate (3/1)] to obtain 22.5 g (yield = 91.3%) of 3,5-dimethoxy-4-methoxymethoxybenzaldehyde.

Melting point: 52.0° to 53.0° C.

Infrared absorption spectrum $v_{max}^{KBr}$ cm$^{-1}$: 3060, 2992, 2964, 2940, 2840, 1688, 1594, 1502, 1470, 1444, 1422, 1386, 1322, 1234, 1156, 1142, 1126, 1084, 960, 920, 838.

Proton nuclear magnetic resonance spectrum ($\delta$ ppm in acetone-d$_6$): 3.59 (3H, s), 3.92 (6H, s), 5.22 (2H, s), 7.13 (2H, s), 9.87 (1H, s), Mass spectrum: M/Z (%) 227 (3), 226 (M$^+$, 26), 197 (4), 196 (31), 195 (4), 182 (10), 181 (12), 180 (4), 169 (3), 167 (3), 135 (4), 125 (4), 95 (4), 93 (4), 79 (3), 65 (4), 51 (4), 46 (5), 45 (100).

Production Example 19

In 200 ml of anhydrous dimethylformamide was dissolved 30.0 g of p-hydroxybenzaldehyde, and 40.9 g of anhydrous potassium carbonate was added to the solution and the mixture was stirred at room temperature for 30 minutes. Then, 46.3 g of benzyl bromide was dropped into the mixture and a reaction was carried out at room temperature with stirring overnight. After the reaction, the reaction mixture was extracted with diethyl ether, and the solvent was removed from the extract by distillation. The obtained residue was recrystallized from a mixed solvent of diethyl ether and n-hexane to obtain 48.2 g (yield = 92.3%) of p-benzyloxybenzaldehyde in the form of a colorless prism.

Melting point: 69.0° to 70.0° C.

Infrared absorption spectrum $v_{max}^{KBr}$ cm$^{-1}$: 2824, 2800, 2744, 1680, 1602, 1574, 1510, 1462, 1452, 1426, 1394, 1320, 1302, 1260, 1214, 1164, 1110, 1076, 1030, 1018, 866, 830, 734, 694, 656, 514.

Proton nuclear magnetic resonance spectrum ($\delta$ ppm in CDCl$_3$): 5.14 (2H, s), 7.07 (2H, d, J = 8.8 Hz), 7.40 (5H, m), 7.83 (2H, d, J = 8.8 Hz), 9.88 (1H, s).

Mass spectrum: M/Z (%) 212 (M$^+$, 6) 92 (9), 91 (100), 65 (22), 63 (7), 51 (6).

Production Example 20

In 320 ml of dimethylformamide was dissolved 3.2 g of vaniline, and 44.8 g of N,N-diisopropylethylamine was added to the solution and the mixture was stirred. The liquid mixture was cooled to 0° C. and 18.1 ml of chloromethyl methyl ether was added to the liquid mixture. The temperature was elevated to room temperature and the mixture was stirred for 5 hours. After the reaction, a large quantity of water was added to the reaction mixture, and the mixture was extracted with diethyl ether and the solvent was removed from the extract by distillation. The obtained residue was allowed to stand under ice cooling, and the obtained solid was washed with petroleum ether and recovered by filtration to obtain 34.0 g (yield = 83%) of intended 3-methoxy-4-methoxymethoxybenzaldehyde.

Production Example 21

In 100 ml of dimethylformamide was dissolved 10 g of isovaniline, and 14 ml of N,N-diisopropylethylamine was added to the solution and the mixture was stirred. The liquid mixture was cooled to 0° C. and 7.2 ml of chloromethyl methyl ether was added to the mixture, and the temperature was elevated to room temperature and the mixture was stirred for 5 hours. After the reaction, a large quantity of water was added to the reaction mixture, and the mixture was extracted with diethyl ether, washed with water and dried. Removal of the solvent by distillation gave 11.0 g (yield=85%) of 4-methoxy-3-methoxymethoxybenzaldehyde in the form of a yellow oil.

Production Example 22

In 50 ml of dimethylformamide was dissolved 5.0 g of syringylaldehyde, and 7.0 ml of N,N-diisopropylethylamine was added to the solution and the mixture was stirred. The liquid mixture was cooled to 0° C., 3.1 ml of chloromethyl methyl ether was added to the liquid mixture, and the mixture was stirred for 3.5 hours. After the reaction, a large quantity of water was added to the reaction mixture, and the mixture was extracted with ether, washed with water and dried. Removal of the solvent by distillation gave 4.6 g (yield =75%) of 3,5-dimethoxy-4-methoxymethoxybenzaldehyde in the form of a yellow oil.

Production Example 23

In 40 ml of anhydrous dimethylformamide were dissolved 2.4 g of p-hydroxybenzaldehyde and 5.0 g of triethylamine, and 3.2 g of chloromethyl methyl ether was dropped in the solution and the mixture was stirred under ice cooling for 1 hour and at room temperature for 3 hours to effect a reaction. After the reaction, the reaction mixture was extracted with 400 ml of ethyl acetate, and the solvent was removed from the extract by distillation to quantitatively obtain 53.5 g of p-methoxymethoxybenzaldehyde in the form of a yellow oil.

Infrared absorption spectrum $\nu_{max}^{KBr}$ cm$^{-1}$: 2956, 2900, 2828, 1696, 1600, 1580, 1510, 1444, 1428, 1394, 1316, 1244, 1214, 1202, 1150, 1108, 1082, 988, 922, 834, 754, 594.

Proton nuclear magnetic resonance spectrum ($\delta$ ppm in CDCl$_3$): 3.48 (3H, s), 5.25 (2H, s), 7.14 (2H, d, J=8.8 Hz), 7.83 (2H, d, J=8.8 Hz), 9.89 (1H, s).

Mass spectrum: M/Z (%) 166 (M$^+$, 13), 135 (11), 122 (27), 121 (31), 93 (16), 83 (16), 72 (41), 65 (13), 46 (100).

Production Example 24

In 200 ml of dimethylformamide was dissolved 32.66 g of 3,4-dihydroxybenzaldehyde, and the solution was cooled to −5° C. and 200 ml of N,N-diisopropylethylamine was added to the solution. Then, 70 ml of chloromethyl methyl ether was gradually added to the mixture, and the mixture was stirred overnight to effect reaction. After the reaction, the reaction mixture was poured into ice water, and the mixture was extracted with ethyl acetate three times. The organic layer was washed with water three times and shaken with a saturated aqueous solution of sodium chloride, and the organic layer was dried with anhydrous sodium sulfate and filtered. The solvent was removed from the filtrate by distillation, and the obtained residue was recrystallized from ethyl acetate to obtain 41.20 g (yield=86.37%) of 3,4-bis(methoxymethoxy)benzaldehyde.

Infrared absorption spectrum $\nu_{max}^{nujol}$ cm$^{-1}$: 2956, 2904, 2828, 1694, 1598, 1500, 1434, 1260, 1152, 1126, 1076, 984.

Proton nuclear magnetic resonance spectrum ($\delta$ ppm in CDCl$_3$): 3.52 (6H, s), 5.29 (2H, s), 5.32 (2H, s), 7.28 (1H, d, J=8.3 Hz), 7.50 (1H, dd, J=8.3, 1.5 Hz), 7.67 (1H, d, J=1.5 Hz), 9.85 (1H, s).

Mass spectrum: M/Z (%) 226 (M$^+$, 6), 166 (5), 150 (11), 149 (5), 134 (3), 58 (19), 45 (100), 43 (52).

Production Example 25

In 40 ml of anhydrous dimethylformamide were dissolved 2.44 g of p-hydroxybenzaldehyde and 5.06 g of triethylamine, and 3.22 g of chloromethyl methyl ether was gradually dropped into the solution under ice cooling over a period of 10 minutes and the mixture was stirred for 1 hour under ice cooling. The temperature was elevated to room temperature and the mixture was stirred for 3 hours to effect a reaction. After the reaction, the reaction mixture was extracted with ethyl acetate (400 ml) and the ethyl acetate layer was washed with water (200 ml×4 times), shaken with a saturated aqueous solution of sodium chloride (100 ml×2 times), dried with anhydrous sodium sulfate and filtered. The solvent was removed from the filtrate by distillation to quantitatively obtain 3.31 g of p-methoxymethoxybenzaldehyde in the form of a yellow oil.

Infrared absorption spectrum $\nu_{max}^{KBr}$ cm$^{-1}$: 2956, 2900, 2828, 1696, 1600, 1580, 1510, 1444, 1428, 1394, 1316, 1244, 1214, 1202, 1150, 1108, 1082, 988, 922, 834, 754, 594.

Proton nuclear magnetic resonance spectrum ($\delta$ ppm in CDCl$_3$): 3.48 (3H, s), 5.25 (2H, s), 7.14 (2H, d, J=8.8 Hz), 7.83 (2H, d, J=8.8 Hz), 9.89 (1H, s).

Mass spectrum: M/Z (%) 166 (M$^+$, 13), 135 (11), 122 (27), 121 (31), 93 (16), 83 (16), 72 (41), 65 (13), 46 (100).

Production Example 26

To 61.2 g of p-hydroxybenzaldehyde and 208 g of potassium carbonate was added 300 ml of tetrahydrofuran, and the mixture was stirred at room temperature for 1 hour. Then, 66.0 ml of 1-chloro-3-methyl-2-butene was dropped into the mixture, and the mixture was stirred for 3 days. After the reaction, the reaction liquid was poured into ice water and extracted with ether, the ether layer was washed with a 10% solution of potassium carbonate, and the organic layer was shaken with a 5% solution of sodium hydroxide. The pH value of the aqueous layer was adjusted to about 2 by 6N hydrochloric acid and the formed precipitate was extracted with ether. The ether layer was washed with a saturated aqueous solution of sodium hydrogencarbonate, water and a saturated aqueous solution of sodium chloride in sequence, dried with anhydrous sodium sulfate and filtered. The solvent was removed from the filtrate by distillation and the obtained residue was subjected to the column chromatography (330 g of 240-400 mesh silica gel; hexane/ethyl acetate =3/1; 0.4 kg/cm$^2$). Fractions of 50 ml were recovered in sequence, and the 19th to 51st fractions were combined to obtain 12.31 g (yield=13.05%) of 4-hydroxy-3-(3-methyl-2-butenyl)-benzaldehyde.

Infrared absorption spectrum $\nu_{max}^{KBr}$ cm$^{-1}$: 3268, 2968, 2916, 2852, 2744, 1668, 1588, 1504, 1438, 1378, 1282, 1250, 1158, 1108, 1092, 824, 634.

Proton nuclear magnetic resonance spectrum ($\delta$ ppm in acetone-d$_6$): 1.74 (6H, d, J=1.5 Hz), 3.38 (2H, d, J=7.8 Hz), 5.37 (1H, tm, J=7.3, 1.5 Hz), 7.02 (1H, d, J=8.3 Hz), 7.63 (1H, dd, J=8.3, 2.0 Hz), 7.68 (1H, d, J=2.0 Hz), 9.82 (1H, s).

Mass spectrum: M/Z (%) 190 (M$^+$, 74), 161 (27), 147 (59), 135 (100), 107 (27), 91 (32), 77 (27), 43 (49).

Then, 7.0 g of the so-obtained 4-hydroxy-3-(3-methyl-2-butenyl)benzaldehyde was dissolved in770 ml of tetrahydrofuran, and 19.25 g of N,N-diisopropylethylamine was added to the solution and the mixture was stirred at room temperature for 1 hour. After the reaction, the reaction liquid was cooled to 0° C. and 7.0 ml of chloromethyl methyl ether was dropped into the reaction liquid, and the mixture was stirred at room temperature overnight. Then, the reaction liquid was poured into ice water, and the organic layer was extracted with ether, washed with water, dried with anhydrous sodium sulfate, and filtered. The obtained residue was subjected to the column chromatography (260 g of 200–400 mesh Kieselgel 60, hexane/ethyl acetate=6/1, 0.4 kg/cm$^2$), fractions of 50 ml were recovered in sequence, and the 14th to 24th fractions were combined to obtain 7.85 g (yield=91.1%) of 4-methoxymethoxy-3-(3-methyl-2-butenyl)benzaldehyde in the form of a colorless liquid.

Infrared absorption spectrum $\nu_{max}^{KBr}$ cm$^{-1}$: 2960, 2912, 2852, 2824, 2728, 1690, 1600, 1582, 1494, 1442, 1378, 1326, 1246, 1204, 1152, 1112, 1080, 988, 924, 848.

Proton nuclear magnetic resonance spectrum ($\delta$ ppm in CDCl$_3$): 1.73 (3H, s), 1.75 (3H, s), 3.38 (2H, d, J=7.8 Hz), 3.49 (3H, s), 5.29 (2H, s), 5.30 (1H, m), 7.16 (1H, d, J=9.3 Hz), 7.68–7.70 (2H, m), 9.87 (1H, s).

Mass spectrum: M/Z (%) 234 (M$^+$, 11), 202 (100), 189 (29), 188 (22), 187 (70), 173 (86), 161 (46), 159 (67), 147 (35), 135 (24), 119 (24), 91 (45), 77 (23), 45 (86), 43 (23).

Production Example 27

In 80 ml of dimethylformamide was dissolved 12.22 g of p-hydroxybenzaldehyde, and 17.66 g of anhydrous potassium carbonate and 13.0 ml of benzyl bromide were added to the solution and the mixture was stirred at room temperature in a nitrogen current for 1 hour. After the reaction, water was added to the reaction mixture and the formed precipitate was recovered by filtration and recrystallized from a dichloromethane/hexane mixed solvent to obtain 20.07 g (yield=94.6%) of 4-benzyloxybenzaldehyde in the form of a colorless needle.

Infrared absorption spectrum $\nu_{max}^{KBR}$ cm$^{-1}$: 3052, 3032, 2828, 2800, 2744, 1688, 1600, 1576, 1510, 1462, 1454, 1426, 1396, 1320, 1300, 1260, 1214, 1166, 1110, 1020, 866, 832, 734, 696, 656.

Proton nuclear magnetic resonance spectrum ($\delta$ ppm in CDCl$_3$): 5.14 (2H, s), 7.07 (2H, d, J=8.8 Hz), 7.31–7.45 (5H, m), 7.83 (2H, d, J=8.8 Hz), 9.88 (1H, s).

Mass spectrum: M/Z (%) 212 (M$^+$, 39), 92 (64), 91 (100), 65 (95), 63 (19), 51 (18).

Then, the so-obtained compounds of formulae II and III were condensed in the presence of a base.

As the solvent to be used, there can be mentioned alcohols such as methanol, ethanol and propanol, and dimethylsulfoxide. As specific examples of the base, there can be mentioned sodium hydroxide, potassium hydroxide, sodium carbonate, potassium carbonate, sodium methylate and sodium ethylate. The base may be added in the form of a solution in the solvent used. The reaction temperature is preferably about −10° to about 60° C. This reaction is an aldol reaction between the acetyl group at the 1'-position in the compound of the formula II and the formyl group at the 1-position in the compound of the formula III. Accordingly, the reaction is advanced regardless of the kinds of substituents at positions other than the 1'-position and 1-position in the compounds of formulae II and III. After the reaction, the compound of formula I is recovered by an ordinary purification method.

Then, by performing at least one operation selected from reduction, alkylation, acetylation, alkoxycarbonylmethylation, ester hydrolysis and removal of protecting groups, the compound of formula I is obtained. The combination and order of these operations can be appropriately adjusted according to the kind of the intended substance.

The reduction can be accomplished by catalytic reduction. As the solvent to be used for the catalytic reduction, there can be mentioned water and organic solvents such as methanol, ethanol, propanol, ethyl acetate, diethyl ether and dioxane. As the catalyst, there can be mentioned platinum oxide, platinum, nickel, rhodium, ruthenium, palladium and palladium-carbon. The reaction temperature is preferably about −10° to about 60° C. The reaction is sufficiently advanced even under atmospheric pressure, but the reaction can be carried out under an elevated pressure. After the reaction, the compound of formula I is obtained by a customary purification method.

Alkylation can be accomplished by the action of an alkyl halide, a dialkyl sulfate, potassium hydride or sodium hydride in an organic solvent such as acetone, methanol, dimethylformamide or tetrahydrofuran in the presence of a base such as potassium hydroxide, sodium hydroxide, potassium carbonate or sodium carbonate. Especially, methylation is preferably carried out in acetone by using anhydrous potassium carbonate and dimethyl sulfate.

Acetylation is accomplished by the action of acetyl chloride or acetic anhydride in pyridine. When acetic anhydride is used, the intended acetate can be obtained in an especially high yield.

Alkoxycarbonylmethylation is accomplished by the action of a lower alkyl ester of an α-monohalogenoacetic acid in the presence of a base. As the solvent to be used, there can be mentioned organic solvents such as acetone and dimethylformamide, and as the base, there can be mentioned sodium hydroxide, potassium hydroxide, sodium carbonate, potassium carbonate, sodium methylate, sodium ethylate, sodium hydride and potassium hydride. As the lower alkyl ester of the α-monohalogenoacetic acid, there can be used products formed by substituting the hydrogen atom at the α-position of a lower alkyl ester of acetic acid such as methyl acetate, ethyl acetate, propyl acetate, butyl acetate or pentyl acetate. The reaction can be promoted by adding potassium iodide according to need.

The ester hydrolysis can be easily accomplished by using an acid or base. As specific examples of the acid, there can be mentioned hydrochloric acid and sulfuric acid, and as specific examples of the base, there can be mentioned sodium hydroxide, potassium hydroxide, sodium carbonate and potassium carbonate.

The removal of protecting groups can be accomplished by addition of an acid and warming or heating or by reduction. Especially, methoxymethyl and methoxyethoxymethyl groups can be removed by addition of an acid and warming or heating. As specific examples of the acid, there can be mentioned hydrochloric acid, sulfuric acid and Lewis acids such as zinc bromide and titanium chloride. Alcohols such as methanol and ethanol are preferably used as the solvent. Zinc bromide or titanium chloride is especially preferred for removal of the methoxyethoxymethyl group.

Furthermore, benzyl, p-nitrobenzyl, 2,4-dinitrobenzyl, o-nitrobenzyl and p-bromobenzyl groups can be removed by the above-mentioned reduction operation.

Specific examples of the production of the compound of formula I will now be described.

Specific Example 1

In 95.0 ml of ethanol were dissolved 14.8 g of the 2'-hydroxy-4',6'-bis(methoxymethoxy)-3'-(3-methyl-2-butenyl)acetophenone obtained in Production Example 1 and 9.0 g of the 3-methoxy-4-methoxymethoxybenzaldehyde obtained in Production Example 17, the solution was cooled to 0° C., and 138.0 ml of a saturated solution of potassium hydroxide in ethanol was added to the solution. The temperature was elevated to room temperature and the reaction liquid was stirred for 15 hours. The reaction liquid was made acidic by an addition of hydrochloric acid and extracted with diethyl ether. The ether layer was concentrated under a reduced pressure. The reaction mixture was subjected to the column chromatography [230–400 mesh Kieselgel 60; eluting solvent=hexane/ethyl acetate (3/1)] to obtain 13.1 g (yield=57.0%) of 2'-hydroxy-3-methoxy-4,4',6'-tris(methoxymethoxy)-3'-(3-methyl-2-butenyl)-chalcone.

Melting point: 62.5° to 63.5° C.

Infrared absorption spectrum $\nu_{max}^{KBr}$ cm$^{-1}$: 3456, 2988, 2956, 2912, 1632, 1580, 1560, 1510, 1442, 1424, 1262, 1236, 1222, 1168, 1158, 1128, 1082, 1070, 992.

Proton nuclear magnetic resonance spectrum ($\delta$ ppm in CDCl$_3$): 1.64 (3H, s), 1.78 (3H, s), 3.31 (2H, d, J=6.8 Hz), 3.47 (6H, s), 3.56 (3H, s), 3.92 (3H, s), 5.24 (2H, s), 5.32 (2H, s), 5.41 (2H, s), 6.51 (1H, s), 7.16 (1H, d, J=8.3 Hz), 7.28 (1H, dd, J=2.0, 8.3 Hz), 7.37 (1H, d, J=2.0 Hz), 7.76 (1H, d, J=15.6 Hz), 7.98 (1H, d, J=15.6 Hz), 14.02 (1H, s).

Mass spectrum: M/Z (%) 502 (M$^+$, 3), 458 (4), 457 (11), 425 (3), 263 (10), 231 (6), 221 (9), 219 (8), 205 (4), 203 (3), 191 (5), 177 (5), 175 (4), 45 (100).

The so-obtained 2'-hydroxy-3-methoxy-4,4',6'-tris(-methoxymethoxy)-3'-(3-methyl-2-butenyl)chalcone was dissolved in ethyl acetate, and catalytic reduction was carried out by using 3.0 g of 5% palladium/carbon. The reaction liquid was filtered by using Celite and concentrated under a reduced pressure to obtain 12.4 g (yield=93.8%) of 1-[2-hydroxy-4,6-bis(methoxymethoxy)-3-isopentylphenyl]-3-(3-methoxy-4-methoxymethoxyphenyl)-1-propanone in the form of a syrup.

Infrared absorption spectrum $\nu_{max}^{NaCl}$ cm$^{-1}$: 3580, 2952, 2868, 2828, 1738, 1616, 1514, 1466, 1450, 1424, 1408, 1262, 1230, 1204, 1156, 1134, 1076, 1064, 1046, 976.

Proton nuclear magnetic resonance spectrum ($\delta$ ppm in CDCl$_3$): 0.94 (6H, d, J=6.4 Hz), 1.30–1.42 (2H, m), 1.59 (1H, nona-like), 2.60 (1H, dd, J=5.9, 10.7 Hz), 2.60 (1H, t-like), 2.97 (2H, t-like), 3.35 (2H, t-like), 3.47 (3H, s), 3.48 (3H, s), 3.51 (3H, s), 3.86 (3H, s), 5.20 (2H, s), 5.22 (2H, s), 5.23 (2H, s), 6.39 (1H, s), 6.74 (1H, dd, J=2.0, 7.8 Hz), 6.80 (1H, d, J=2.0 Hz), 7.06 (1H, d, J=7.8 Hz), 13.74 (1H, s).

Mass spectrum: M/Z (%) 506 (M$^+$, 8), 474 (9), 267 (27), 223 (17), 179 (11), 165 (9), 164 (9), 151 (17), 137 (9), 55 (9), 45 (100).

Then, 5.0 g of 1-[2-hydroxy-4,6-bis(methoxymethoxy)-3-isopentylphenyl]-3-(3-methoxy-4-methoxymethoxyphenyl)-1-propanone was dissolved in 12.0 ml of methanol, and 37 ml of a hydrochloric acid/methanol reagent was added to the solution and the mixture was refluxed for 1 hour. The reaction liquid was neutralized with a saturated solution of sodium hydrogencarbonate and extracted with diethyl ether. The ether layer was washed with water, dried with anhydrous magnesium sulfate, and concentrated under a reduced pressure. The reaction mixture was subjected to the column chromatography [230–400 mesh Kieselgel 60; eluting solvent=chloroform/methanol (30/1)] to obtain 1.9 g (yield=50.9%) of 1-(2,4,6-trihydroxy-3-isopentylphenyl)-3-(4-hydroxy-3-methoxyphenyl)-1-propane.

Infrared absorption spectrum $\nu_{max}^{KBr}$ cm$^{-1}$: 3504, 3364, 2952, 2864, 1620, 1570, 1516, 1434, 1386, 1366, 1302, 1272, 1254, 1232, 1206, 1146, 1130, 1116, 1066, 1032.

Proton nuclear magnetic resonance spectrum ($\delta$ ppm in CDCl$_3$): 0.93 (6H, d, J=6.8 Hz), 1.36–1.43 (2H, m), 1.58 (1H, nona-like), 2.58 (1H, t, J=7.8 Hz), 2.58 (1H, dd-like), 2.90 (2H, t-like), 3.36 (2H, t-like), 3.82 (3H, s), 6.06 (1H, s), 6.72 (2H, s), 6.88 (1H, s), 7.22 (1H, s), 8.96 (1H, s), 9.46 (1H, s), 13.93 (1H, s).

Mass spectrum: M/Z (%) 375 (9), 374 (M$^+$, 38), 223 (46), 181 (32), 165 (12), 151 (14), 150 (90), 139 (29), 138 (17), 137 (100), 122 (10), 69 (12), 55 (14), 41 (13).

The reaction of Specific Example 1 is illustrated below.

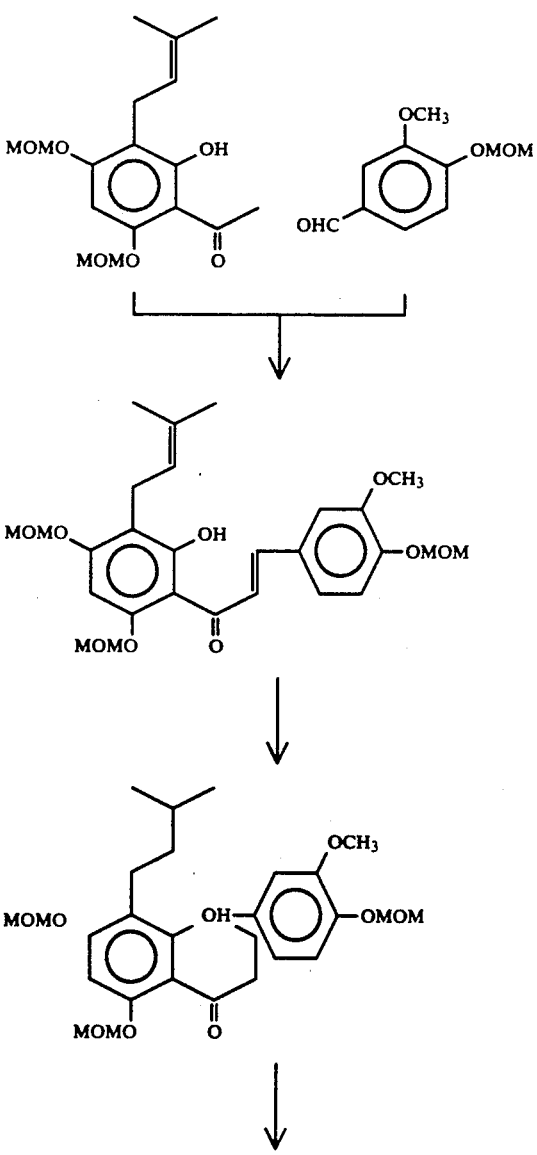

-continued

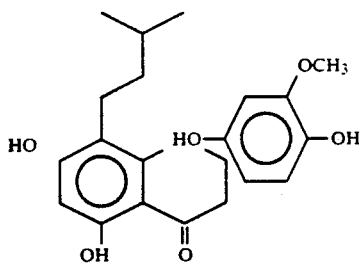

(Note, OMOM stands for a methoxymethoxy group, and will be used hereinafter.)

Specific Example 2

In 600 ml of ethanol were dissolved 22.9 g of the 2'-hydroxy4',6'-bis(methoxymethoxy)-3'-(3-methyl-2-butenyl)acetophenone obtained in Reproduction Example 1 and 17.2 g of the 3,5-dimethoxy-4-methoxymethoxybenzaldehyde obtained in production Example 18, and 200 ml of a saturated solution of potassium hydroxide in ethanol was added to the solution and the mixture was stirred for 3 days. The reaction solution was neutralized with 6N hydrochloric acid, and the precipitated crystal was recovered by filtration, washed with water, and dried to obtain 21.2 g (yield=56.4%) of 2'-hydroxy-3,5-dimethoxy-4,4',6'-tris(methoxymethoxy)3'-(3-methyl-2-butenyl)chalcone.

Melting point: 91.2° to 92.0° C.

Infrared absorption spectrum $\nu_{max}^{KBr}$ cm$^{-1}$: 3788, 3736, 2992, 2952, 1624, 1582, 1562, 1422, 1278, 1256, 1246, 1226, 1134, 1066, 1106, 968, 920.

Proton nuclear magnetic resonance spectrum (δ ppm in acetone-d$_6$): 1.64 (3H, s), 1.78 (3H, s), 3.31 (2H, d, J=7.3 Hz), 3.47 (3H, s), 3.54 (3H, s), 3.56 (3H, s), 3.91 (6H, s), 5.22 (1H, md, J=7.3 Hz), 5.08 (2H, s), 5.32 (2H, s), 5.41 (2H, s), 6.51 (1H, s), 7.06 (2H, s), 7.73 (1H, d, J=15.6 Hz), 8.00 (1H, d, J=15.6 Hz), 13.95 (1H, s).

Mass spectrum: M/Z (%) 533 (3) 532 (8), 488 (4), 487 (9), 402 (4), 295 (3), 263 (8), 251 (5), 231 (7), 221 (4), 219 (7), 211 (3), 209 (4), 207 (5), 205 (6), 192 (3), 191 (4), 179 (4), 177 (3), 165 (3), 69 (4), 45 (100).

Then, 26.9 g of 2'-hydroxy-3,5-dimethoxy-4,4',6'-tris(methoxymethoxy)-3'-(3-methyl-2-butenyl)chalcone was dissolved in 400 ml of ethyl acetate, and catalytic reduction was carried out by using 5% palladium/carbon. The reaction liquid was filtered through Celite to obtain 26.7 g (yield=98.5%) of 1-[2-hydroxy-4,6-bis(-methoxymethoxy)-3-isopentylphenyl]-3-(3,5-dimethoxy-4-methoxymethoxyphenyl)-1-propanone.

Infrared absorption spectrum $\nu_{max}^{neat}$ cm$^{-1}$: 3536, 2952, 2836, 1618, 1594, 1506, 1462, 1424, 1284, 1232, 1204, 1156, 1130, 1080, 1064, 974.

Proton nuclear magnetic resonance spectrum (δ ppm in CDCl$_3$): 0.94 (6H, d, J=6.3 Hz), 1.19-1.43 (2H, m), 1.57 (1H, m), 2.61 (1H, dd-like), 2.61 (1H, t, J=7.8 Hz), 2.95 (1H, t-like), 3.44 (1H, t-like), 3.47 (3H, s), 3.48 (3H, s), 3.51 (3H, s), 3.80 (6H, s), 4.97 (2H, s), 5.29 (2H, s), 5.33 (2H, s), 6.47 (1H, s), 6.59 (2H, s), 13.85 (1H, s).

Mass spectrum: M/Z (%) 537 (2), 536 (M+, 8), 297 (6), 268 (4), 267 (24), 254 (3), 253 (22), 252 (5), 237 (7), 223 (5), 221 (10), 220 (5) 209 (6), 207 (6), 193 (6), 181 (7), 180 (4), 179 (10), 178 (5), 177 (9), 167 (7), 165 (8), 151 (3), 55 (3), 45 (100).

Next, 10.0 g of 1-[2-hydroxy-4,6-bis(methoxymethoxy)-3-isopentylphenyl]-3-(3,5-dimethoxy-4-methoxymethoxyphenyl)-1-propanone was dissolved in 25.0 ml of methanol, and 70 ml of a hydrochloric acid-methanol reagent was added to the solution and the mixture was refluxed in an argon atmosphere for 1 hour. The reaction liquid was concentrated under a reduced pressure and subjected to the column chromatography [230–400 mesh Kieselgel 60; eluting solvent=chloroform/methanol (20/1)] to obtain 2.7 g (yield=36.8%) of yellowish brown 1-(2,4,6-trihydroxy-3-isopentylphenyl)-3-(4-hydroxy-3,5-dimethoxyphenyl)-1-propanone.

Melting point: 166.0° to 167.0° C.

Infrared absorption spectrum $\nu_{max}^{KBr}$ cm$^{-1}$: 3408, 2948, 2864, 1622, 1518, 1430, 1366, 1310, 1284, 1238, 1212, 1140, 1116.

Proton nuclear magnetic resonance spectrum (δ ppm in acetone-d$_6$): 0.93 (6H, d, J=6.8 Hz), 1.13-1.43 (2H, m), 1.58 (1H, m), 2.58 (1H, t, J=7.8 Hz), 2.58 (1H, dd-like), 2.90 (2H, t-like), 3.37 (2H, t-like), 3.80 (6H, s), 6.06 (1H, s), 6.56 (2H, s), 6.86 (1H, br.), 13.92 (1H, s).

Mass spectrum: M/Z (%) 405 (12), 404 (M+, 51), 355 (16), 329 (5), 224 (5), 223 (35), 209 (11), 182 (11), 181 (54), 180 (65), 173 (8), 168 (12), 167 (100), 166 (5), 165 (13), 149 (14), 139 (9), 138 (6), 123 (6), 69 (6), 55 (5).

The reaction of Specific Example 2 is illustrated below.

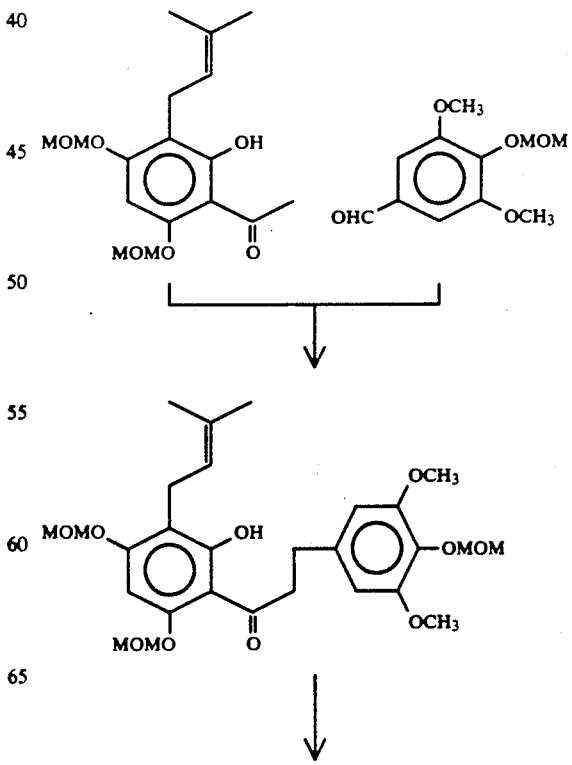

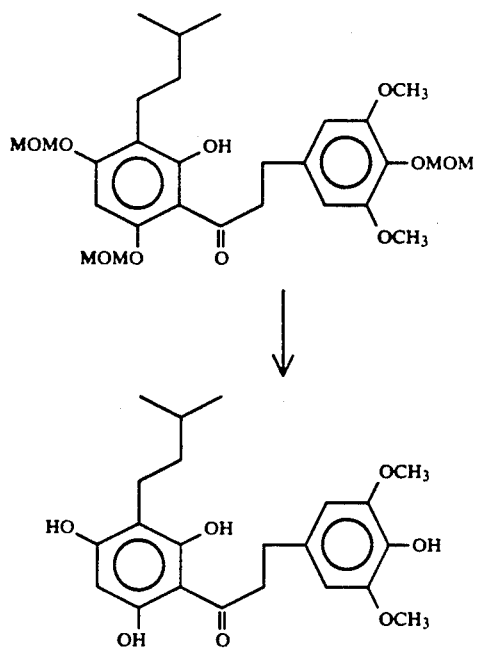

Specific Example 3

In 5 ml of ethanol were dissolved 0.4 g of the 2'-hydroxy-4'-methoxy-3'-(3-methyl-2-butenyl)acetophenone obtained in Production Example 2 and 0.3 ml of p-anisaldehyde, and the solution was cooled to 0° C. and 7.5 ml of a saturated solution of potassium hydroxide in ethanol was added to the solution. In a nitrogen current, the mixture was stirred at 0° C. for 30 minutes and at room temperature for 4 days. After the reaction, hydrochloric acid was added to the reaction liquid under cooling and the reaction liquid was gradually made acidic, and the formed precipitate was recovered by filtration and recrystallized from methanol to obtain 0.4 g (yield=64.7%) of 2'-hydroxy-4,4'-dimethoxy3'-(3-methyl-2-butenyl)chalcone in the form of a yellow needle.

Melting point: 97.0° to 97.5° C.

Infrared absorption spectrum $\nu_{max}^{KBr}$ cm$^{-1}$: 3440, 3000, 2972, 2916, 2848, 1634, 1606, 1574, 1514, 1494, 1462, 1444, 1416, 1372, 1322, 1310, 1294, 1282, 1262, 1238, 1194, 1174, 1116, 1096, 1070, 1022, 978, 832, 810, 794, 626.

Protron nuclear magnetic resonance spectrum (δ ppm in CDCl$_3$): 1.68 (3H, d, J=1.5 Hz), 1.80 (3H, d, J=1.5 Hz), 3.39 (2H, d, J=6.8 Hz), 3.85 (3H, s), 3.90 (3H, s), 5.23 (1H, t, septet, Jt=6.8 Hz, Js=1.5 Hz), 6.49 (1H, d, J=8.8 Hz), 6.93 (2H, d, J=8.8 Hz), 7.47 (1H, d, J=15.6 Hz), 7.79 (1H, d, J=8.8 Hz), 7.85 (1H, d, J=15.6 Hz), 13.47 (1H, s).

Mass spectrum: M/Z (%) 352 (M+, 76), 310 (21), 309 (100), 297 (35), 203 (25), 190 (21), 175 (32), 163 (92), 161 (43), 133 (20)

To 20 ml of an ethyl acetate suspension of 0.3 g of 5% palladiumcarbon, in which hydrogen had been adsorbed in advance, was added 1.0 g of the so-obtained 2'-hydroxy-4,4'-dimethoxy-3'-(3-methyl-2-butenyl)chalcone, and the mixture was stirred at room temperature for 5 hours and hydrogen was absorbed. After the reaction, the suspension was filtered to remove the palladium-carbon, and removal of the solvent by distillation gave 1.0 g (yield=98.7%) of 1-(2-hydroxy-3-isopentyl-4-methoxyphenyl)-3-(4-methoxyphenyl)-1-propanone in the form of a colorless solid.

Melting point: 77° to 78° C.

Infrared absorption spectrum $\nu_{max}^{KBr}$ cm$^{-1}$: 3440, 2964, 2948, 1624, 1584, 1514, 1498, 1460, 1436, 1418, 1384, 1368, 1344, 1314, 1304, 1274, 1252, 1222, 1190, 1176, 1134, 1098, 1066, 1040, 832, 798, 786, 626.

Protron nuclear magnetic resonance spectrum (δ ppm in CDCl$_3$): 0.94 (6H, d, J=6.4 Hz), 1.36 (2H, m), 1.59 (1H, m), 2.64 (1H, dd, J=6.4, 7.8 Hz), 2.64 (1H, t, J=8.3 Hz), 2.99 (1H, dd, J=6.4, 7.8 Hz), 2.99 (1H, t, J=7.8 Hz), 3.21 (1H, dd, J=6.4, 7.8 Hz), 3.21 (1H, t, J=7.8 Hz), 3.78 (3H, s), 3.87 (3H, s) 6.42 (1H, d, J=8.8 Hz), 6.84 (2H, d, J=8.8 Hz), 7.16 (2H, d, J=8.8 Hz), 7.60 (1H, d, J=8.8 Hz), 12.78 (1H, s).

Mass spectrum: M/Z (%) 356 (M+, 21), 300 (10), 221 (38), 179 (10), 134 (37), 121 (100).

Then, 21.5 g of 1-(2-hydroxy-4-methoxy-3-isopentylphenyl)-3-(4-methoxyphenyl)-1-propanone was dissolved in 150 ml of anhydrous acetone, and 41.6 g of anhydrous potassium carbonate was added to the solution and the mixture was stirred for 30 minutes. Then, 18.4 g of methyl α-bromoacetate was added to the reaction mixture, and the mixture was stirred at room temperature for 5 days to effect reaction After the reaction, the reaction mixture was extracted with diethyl ether and the solvent was removed from the extract, and the obtained residue was subjected to the silica gel chromatography (eluting solvent: n-hexane/ethyl acetate =8/1) to obtain 20.9 g (yield=80.9%) of 1-(4-methoxy-2-methoxycarbonylmethoxy-3-isopentylphenyl -3-(4-methoxyphenyl)-1-propanone in the form of a colorless oil.

Infrared absorption spectrum $\nu_{max}^{KBr}$ cm$^{-1}$: 2952, 2864, 1764, 1742, 1680, 1612, 1590, 1512, 1482, 1466, 1440, 1424, 1366, 1248, 1202, 1180, 1130, 1084, 1034, 812.

Protron nuclear magnetic resonance spectrum (δ ppm in CDCl$_3$): 0.94 (6H, d, J=6.6 Hz), 1.39 (2H, m), 1.61 (1H, m), 2.65 (1H, dd, J=10.8, 4.9 Hz), 2.65 (1H, t, J=8.1 Hz), 2.94 (1H, dd, J=7.8, 7.1 Hz), 2.94 (1H, t, J=7.8 Hz), 3.22 (1H, t, J=7.8 Hz), 3.22 (1H, dd, J=7.8, 7.1 Hz), 3.77 (3H, s), 3.78 (3H, s), 3.85 (3H, s), 4.40 (2H, s), 6.66 (1H, d, J=8.6 Hz), 6.80 (2H, d, J=8.6 Hz), 7.13 (2H, d, J=8.6 Hz), 7.43 (1H, d, J=8.6 Hz).

Mass spectrum: M/Z (%) 428 (M+, 19), 293 (39), 221 (11), 209 (22), 163 (9), 163 (9), 134 (28), 122 (10), 121 (100), 91 (11), 45 (9).

Then, 14.2 g of 1-(4-methoxy-2-methoxycarbonylmethoxy-3-isopentylphenyl)-3-(4-methoxyphenyl)-1-propanone was dissolved in 80 ml of methanol, and 100 ml of a 5% aqueous solution of potassium hydroxide was added to the solution and the mixture was stirred at room temperature for 30 minutes. After the reaction, the reaction mixture was made acidic by dilute hydrochloric acid and extracted with diethyl ether. The solvent was removed from the diethyl ether layer by distillation to obtain 13.1 g (yield=95.3%) of 1-(carboxymethoxy-4-methoxy-3-isopentylphenyl)-3-(4-methoxyphenyl)-1-propanone in the form of a colorless oil.

Infrared absorption spectrum $\nu_{max}^{KBr}$ cm$^{-1}$: 3416, 2952, 2864, 1752, 1662, 1612, 1590, 1512, 1484, 1464, 1424, 1384, 1366, 1246, 1204, 1178, 1128, 1100, 1084, 1066, 1034, 812.

Protron nuclear magnetic resonance spectrum (δ ppm in acetone-d6): 0.91 (6H, d, J=6.6 Hz), 1.36 (2H, m), 1.57 (1H, m), 2.67 (2H, m), 2.86 (2H, t, J=7.3 Hz), 3.25 (2H, t, J=7.3 Hz), 3.72 (3H, s), 3.88 (3H, s), 4.32 (2H, s), 6.78 (3H, d, J=8.6 Hz), 7.13 (2H, d, J=8.6 Hz), 7.57 (1H, d, J=8.6 Hz).

Mass spectrum:

M/Z (%) 414 (M+, 17), 279 (31), 233 (11), 221 (27), 195 (21), 165 (12), 135 (12), 134 (44), 122 (11), 121 (100), 91 (14), 77 (14).

The reaction of Specific Example 3 is illustrated below.

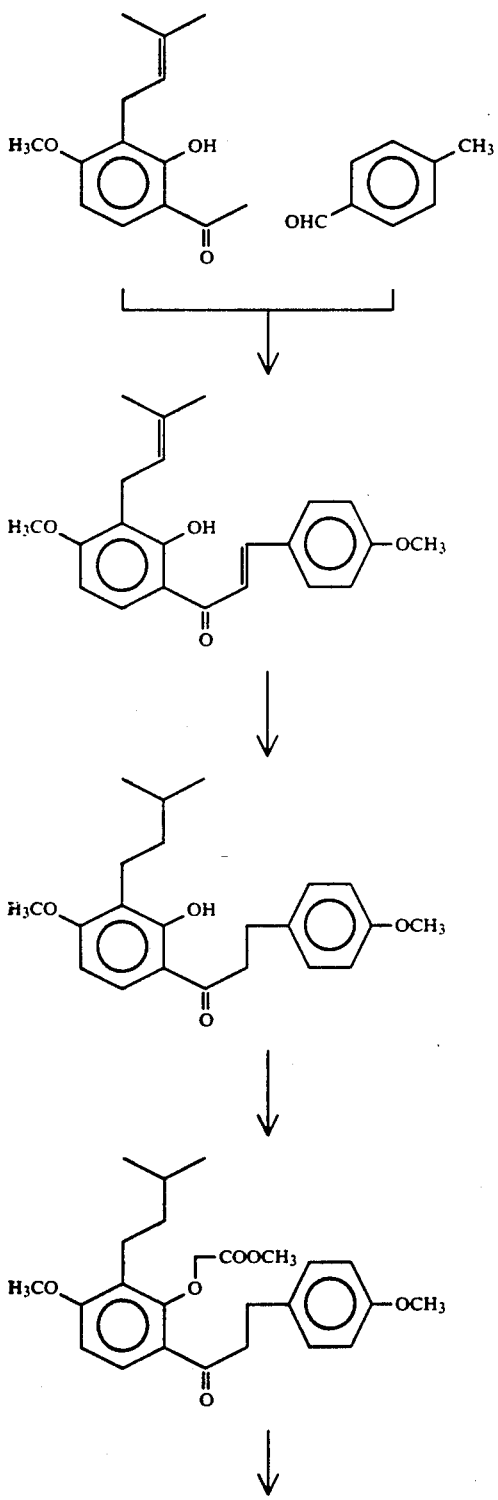

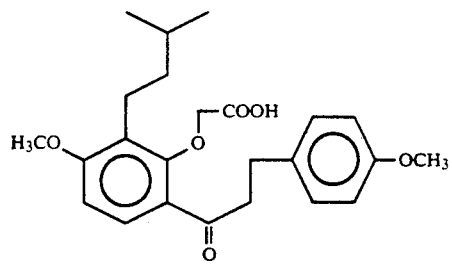

Specific Example 4

In a mixed solvent of 50 ml of ethanol and 100 ml of dimethylsulfoxide were dissolved 28.7 g of the 2'-hydroxy-4'-methoxy-3'-(3-methyl-2-butenyl)acetophenone obtained in Production Example 2 and 28.6 g of the benzyloxybenzaldehyde obtained in Production Example 19, and the solution was cooled to 0° C. and a saturated solution of potassium hydroxide in ethanol was added to the solution. The mixture was stirred at room temperature in a nitrogen current for 3 hours to effect a reaction. After the reaction, the reaction mixture was neutralized with dilute hydrochloric acid and extracted with ethyl acetate, the solvent was removed from the ethyl acetate layer by distillation, and the obtained residue was crystallized from methanol to obtain 47.6 g (yield=90.3%) of 25 4-benzyloxy-2'-hydroxy-4'-methoxy-3'-(3-methyl-2-butenyl)chalcone in the form of a yellow prism.

Melting point: 70° to 71° C.

Infrared absorption spectrum $\nu_{max}^{KBr}$ cm$^{-1}$: 2912, 1632, 1602, 1582, 1562, 1506, 1494, 1460, 1416, 1380, 1360, 1318, 1300, 1288, 1240, 1192, 1168, 1120, 1096, 1074, 1020, 984, 862, 840, 622.

Proton nuclear magnetic resonance spectrum (δ ppm in CDCl$_3$): 1.67 (3H, s), 1.79 (3H, s), 3.38 (2H, d, J=6.8 Hz), 3.86 (3H, s), 5.07 (2H, s), 5.24 (1H, t, J=6.8 Hz), 6.45 (1H, d, J=8.8 Hz), 6.98 (2H, d, J=8.8 Hz), 7.31-7.43 (5H, m), 7.43 (1H, d, J=15.6 Hz), 7.56 (2H, d, J=8.8 Hz), 7.75 (1H, d, J=8.8 Hz), 7.81 (1H, d, J=15.6 Hz). 13.48 (1H, s, eliminated by addition of D Mass spectrum: M/Z (%) 428 (M+, 20), 385 (18), 373 (68), 163 (19), 92 (9), 91 (100), 65 (9).

Then, an ethyl acetate solution of 24.5 g of 4-benzyloxy-2'-hydroxy-4'-methoxy-3'-(3-methyl-2-butenyl)-chalcone was added to an ethyl acetate suspension of 5% palladium-carbon, which a hydrogen gas had been sufficiently absorbed in advance, and the mixture was stirred at room temperature in a hydrogen atmosphere for 3.5 hours. After the reaction, the reaction mixture was filtered and the solvent was removed by distillation, and the obtained residue was subjected to the silica gel column chromatography (eluting solvent: n-hexane/ethyl acetate=5/1) to obtain 17.2 g of 1-(2-hydroxy-4-methoxy-3-isopentylphenyl)-3-(4-hydroxyphenyl)-1-propanone in the form of a colorless oil.

Infrared absorption spectrum $\nu_{max}^{KBr}$ cm$^{-1}$: 3416, 2952, 1626, 1514, 1500, 1444, 1418, 1366, 1284, 1260, 1228, 1192, 1132, 1064.

Protron nuclear magnetic resonance spectrum (δ ppm in CDCl$_3$): 0.94 (6H, d, J=6.8 Hz), 1.26-1.42 (2H, m), 2.64 (2H, m), 2.97 (2H, t, J=7.8 Hz), 3.20 (2H, t, J=7.8 Hz), 3.87 (3H, s), 5.00 (1H, s, disappeared by addition of D$_2$O) 6.42 (1H, d, J=8.8 Hz), 6.76 (2H, d, J=8.3 Hz), 7.10 (2H, d, J=8.3 Hz), 7.59 (1H, d, J=8.8 Hz), 12.77 (1H, s, eliminated by addition of D₂O).

Mass spectrum: M/Z (%) 342 (M⁻, 52), 286 (29), 285 (23), 221 (100), 194 (19), 180 (18), 179 (51), 165 (21), 120 (30), 107 (81).

Then, 32.3 g of 1-(2-hydroxy-4-methoxy-3-isopentylphenyl)-3-(4-hydroxyphenyl)-1-propanone was dissolved in 150 ml of anhydrous acetone, 32.6 g of anhydrous potassium carbonate was added to the solution, and the mixture was stirred for 30 minutes. Then, 17.3 g of methyl α-bromoacetate was added to the reaction mixture, and the mixture was stirred at room temperature for 1 day to effect a reaction. After the reaction, the reaction mixture was neutralized with dilute hydrochloric acid and extracted with ethyl acetate, and the solvent was removed from the extract by distillation to obtain 37.0 g (yield=94.6%) of 1-(2-hydroxy-4-methoxy-3-isopentylphenyl)-3-(4-methoxycarbonylmethoxyphenyl)-1-propanone in the form of a colorless prism.

Infrared absorption spectrum $\nu_{max}^{KBr}$ cm⁻¹: 2948, 2904, 2860, 1776, 1736, 1628, 1586, 1516, 1500, 1460, 1434, 1418, 1386, 1370, 1316, 1300, 1290, 1274, 1242, 1222, 1184, 1132, 1098, 1082, 1064, 1042, 1012, 834, 794, 628.

Protron nuclear magnetic resonance spectrum (δ ppm in CDCl₃): 0.94 (6H, d, J=6.8 Hz), 1.31-1.42 (2H, m), 1.52-1.59 (1H, m), 2.64 (2H, t, J=7.8 Hz), 3.02 (2H, t, J=7.8 Hz), 3.20 (2H, t, J=7.8 Hz), 3.80 (3H, s), 3.86 (3H, s), 4.61 (2H, s), 6.41 (1H, d, J=9.3 Hz), 6.84 (2H, d, J=8.8 Hz), 7.16 (2H, d, J=8.8 Hz), 7.58 (1H, d, J=9.3 Hz). 12.76 (1H, s, eliminated by addition of D₂O).

Mass spectrum: M/Z (%) 414 (M⁺, 27), 358 (14), 357 (12), 221 (65), 192 (43), 180 (11), 179 (100), 165 (15), 121 (14), 46 (15), Then, 20.6 g of 1-(2-hydroxy-4-methoxy-3-isopentylphenyl)-3-(4-methoxycarbonylmethoxyphenyl)-1-propanone was dissolved in 100 ml of methanol, and 100 ml of a 5% aqueous solution of potassium hydroxide was added to the solution and the mixture was stirred at room temperature for 1 hour. After the reaction, the reaction mixture was made acidic by dilute hydrochloric acid, and the formed precipitate was recovered by filtration and recrystallized from benzene to obtain 15.2 g (yield=96.8%) of 1-(2-hydroxy-4-methoxy-3-isopentylphenyl)-3-(4-carboxymethoxyphenyl)-1-propanone in the form of a colorless grain.

Melting point: 193° to 194° C.

Infrared absorption spectrum $\nu_{max}^{KBr}$ cm⁻¹: 3416, 2948, 2864, 1696, 1632, 1514, 1500, 1462, 1420, 1384, 1366, 1320, 1276, 1226, 1188, 1134, 1100, 1064, 918, 884, 826, 790, 706.

Protron nuclear magnetic resonance spectrum (δ ppm in acetone-d₆+CD₃OD): 0.93 (6H, d, J=6.4 Hz), 1.35 (2H, m), 1.55 (1H, m), 2.63 (2H, m), 2.96 (2H, t, J=7.8 Hz), 3.30 (2H, t, J=7.8 Hz), 3.91 (3H, s), 4.48 (2H, s), 6.62 (1H, d, J=8.8 Hz), 6.87 (2H, d, J=8.8 Hz), 7.20 (2H, d, J=8.8 Hz), 7.84 (1H, d, J=8.8 Hz).

Mass spectrum: M/Z (%) 400 (M⁺, 27), 344 (13), 343 (16), 221 (70), 179 (18), 178 (33), 165 (100), 107 (50).

The reaction of Specific Example 4 is illustrated below.

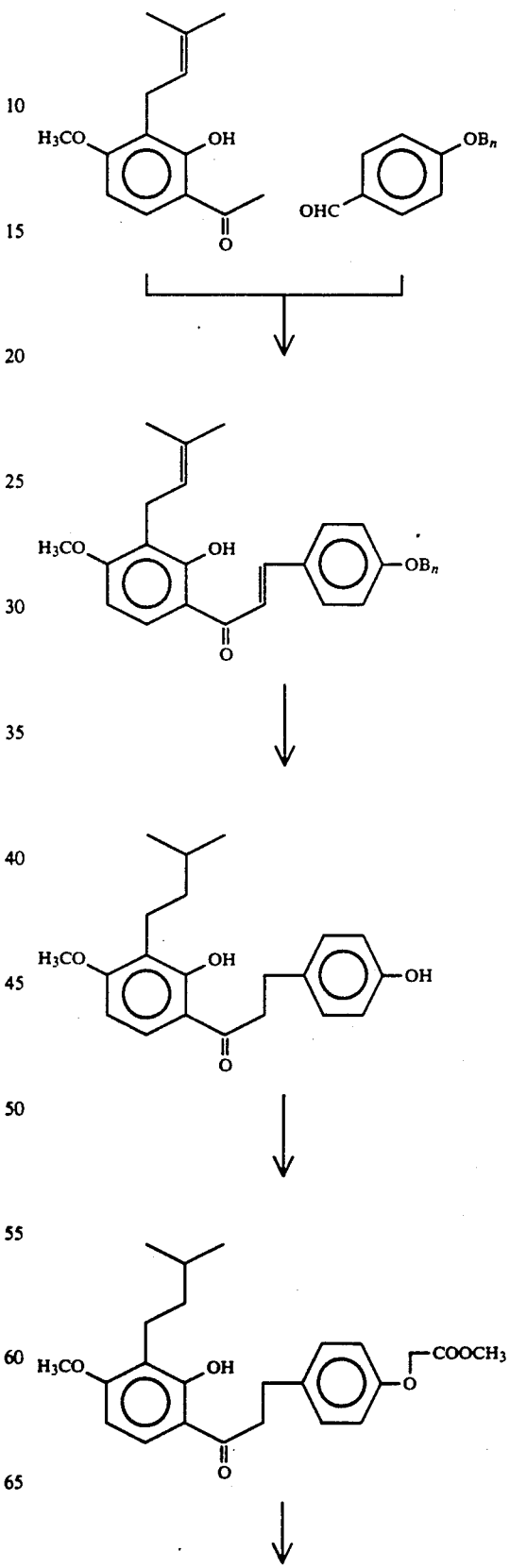

-continued

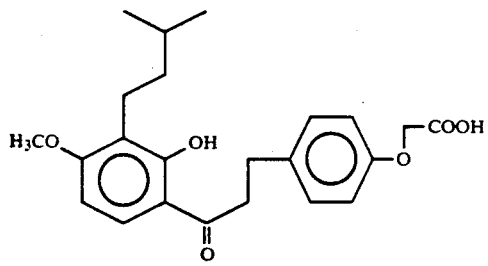

(Note, Bn stands for a benzyl group, and this will be used hereinafter.)

Specific Example 5

A mixture of 9.0 g of the 2'-hydroxy-4',6'-dimethoxy-3'-(3-methyl-2-butenyl)acetophenone obtained in Production Example 3 and 10.4 g of the 3-methoxy-4-methoxymethoxybenzaldehyde obtained in Production Example 20 was suspended in 150 ml of ethanol, and a saturated solution of potassium hydroxide in ethanol was added to the suspension and the mixture was stirred at room temperature overnight. The reaction mixture was neutralized by addition of dilute hydrochloric acid under cooling. The precipitated solid was recovered by filtration and crystallized from ethyl acetate/hexane to obtain 2'-hydroxy-3,4',6'-trimethoxy-4-methoxymethoxy-3'-(3-methyl-2-butenyl)chalcone in the form of a reddish orange cube in a yield of 53%.

Melting point: 125.5° to 127° C.

Infrared absorption spectrum $\nu_{max}^{KBr}$ cm$^{-1}$: 2908, 1626, 1586, 1560, 1504, 1466, 1422, 1316, 1258, 1222, 1204, 1158, 1134, 1120, 1090, 976.

Protron nuclear magnetic resonance spectrum ($\delta$ ppm in CDCl$_3$): 1.67 (3H, s), 1.78 (3H,s), 3.29 (2H, d, J=7.1 Hz), 3.52 (3H, s), 3.90 (3H, s), 3.93 (6H, s), 5.20 (1H, m, J=1.0, 7.1 Hz), 5.27 (2H, s), 5.99 (1H, s), 7.12 (1H, brs, J=2 Hz), 7.15 (1H, dd, J=1.4, 9.5 Hz), 7.15 (1H, d, J=9.5 Hz), 7.70 (1H, d, J=15.6 Hz), 7.79 (1H, d, J=15.4 Hz).

Mass spectrum: M/Z (%) 442 (M+, 63), 399 (43), 387 (19), 313 (10), 293 (31), 261 (17), 284 (17), 193 (78), 45 (100).

An ethyl acetate solution of 7.0 g of the so-obtained 2'-hydroxy-3,4',6'-trimethoxy-4-methoxymethoxy3'-(3-methyl-2-butenyl)chalcone was added to an ethyl acetate solution of 1.0 g of 5% palladium/carbon, in which hydrogen had been adsorbed in advance, and the mixture was strongly stirred and hydrogen was adsorbed. Then, the mixture was stirred overnight, the palladium/carbon was removed by using Celite and the solvent was removed by distillation. The residue was dissolved in diethyl ether and crystallization was effected by addition of hexane to obtain 6.2 g (yield= 92%) of 1-(2-hydroxy-4,6-dimethoxy-3-isopentylphenyl)3-(3-methoxy-4-methoxymethoxyphenyl)-1-propanone in the form of a white solid.

Melting point: 69° to 70° C.

Infrared absorption spectrum $\nu_{max}^{KBr}$ cm$^{-1}$: 2948, 1612, 1592, 1514, 1472, 1462, 1412, 1300, 1272, 1260, 1212, 1156, 1142, 1084, 1000.

Protron nuclear magnetic resonance spectrum ($\delta$ ppm in CDCl$_3$): 0.93 (6H, d, J=6.4 Hz), 1.27-1.39 (1H, m), 1.40-1.60 (1H, m), 2.52-2.60 (2H, m), 2.94-2.98 (2H, m), 3.26-3.33 (2H, m), 3.52 (3H, s), 3.87 (3H, s), 3.88 (6H, s), 5.20 (2H, s), 5.95 (1H, s), 6.75 (1H, dd, J=2.2, 8.1 Hz), 6.80 (1H, d, J=2.0 Hz), 7.06 (1H, d, J=8.1 Hz).

Mass spectrum: M/Z (%) 446 (M+, 38), 251 (39), 237 (87), 194 (21), 151 (15), 45 (100).

Then, 10 ml of dimethylformamide was dropped into a mixture of 2.0 g of 1-(2-hydroxy-4,6-dimethoxy-3-isopentylphenyl)-3-(3-methoxy-4-methoxymethoxyphenyl)-1-propanone and 0.2 g of sodium hydride, and the mixture was stirred for 60 minutes. Then, 0.5 ml of methyl α-bromoacetate was added to the mixture at 0° C., and the mixture was stirred for 45 minutes. After the reaction, the solvent was removed from the reaction liquid mixture by distillation, and the residue was dried under reduced pressure to obtain substantially quantitatively 1-(4,6-dimethoxy-2-methoxycarbonylmethoxy-3-isopentylphenyl)-3-(3-methoxy-4-methoxymethoxyphenyl)-1-propanone in the form of a colorless transparent oil.

Protron nuclear magnetic resonance spectrum ($\delta$ ppm in CDCl$_3$): 0.92 (6H, d, J=6.6 Hz), 1.42-1.2 (2H, m), 1.50-1.70 (1H, m), 2.48-2.60 (2H, m), 2.90-2.93 (2H, m), 3.06-3.20 (2H, m), 3.50 (3H, s), 3.77 (3H, s), 3.79 (3H, s), 3.84 (3H, s), 3.86 (3H, s), 4.44 (2H, s), 5.18 (2H, s), 6.26 (1H, s), 6.72 (1H, d), 6.77 (1H., dd), 7.03 (1H, d).

Then, 15.5 g of 1-(4,6-dimethoxy-2-methoxycarbonylmethoxy-3-isopentylphenyl)-3-(3-methoxy-4-methoxymethoxyphenyl)-1-propanone was dissolved in 25 ml of methanol, and 23 ml of hydrochloric acid/methanol was added to the solution and the mixture was heated and fluxed for 10 minutes. After the reaction, the solvent was removed by distillation, and the obtained solid was dissolved in a small amount of ethyl acetate and crystallized by diethyl ether/hexane to obtain 11.9 g (yield=84%) of 1-(4,6-dimethoxy-2-methoxycarbonylmethoxy-3-isopentylphenyl)-3-(4-hydroxy-3-methoxyphenyl)-1-propanone in the form of a white solid.

Melting point: 89° to 90° C.

Infrared absorption spectrum $\nu_{max}^{KBr}$ cm$^{-1}$: 3500, 2952, 1768, 1692, 1604, 1516, 1466, 1452, 1266, 1204, 1136, 1102.

Protron nuclear magnetic resonance spectrum ($\delta$ ppm in CDCl$_3$): 0.92 (6H, d, J=6.6 Hz), 1.30-1.40 (2H, m), 1.50-1.70 (1H, m), 2.48-2.56 (2H, m), 2.88-2.96 (2H, m), 3.06-3.15 (2H, m), 3.77 (3H, s), 3.78 (3H, s), 3.84 (3H, s), 4.41 (2H, s), 5.5 (1H, brs), 6.26 (1H, s), 6.70 (1H, dd, J=2.0, 8.1 Hz), 6.75 (1H, d, J=1.7 Hz), 6.81 (1H, d, J=8.1 Hz).

Mass spectrum: M/Z (%) 474 (M+, 27), 442 (15), 385 (36), 323 (82), 296 (100), 239 (87), 193 (35), 150 (50), 137 (86), 45 (45).

Then, 12.0 g of 1-(4,6-dimethoxy-2-methoxycarbonylmethoxy-3-isopentylphenyl)-3-(4-hydroxy-3-methoxyphenyl)-1-propanone was dissolved in 120 ml of methanol, and 70 ml of a 5% aqueous solution of potassium hydroxide was added to the solution and the mixture was stirred at room temperature for 20 minutes. Then, the reaction mixture was made weakly acidic by addition of dilute hydrochloric acid, and the solvent was removed by distillation and the residue was crystallized from ethyl acetate/diethyl ether/hexane to obtain 9.7 g (yield=of 1-(2-carboxymethoxy-4,6-dimethoxy-3-isopentylphenyl)-3-(4-hydroxy-3-methoxyphenyl)-1-propanone in the form of a white solid.

Melting point: 87° to 88° C.

Infrared absorption spectrum $\nu_{max}^{KBr}$ cm$^{-1}$: 3480, 3432, 2952, 1738, 1698, 1516, 1270, 1140, 1128.

Protron nuclear magnetic resonance spectrum (δ ppm in CDCl₃): 0.92 (6H, d, J=6.6 Hz), 1.30–1.40 (2H, m). 1.50–1.70 (1H, m), 2.46–2.54 (2H, m) 2.91–2.95 (2H, m), 3.10–3.17 (2H, m), 3.80 (3H, s), 3.85 (6H, s), 4.44 (2H, s), 6.27 (1H, s), 6.67 (1H, dd, J=1.7, 8.1 Hz), 6.73 (1H, d, J=1.7 Hz), 6.80 (1H, d, J=8.1 Hz).

Mass spectrum: M/Z (%) 460 (M⁺, 8), 385 (26), 309 (34), 282 (49), 225 (93), 193 (41), 150 (93), 137 (100).

The reaction of Specific Example 5 is illustrated below.

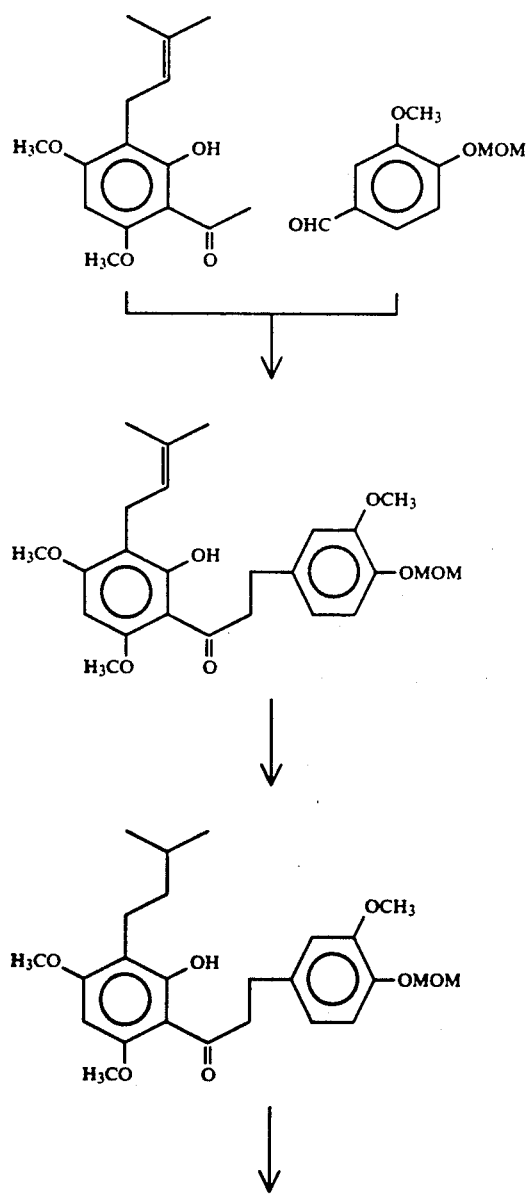

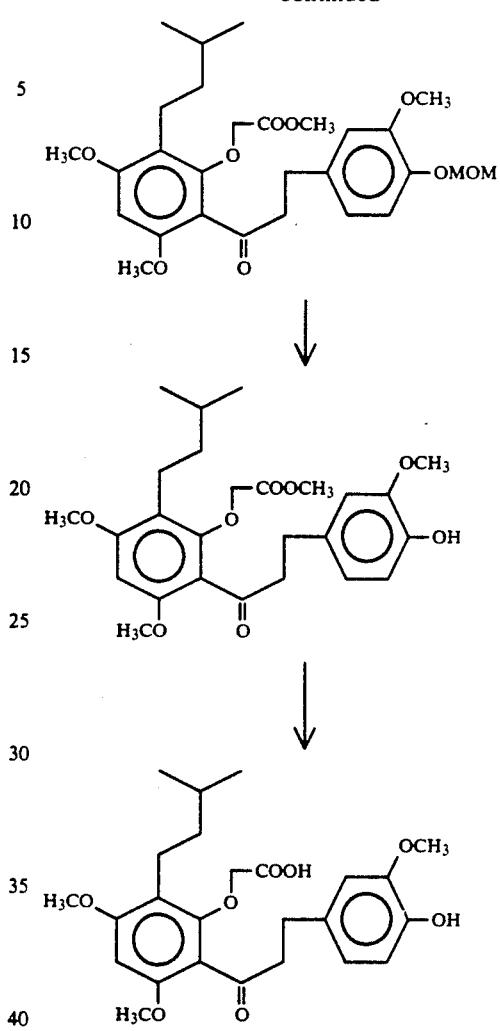

Specific Example 6

A mixture of 16.0 g of the 2'-hydroxy-4',6'-dimethoxy-3'-(3-methyl-2-butenyl)acetophenone obtained in Production Example 3 and 17.8 g of the 4-methoxy-3-methoxymethoxybenzaldehyde obtained in Production Example 21 was suspended in 150 ml of ethanol, and 110 ml of a saturated ethanol solution of potassium hydroxide was added to the suspension and the mixture was stirred at room temperature overnight. The reaction liquid mixture was neutralized by addition of dilute hydrochloric acid under cooling. The precipitated solid was recovered by filtration and crystallized from ethyl acetate/hexane to obtain 21.7 g (yield=63%) of 2'-hydroxy-4,4',6'-trimethoxy-3-methoxymethoxy-3'-(3-methyl-2-butenyl)chalcone in the form of a reddish orange scale.

Melting point: 115.5° to 117° C.

Infrared absorption spectrum $\nu_{max}^{KBr}$ cm⁻¹: 3016, 2952, 1760, 1694, 1600, 1260, 1216, 1134, 762.

Protron nuclear magnetic resonance spectrum (δ ppm in CDCl₃): 1.67 (3H, d, J=1.2 Hz), 1.78 (3H, s), 3.29 (2H, d, J=6.8 Hz), 3.54 (3H, s), 3.90 (3H, s), 3.92 (3H, s), 3.94 (3H, s), 5.20 (1H, m), 5.27 (2H, s), 5.99 (1H, s), 6.90 (1H, d, J=8.6 Hz), 7.5 (1H, d=2.2 Hz), 7.70 (1H, d, J=15.4 Hz), 7.81 (1H, d, J=15.6 Hz).

Mass spectrum: M/Z (%) 442 (M−, 37), 399 (28), 233 (31), 193 (63), 45 (100).

To 40 ml of an ethyl acetate solution of 0.7 g of 5% palladium/carbon, in which hydrogen had been adsorbed in advance, was added 160 ml of an ethyl acetate solution of 5.0 g of the so-obtained 2'-hydroxy-4',6'-trimethoxy-3-methoxymethoxy-3'-(3-methyl-2-butenyl)chalcone, and hydrogen was further adsorbed with strong stirring. Then the mixture was stirred overnight, and the palladium/carbon was removed by using Celite and the solvent was removed by distillation. The residue was dissolved in diethyl ether and crystallized by addition of hexane to obtain 4.4 g (yield=91%) of 1-(2-hydroxy-4,6-dimethoxy-3-isopentylphenyl)-3-(4-methoxy-3-methoxymethoxyphenyl)-1-propanone in the form of a white solid.

Melting point: 93.5° to 94.5° C.

Infrared adsorption spectrum $\nu_{max}^{KBr}$ cm$^{-1}$: 2956, 1634, 1590, 1508, 1470, 1426, 1280, 1264, 1228, 1214, 1140, 978, 924.

Protron nuclear magnetic resonance spectrum (δ ppm in CDCl$_3$): 0.93 (6H, d, J=6.6 Hz), 1.38–1.31 (2H, m), 1.60–1.50 (1H, m), 2.60–2.52 (2H, m), 2.96–2.88 (2H, m), 3.31–3.24 (2H, m), 3.26 (3H, s), 3.86 (3H, s), 3.87 (3H, s), 3.89 (3H, s), 5.22 (2H, s), 5.95 (1H, s), 6.82 (1H, d, J=8.3 Hz), 6.85 (1H, dd), 7.06 (1H, d).

Mass spectrum: M/Z (%) 446 (M+, 34), 401 (26), 251 (88), 237 (100), 180 (35), 137 (36), 45 (90).

Then, 20 ml of dimethylformamide was dropped into a mixture of 1-(2-hydroxy-4,6-dimethoxy-3-isopentylphenyl)-3-(4-methoxy-3-methoxymethoxyphenyl)-1-propanone and 0.4 g of sodium hydride at 0° C., and the mixture was stirred for 30 minutes. Then, 1.0 ml of methyl α-bromoacetate was added to the mixture at 0° C. and the mixture was stirred for 30 minutes. After the reaction, the solvent was removed from the reaction liquid mixture by distillation and the residue was dried under a reduced pressure to obtain substantially quantitatively 1-(4,6-dimethoxy-2-methoxycarbonylmethoxy-3-isopentylphenyl)-3-(4-methoxy-3-methoxymethoxyphenyl)-1-propanone in the form of a colorless transparent oil.

Infrared absorption spectrum $\nu_{max}^{NaCl}$ cm$^{-1}$: 3016, 2952, 1760, 1600, 1514, 1466, 1260, 1216, 1134, 1094, 1000.

Protron nuclear magnetic resonance spectrum (δ ppm in CDCl$_3$): 0.92 (6H, d, J=6.6 Hz), 1.22–1.40 (2H, m), 1.50–1.70 (1H, m), 2.48–2.56 (2H, m), 2.88–2.96 (2H, m), 3.06–3.14 (2H, m), 3.51 (3H, s), 3.78 (3H, s), 3.79 (3H, s), 3.84 (6H, s), 5.21 (2H, s), 6.26 (1H, s), 6.79 (1H, d, J=8.1 Hz), 6.86 (1H, dd, J=2.0, 8.3 Hz), 7.02 (1H, d, J=1.7 Hz).

Mass spectrum: M/Z (%) 518 (M+, 20), 323 (34), 309 (60), 296 (27), 239 (36), 194 (25), 137 (20), 45 (100).

Then, 1-(4,6-dimethoxy-2-methoxycarbonylmethoxy-3-isopentylphenyl)-3-(4-methoxy-3-methoxymethoxyphenyl)-1-propanone was dissolved in 7.5 ml of methanol, and 7.5 ml of hydrochloride acid/methanol was added to the solution and the mixture was heated and refluxed. After the reaction, the solvent was removed from the reaction mixture by distillation and the obtained residue was dissolved in a small amount of ethyl acetate and crystallized from ether/hexane to obtain 3.5 g (yield=of 1-(4,6-dimethoxy-2-methoxycarbonylmethoxy-3-isopentylphenyl)-3-(3-hydroxy-4-methoxyphenyl)-1-propanone in the form of a colorless transparent rectangular crystal.

Melting point: 94° to 95° C.

Infrared absorption spectrum $\nu_{max}^{KBr}$ cm$^{-1}$: 3472, 2952, 1744, 1694, 1600, 1512, 1278, 1234, 1200, 1138.

Proton nuclear magnetic resonance spectrum (δ ppm in CDCl$_3$): 0.92 (6H, d, J=6.6 Hz), 1.28–1.40 (2H, m), 1.57 (1H, m), 2.47–2.56 (2H, m), 2.85–2.94 (2H, m), 3.04–3.13 (2H, m), 3.78 (3H, s), 3.80 (3H, s), 3.84 (3H, s), 3.85 (3H, s), 4.45 (2H, s), 5.64 (1H, s), 6.26 (1H, s), 6.69 (1H, dd, J=2.0, 8.3 Hz), 6.75 (1H, d, J=7.8 Hz), 6.80 (1H, d, J=1.7 Hz).

Mass spectrum: M/Z (%) 474 (M+, 37), 456 (24), 443 (25), 385 (45), 323 (100), 296 (78), 239 (73), 137 (57).

Then, 3.0 g of 1-(4,6-dimethoxy-2-methoxycarbonylmethoxy-3-isopentylphenyl)-3-(3-hydroxy-4-methoxyphenyl)-1-propanone was dissolved in 30 ml of methanol, and 18 ml of a 5% aqueous solution of potassium hydroxide was added to the solution and the mixture was stirred at room temperature for 20 minutes. Then, the reaction mixture was made weakly acidic by an addition of dilute hydrochloric acid, the solvent was removed from the mixture by distillation, and the residue was crystallized from ethyl acetate/diethyl ether/hexane to obtain 2.6 g (yield=90%) of 1-(2-carboxymethoxy-4,6-dimethoxy-3-isopentylphenyl)-3-(3-hydroxy-4-methoxyphenyl)-1-propanone in the form of a colorless transparent plate.

Melting point: 129° to 130° C.

Infrared absorption spectrum $\nu_{max}^{KBr}$ cm$^{-1}$: 3500, 3420, 2952, 1730, 1680, 1600, 1514, 1258, 1236, 1128.

Protron nuclear magnetic resonance spectrum (δ ppm in CDCl$_3$): 0.95 (6H, d, J=6.6 Hz), 1.26–1.40 (2H, m), 1.50–1.70 (1H, m), 2.45–2.53 (2H, m), 2.85–2.93 (2H, m), 3.82 (3H, s), 3.84 (3H, s), 3.85 (3H, s), 4.43 (2H, s), 6.27 (1H, s), 6.68 (1H, dd, J=2.0, 8.1 Hz), 6.74 (1H, d, J=7.8 Hz), 6.77 (1H, d, J=1.7 Hz).

Mass spectrum: M/Z (%) 460 (M+, 36), 385 (46), 309 (100), 289 (90), 225 (86), 137 (74).

The reaction of Specific Example 6 is illustrated below.

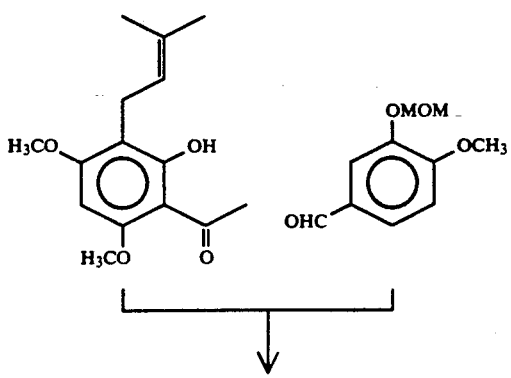

-continued

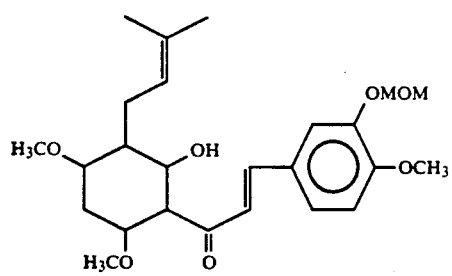

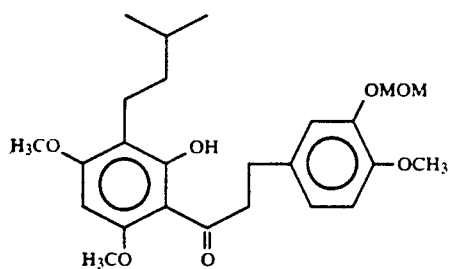

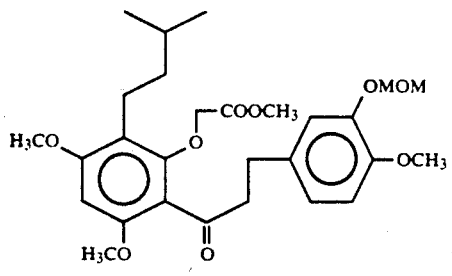

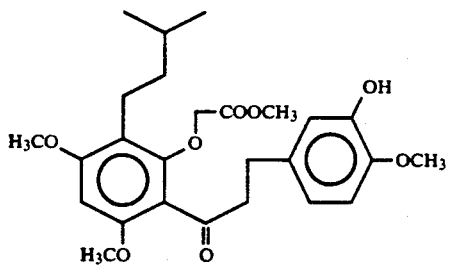

-continued

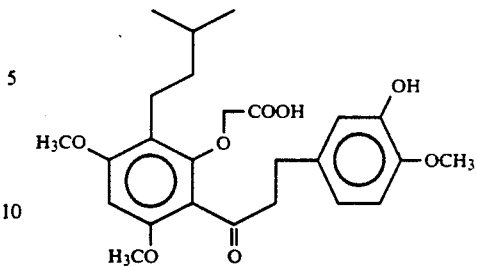

Specific Example 7

A mixture of 15.3 g of the 2'-hydroxy-4',6'-dimethoxy-3'-(3-methyl-2-butenyl)acetophenone obtained in Production Example 3 and 20.7 g of the 3,5-dimethoxy4-methoxymethoxybenzaldehyde obtained in Production Example 22 was suspended in 150 ml of ethanol, and 110 ml of a saturated solution of potassium hydroxide in ethanol was added to the solution and the mixture was stirred at room temperature overnight. The reaction liquid mixture was neutralized by addition of dilute hydrochloric acid under cooling, and the precipitated solid was recovered by filtration and crystallized from ethyl acetate/hexane to obtain 17.5 g (yield=50%) of 2'-hydroxy-3,5,4',6'-tetramethoxy-4-methoxymethoxy3'-(3-methyl-2-butenyl)chalcone in the form of a reddish orange needle.

Melting point: 127.5° to 129° C.

Infrared absorption spectrum $\nu_{max}^{KBr}$ cm$^{-1}$: 2916, 1628, 1582, 1556, 1504, 1422, 1320, 1276, 1224, 1126, 972.

Protron nuclear magnetic resonance spectrum ( $\delta$ ppm in CDCl$_3$): 1.68 (3H, d, J=1 Hz), 1.78 (3H, brs), 3.30 (2H, d, J=6.6 Hz), 3.61 (3H, s), 3.90 (6H, s), 3.90 (3H, s), 3.93 (3H, s), 5.17 (2H, s), 5.20 (1H, m), 6.0 (1H, s), 6.83 (2H, s), 7.64 (1H, d, J=15.6 Hz), 7.77 (1H, d=15.6 Hz).

Mass spectrum: M/Z (%) 472 (M$^+$, 24), 372 (14), 343 (16), 233 (24), 193 (81), 179 (24), 45 (100).

An ethyl acetate solution of 2.8 g of the so-obtained 2'-hydroxy-3,5,4',6'-tetramethoxy-4-methoxymethoxy-3'-(3-methyl-2-butenyl)chalcone was added to 20 ml of an ethyl acetate solution of 0.4 g of palladium/carbon, in which hydrogen had been adsorbed in advance, and hydrogen was further adsorbed with strong stirring. Then, the mixture was stirred overnight, the palladium/carbon was removed by using Celite, and the residue was dissolved in ether and crystallized from hexane to obtain 2.6 g (yield=94%) of 1-(2-hydroxy-4,6-dimethoxy-3-isopentylphenyl)-3-(3,5-dimethoxy-4-methoxymethoxyphenyl)-1-propanone in the form of a white solid.

Melting point: 104.5° to 106.0° C.

Infrared absorption spectrum $\nu_{max}^{KBr}$ cm$^{-1}$: 2952, 1616, 1590, 1466, 1442, 1284, 1238, 1212, 1162, 1150, 1132, 1094, 1086, 964.

Protron nuclear magnetic resonance spectrum ( $\delta$ ppm in CDCl$_3$): 0.93 (6H, d, J=6.6 Hz), 1.20-1.40 (2H, m), 1.80-2.70 (1H, m), 2.56 (2H, m, J=8.1 Hz), 2.93 (2H, t, J=8.1 Hz), 3.29 (2H, t, J=8.0 Hz), 3.60 (3H, s), 3.83 (6H, s), 3.88 (6H, s), 5.10 (2H, s), 5.95 (1H, s), 6.45 (2H, s).

Mass spectrum: M/Z (%) 476 (M$^+$, 10), 253 (32), 237 (100) 179 (23), 45 (46).

Then, 10 ml of dimethylformamide was dropped into a mixture of 2.3 g of 1-(2-hydroxy-4,6-dimethoxy-3-isopentylphenyl)-3-(3,5-dimethoxy-4-methoxymethoxyphenyl)-1-propanone and 0.2 g of sodium hydride at 0° C., and the mixture was stirred for 45 minutes. Then, 0.5 ml of methyl α-bromoacetate was added to the mixture at 0° C., and the mixture was stirred for 20 minutes. After the reaction, the solvent was removed from the reaction liquid mixture by distillation and the residue was dried under a reduced pressure to obtain substantially quantitatively 1-(4,6-dimethoxy-2-methoxycarbonylmethoxy-3-isopentylphenyl)-3-(3,5-dimethoxy-4-methoxymethoxyphenyl)-1-propanone in the form of a colorless transparent oil.

Protron nuclear magnetic resonance spectrum (δ ppm in CDCl₃): 0.92 (6H, d, J=6.4 Hz), 1.36-1.40 (2H, m), 1.59 (1H, m, J=6.6 Hz), 2.48-2.57 (2H, m), 2.89-2.98 (2H, m), 3.08-3.17 (2H, m), 3.59 (3H, s), 3.76 (3H, s), 3.79 (3H, s), 3.83 (6H, s), 3.84 (3H, s), 4.44 (2H, s), 5.08 (2H, s), 6.26 (1H, s), 6.45 (2H, s).

Mass spectrum: M/Z (%) 548 (M⁺, 23), 323 (23), 309 (69), 220 (21), 180 (12), 45 (100).

Then, 2.8 g of 1-(4,6-dimethoxy-2-methoxycarbonylmethoxy-3-isopentylphenyl)-3-(3,5-dimethoxy-4-methoxymethoxyphenyl)-1-propanone was dissolved in 4 ml of methanol, and 4 ml of hydrochloric acid/methanol was added to the solution and the mixture was heated and refluxed for 10 minutes. After the reaction, the solvent was removed from the reaction mixture by distillation, and the obtained solid was dissolved in a small amount of ethyl acetate and crystallized from diethyl ether/hexane to obtain 1.9 g (yield=75%) of 1-(4,6-dimethoxy-2-methoxycarbonylmethoxy-3-isopentylphenyl)-3-(4-hydroxy-3,5-dimethoxyphenyl)-1-propanone in the form of a cotton-like crystal.

Melting point: 92.5° to 93.5° C.

Infrared absorption spectrum $\nu_{max}^{KBr}$ cm⁻¹: 3544, 2952, 1754, 1686, 1602, 1518, 1462, 1434, 1240, 1214, 1140, 1118, 1100.

Protron nuclear magnetic resonance spectrum (δ ppm in CDCl₃): 0.92 (6H, d, J=6.4 Hz), 1.28-1.40 (2H, m), 1.58 (1H, m), 2.48-2.56 (2H, m), 3.07-3.15 (2H, m), 3.77 (3H, s), 3.78 (3H, s), 3.84 (3H, s), 3.86 (6H, s), 4.40 (2H, s), 5.36 (1H, s), 6.26 (1H, s), 6.46 (2H, s).

Mass spectrum: M/Z (%) 504 (M⁺, 18), 415 (20), 323 (62), 296 (49), 233 (79), 180 (87), 167 (100), Then, 1.5 g of 1-(4,6-dimethoxy-2-methoxycarbonylmethoxy-3-isopentylphenyl)-3-(4-hydroxy-3,5-dimethoxyphenyl)-1-propanone was dissolved in 15 ml of methanol, and 8.6 ml of a 5% solution of potassium hydroxide was added to the solution and the mixture was stirred at room temperature for 20 minutes. Then, the reaction mixture was made weakly acidic by addition of dilute hydrochloric acid, the solvent was removed from the mixture by distillation, and the residue was crystallized from ethyl acetate/diethyl ether/hexane to obtain 1.0 g (yield=68%) of 1-(2-carboxymethoxy-4,6-dimethoxy-3-isopentylphenyl)-3-(4-hydroxy-3,5-dimethoxyphenyl)-1-propanone in the form of a white cotton-like crystal.

Melting point: 97.5° to 98.0° C.

Infrared absorption spectrum $\nu_{max}^{KBr}$ cm⁻¹: 3536, 2952, 1690, 1600, 1462, 1354, 1258, 1218, 1130, 1116.

Protron nuclear magnetic resonance spectrum (δ ppm in CDCl₃): 0.92 (6H, d, J=6.4 Hz), 1.35 (2H, m),1.57 (1H, m), 2.50 (2H, m),2.92 (2H, m), 3.14 (2H, m),3.81 (3H, s), 3.85, 3.86 (6H, s), 4.45 (2H, s), 5.4 (brs), 6.28 (1H, s), 6.43 (2H, s).

Mass spectrum: M/Z (%) 490 (M⁺, 30), 415 (16), 309 (55), 282 (27), 225 (38), 180 (100), 167 (40).

The reaction of Specific Example 7 is illustrated below.

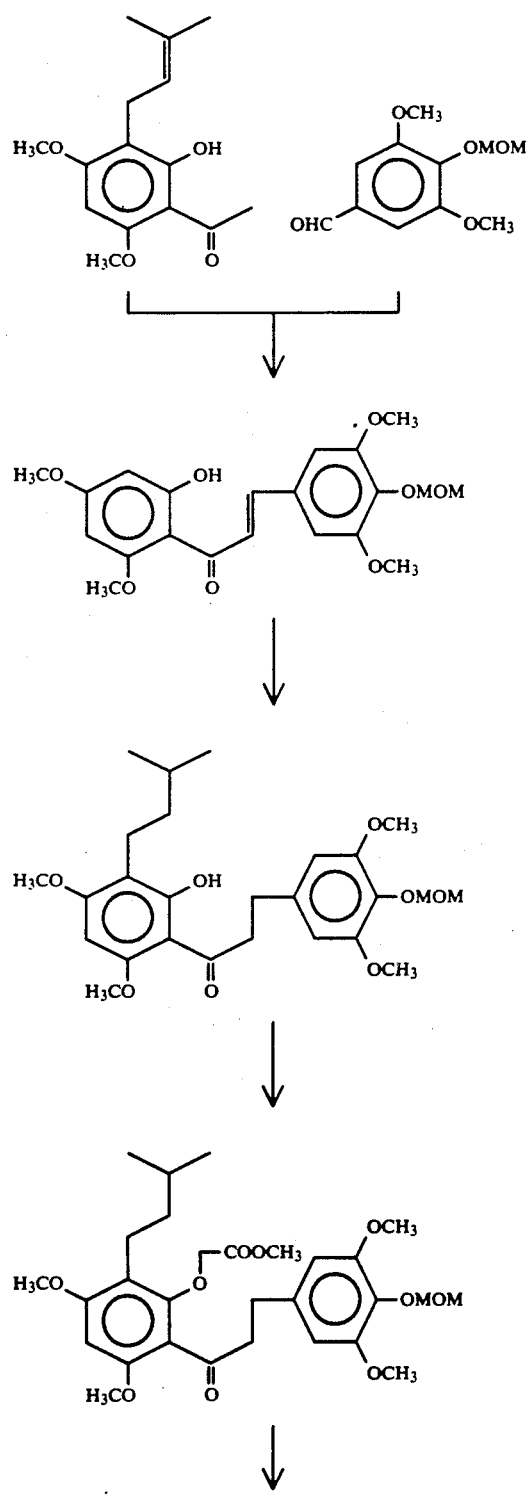

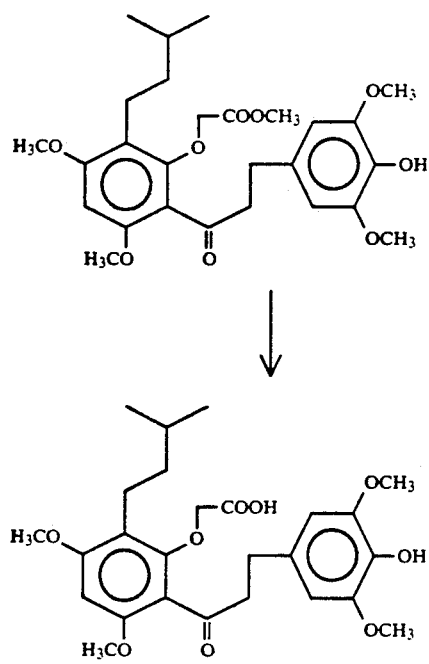

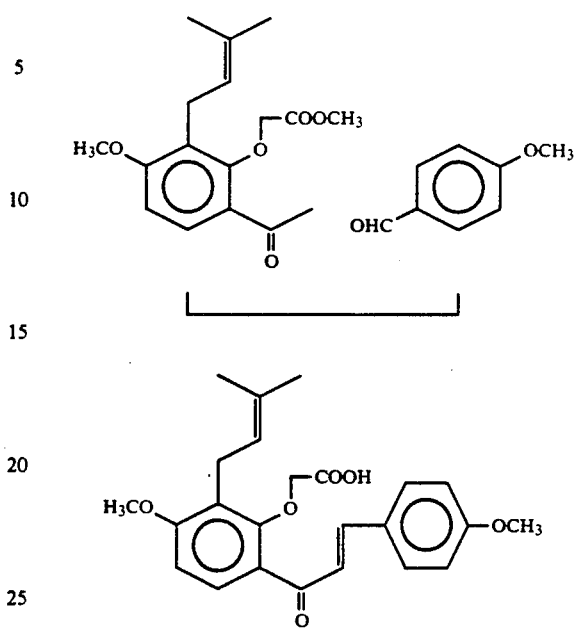

Specific Example 8

In 150 ml of ethanol were dissolved 33.3 g of the 2'-methoxycarbonylmethoxy-4'-methoxy-3'-(3-methyl-2-butenyl)acetophenone obtained in Production Example 4 and 14.8 g of p-ansialdehyde, and 150 ml of a saturated solution of potassium hydroxide in ethanol was added to the solution and the mixture was stirred at room temperature overnight to effect a reaction. After the reaction, the reaction mixture was made acidic by dilute hydrochloric acid, extracted with ethyl acetate and filtered. The solvent was removed from the filtrate by distillation to obtain 2'-carboxymethoxy-4,4'-dimethoxy-3'-(3-methyl-2-butenyl)chalcone.

Infrared absorption spectrum $\nu_{max}^{KBr}$ cm$^{-1}$: 3436, 2916, 1754, 1642, 1592, 1512, 1484, 1462, 1462, 1442, 1424, 1374, 1336, 1304, 1274, 1256, 1238, 1172, 1098, 1028, 830.

Protone nuclear magnetic resonance spectrum ( δ ppm in acetone-d$_6$): 1.66 (3H, d, J=1.2 Hz), 1.77 (3H, d, J=1.0 Hz), 3.48 (2H, d, J=7.1 Hz), 3.85 (3H, s), 3.93 (3H, s), 4.48 (2H, s), 5.21 (1H, m), 6.92 (1H, d, J=8.8 Hz), 6.98 (2H, d, J=8.8 Hz), 7.49 (1H, d, J=15.9 Hz), 7.66 (1H, d, J=15.9 Hz), 7.68 (1H, d, J=8.8 Hz), 7.69 (2H, d, J=8.8 Hz).

Mass spectrum: M/Z (%) 410 (M+, 5), 351 (24), 309 (10), 218 (16), 217 (100), 163 (39), 161 (23), 133 (17), 121 (21), 77 (13).

The reaction of Specific Example 8 is illustrated below.

Specific Example 9

To a liquid mixture of 11.8 g of the 4',6'-dimethoxy-2'-methoxycarbonylmethoxy-3'-isopentylacetophenone obtained in Production Example 5, 4.8 g of p-anisaldehyde and 50 ml of ethanol was added 150 ml of a saturated solution of potassium hydroxide in ethanol, and the mixture was stirred at room temperature overnight to effect a reaction. After the reaction, the reaction mixture was made acidic by dilute hydrochloric acid, extracted with diethyl ether and filtered, and the solvent was removed from the filtrate by distillation. The obtained residue was recrystallized from a mixed solvent of diethyl ether and n-hexane to obtain 12.7 g (yield=81.9%) of 2'-carboxymethoxy-4,4',6'-trimethoxy-3'-isopentylchalcone in the form of a yellow prism.

Melting point: 145° to 146° C.

Infrared absorption spectrum $\nu_{max}^{KBr}$ cm$^{-1}$: 3192, 2952, 1758, 1632, 1602, 1512, 1468, 1422, 1336, 1302, 1280, 1252, 1230, 1202, 1176, 1162, 1130, 1102, 1080.

Protron nuclear magnetic resonance spectrum ( δ ppm in acetone-d$_6$): 0.93 (6H, d, J=6.4 Hz), 1.42 (2H, m), 1.60 (1H, m), 2.64 (2H, m), 3.82 (3H, s), 3.84 (3H, s), 3.93 (3H, s), 4.49 (2H, s), 6.10 (1H, s), 6.91 (1H, d, J=16.1 Hz), 6.97 (2H, d, J=8.8 Hz), 7.33 (1H, d, J=16.1 Hz), 7.60 (2H, d, J=8.8 Hz).

Mass spectrum: M/Z (%) 422 (M+, 30), 397 (38), 385 (29), 194 (28), 193 (100), 161 (34), 133 (20), 121 (44).

The reaction of Specific Example 9 is illustrated below.

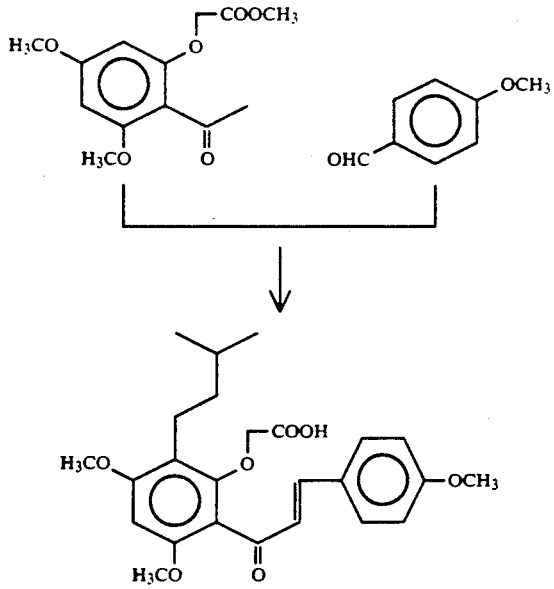

Specific Example 10

In 40 ml of ethanol were dissolved 20.4 g of the 2'-hydroxy-4',6'-bis(methoxymethoxy)-3'-(2-propenyl)acetophenone obtained in Production Example 6 and 13.7 g of the p-methoxymethoxybenzaldehyde obtained in Production Example 23, and a 50% solution of potassium hydroxide in ethanol was added to the solution and the mixture was stirred at room temperature overnight to effect a reaction. After the reaction, the reaction mixture was neutralized with dilute hydrochloric acid and extracted with ethyl acetate, and the solvent was removed from the ethyl acetate layer by distillation. The obtained residue was crystallized from methanol to obtain 26.3 g (yield = 85.9%) of 2'-hydroxy-4,4',6'-tris(-methoxymethoxy)-3'-(2-propenyl)chalcone in the form of a yellow prism.

Melting point: 68° to 69° C.

Infrared absorption spectrum $\nu_{max}^{KBr}$ cm$^{-1}$: 22952, 2904, 1626, 1588, 1558, 1510, 1480, 1426, 1310, 1286, 1228, 1194, 1176, 1150, 1134, 1096, 1074, 1058, 1036, 988, 958, 916, 828.

Protron nuclear magnetic resonance spectrum ($\delta$ ppm in acetone-d$_6$): 2.78 (3H, s), 3.36 (2H, dt, J=6.4, 2.0 Hz), 3.45 (3H, s), 3.47 (3H, s), 3.55 (3H, s), 4.90 (1H, ddt, J=10.3, 2.0, 2.0 Hz), 5.01 (1H, ddt, J=17.1, 2.0, 2.0 Hz), 5.27 (2H, s), 5.32 (2H, s), 5.41 (2H, s), 5.93 (1H, ddt, J=17.1, 10.3, 6.4 Hz), 6.53 (1H, s), 7.11 (2H, d, J=8.8 Hz), 7.70 (2H, d, J=8.8 Hz), 7.78 (1H, d, J=15.1 Hz), 7.99 (1H, d, J=15.1 Hz). 14.05 (1H, s, eliminated by addition of D$_2$O).

Mass spectrum: M/Z (%) 444 (M$^+$, 5), 399 (7), 367 (9), 195 (6), 191 (17), 45 (100).

Then an ethyl acetate solution of 21.1 g of 2'-hydroxy-4,4',6'-tris(methoxymethoxy)-3'-(2-propenyl)-chalcone was added to a suspension of 8.0 g of 5% palladium/carbon in 50 ml of ethyl acetate, in which a hydrogen gas had been sufficiently absorbed, and the mixture was stirred at room temperature in a hydrogen atmosphere for 3 hours. After the reaction, the reaction mixture was filtered and the solvent was removed from the filtrate by distillation to obtain quantitatively 21.2 g of 1-[2-hydroxy-4,6-bis(methoxymethoxy)-3-n-propylphenyl]-3-(4-methoxymethoxyphenyl)-1-propanone in the form of a colorless oil.

Infrared absorption spectrum $\nu_{max}^{KBr}$ cm$^{-1}$: 2956, 2928, 2868, 1616, 1512, 1446, 1424, 1402, 1292, 1234, 1200, 1154, 1132, 1122, 1078, 1056, 1008, 954, 922, 830.

Protron nuclear magnetic resonance spectrum ( $\delta$ ppm in acetone-d$_6$): 0.92 (3H, t, J=7.3 Hz), 1.52 (2H, t, J=8.3, 7.3 Hz), 2.58 (2H, t, J=7.8 Hz), 2.94 (2H, t, J=7.8 Hz), 3.40 (2H, t, J=8.3 Hz), 3.41 (3H, s), 3.45 (3H, s), 3.47 (3H, s), 3.15 (2H, s), 5.28 (2H, s), 5.32 (2H, s), 6.48 (1H, s), 6.94 (2H, d, J=8.3 Hz), 7.19 (2H, d, J=8.3 Hz), 13.88 (1H, s, eliminated by addition of D$_2$O).

Mass spectrum: M/Z (%) 448 (M$^+$, 26), 340 (20), 239 (100), 224 (59), 193 (23), 179 (53), 151 (41), 121 (37).

Then, 20.9 g of 1-[2-hydroxy-4,6-bis(methoxymethoxy)-3-n-propylphenyl]-3-(4-methoxymethoxyphenyl)-1-propanone was dissolved in 40 ml of methanol, and 20 ml of a 5-15% hydrochloric acid/methanol reagent was added to the solution and the mixture was heated and refluxed for 2 hours. The temperature was lowered to room temperature, 200 ml of a saturated aqueous solution of sodium bicarbonate, and the mixture was extracted with ethyl acetate. The solvent was removed from the ethyl acetate layer by distillation and the obtained residue was subjected to the polyamide column chromatography (diluting solvent=methanol) and recrystallized from benzene to obtain 10.2 g (yield = 69.1%) of 3-(4-hydroxyphenyl)-1-(2,4,6-trihydroxy-3-n-propylphenyl)-1-propanone in the form of a yellow prism.

Melting point: 216° to 218° C.

Infrared absorption spectrum $\nu_{max}^{KBr}$ cm$^{-1}$: 3472, 3328, 2960, 1614, 1566, 1512, 1462, 1432, 1316, 1240, 1226, 1160, 1142, 1114, 1074.

Protron nuclear magnetic resonance spectrum ( $\delta$ ppm in acetone-d$_6$): 0.91 (3H, t, J=7.3 Hz), 1.52 (2H, m), 2.54 (2H, t, J=8.3 Hz), 2.88 (2H, t, J=7.3 Hz), 3.34 (2H, t, J=8.3 Hz), 6.06 (1H, s), 6.74 (2H, d, J=8.3 Hz), 7.09 (2H, d, J=8.3 Hz), 8.00 (1H, br, s, disappeared by addition of D$_2$O) 9.00 (1H, br, s, disappeared by addition of D$_2$O) 13.87 (1H, s, eliminated by addition of D$_2$O).

Mass spectrum: M/Z (%) 316 (M$^+$, 52), 287 (21), 195 (97), 181 (70), 168 (52), 139 (41), 120 (37), 107 (100).

The reaction of Specific Example 10 is illustrated below.

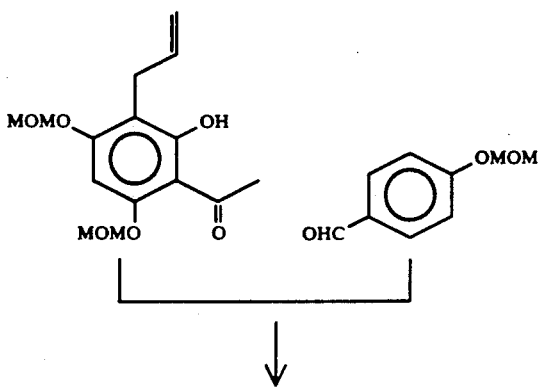

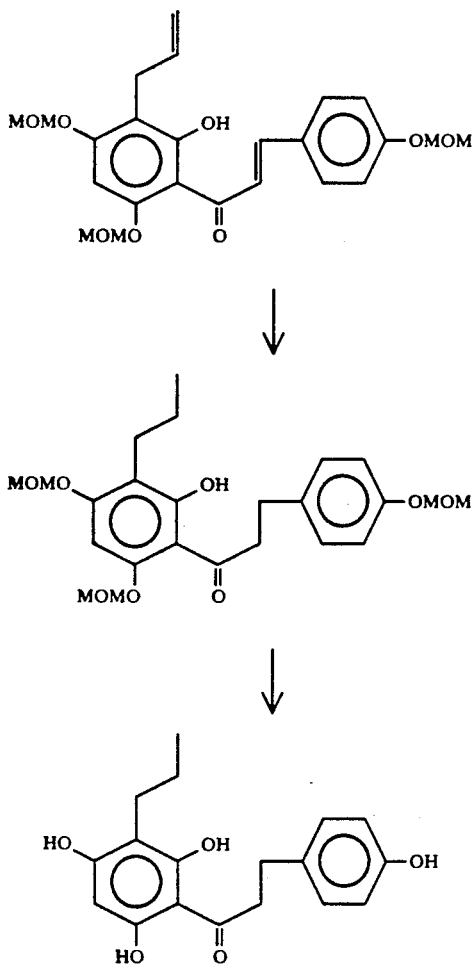

Specific Example 11

To a mixture of 34.7 g of the 2'-hydroxy-4',6'-dimethoxyacetophenone obtained in Production Example 7, 25.3 g of p-anisaldehyde, 150 ml of ethanol and 150 ml of dimethylsulfoxide was added 150 ml of a saturated solution of potassium hydroxide in ethanol at 0° C., and the mixture was stirred at room temperature for 4 hours to effect reaction. After the reaction, the reaction mixture was made acidic by dilute hydrochloric acid to obtain a precipitate. The precipitate was washed with water and recrystallized from a mixed solvent of methanol and ethyl acetate to obtain 43.4 g (yield=78.4%) of 2'-hydroxy-4,4',6'-trimethoxychalcone in the form of a yellow needle.

Infrared absorption spectrum $\nu_{max}^{KBr}$ cm$^{-1}$: 1622, 1602, 1582, 1556, 1512, 1440, 1346, 1290, 1256, 1114, 1032, 1024, 972, 824.

Protron nuclear magnetic resonance spectrum ( δ ppm in CDCl$_3$): 3.83 (3H, s), 3.85 (3H, s), 3.91 (3H, s), . 5.96 (1H, d, J=2.4 Hz), 6.10 (1H, d, J=2.4 Hz), 6.92 (2H, d, J=8.8 Hz), 7.56 (2H, d, J=8.8 Hz), 7.79 (2H, s), 14.43 (1H, s, eliminated by addition of D$_2$O).

Mass spectrum: M/Z (%) 314 (M+, 100), 313 (72), 207 (39), 181 (26), 180 (40), 143 (27), 134 (52), 121 (71).

Then, 100 ml of an ethyl acetate solution of 10.0 g of 2'-hydroxy-4,4',6'-trimethoxychalcone was added to a suspension of 2.0 g of 5% palladium/carbon in 50 ml of ethyl acetate, in which a hydrogen gas had been sufficiently absorbed in advance, and the mixture was stirred at room temperature for 1 hour in a hydrogen gas atmosphere. After the reaction, the reaction mixture was filtered and the solvent was removed from the filtrate by distillation, and the obtained residue was recrystallized from a mixed solvent of methanol and ethyl acetate to obtain 9.3 g (yield=93.0%) of 1-(2-hydroxy-4,6-dimethoxyphenyl)-3-(4-methoxyphenyl)-1propanone in the form of a colorless needle.

Melting point: 110° to 110.5° C.

Infrared absorption spectrum $\nu_{max}^{KBr}$ cm$^{-1}$: 1620, 1584, 1512, 1468, 1442, 1416, 1368, 1292, 1270, 1246, 1218, 1206, 1180, 1156, 1114, 1030, 968, 904, 822.

Protron nuclear magnetic resonance spectrum (δ ppm in CDCl$_3$): 2.93 (2H, t, J=8.3 Hz), 3.28 (2H, t, J=8.3 Hz), 3.79 (3H, s), 3.81 (3H, s), 3.83 (3H, s), 5.92 (1H, d, J=2.4 Hz), 6.07 (1H, d, J=2.4 Hz), 6.84 (2H, t, J=8.8 Hz), 7.16 (2H, d, J=8.8 Hz). 14.04 (1H, s, disappeared by addition of D$_2$O).

Mass spectrum: M/Z (%) 316 (M+, 38), 181 (99), 154 (27), 135 (13), 134 (100), 121 (35).

Then, 30 ml of dimethylformamide was added to 5.0 g of 1-(2-hydroxy-4,6-dimethoxyphenyl)-3-(4-methoxyphenyl)-1-propanone and 420 mg of sodium hydride, and the mixture was stirred at 0° C. for 1 hour. Then, 2.6 g of methyl α-bromoacetate was added to the mixture, and the mixture was stirred at 0° C. for 1 hour and at room temperature for 1 hour to effect a reaction. After the reaction, the reaction mixture was extracted with ethyl acetate and filtered, and the solvent was removed from the filtrate by distillation. The obtained residue was subjected to the silica gel chromatography [230-400 mesh silica gel; eluting solvent=n-hexane/ethyl acetate (2/1)] and recrystallized from a mixed solvent of diethyl ether and n-hexane to obtain 5.3 g (yield=87.1%) of 1-(4,6-dimethoxy-2-methoxycarbonylmethoxyphenyl)-3-(4-methoxyphenyl)-1-propanone in the form of a colorless plate.

Infrared absorption spectrum $\nu_{max}^{KBr}$ cm$^{-1}$: 1764, 1676, 1608, 1588, 1514, 1470, 1452, 1438, 1422, 1412, 1298, 1248, 1220, 1204, 1184, 1154, 1136, 1032, 822, 810.

Protron nuclear magnetic resonance spectrum (δ ppm in CDCl$_3$): 2.95 (2H, m), 3.11 (2H, m), 3.75 (3H, s), 3.76 (3H, s), 3.77 (3H, s), 3.78 (3H, s), 4.57 (2H, s), 5.97 (1H, d, J=2.0 Hz), 6.13 (1H, d, J=2.0 Hz), 6.80 (2H, d, J=8.8 Hz), 7.14 (2H, d, J=8.8 Hz).

Mass spectrum: M/Z (%) 388 (M+, 24), 299 (10), 253 (64), 227 (14), 226 (100), 195 (23), 135 (10), 134 (64), 121 (33), 45 (29).

Then, 6.05 g of 1-(4,6-dimethoxy-2-methoxycarbonylmethoxyphenyl)-3-(4-methoxyphenyl)-1-propanone was dissolved in 50 ml of methanol, and 30 ml of a 5% aqueous solution of potassium hydroxide was added to the solution and the mixture was stirred at room temperature for 30 minutes to effect reaction. After the reaction, the reaction mixture was made acidic by addition of dilute hydrochloric acid, extracted with diethyl ether and filtered, and the solvent was removed from the filtrate by distillation and the obtained residue was recrystallized from a mixed solvent of diethyl ether and n-hexane to obtain 5.0 g (yield=87.4%) of 1-(2-carboxymethoxy-4,6-dimethoxyphenyl)-3-(4-methoxyphenyl)-1-propanone in the form of a colorless prism.

Infrared absorption spectrum $\nu_{max}^{KBr}$ cm$^{-1}$: 1742, 1712, 1686, 1606, 1582, 1514, 1470, 1452, 1438, 1418, 1266, 1234, 1208, 1180, 1160, 1136, 1030, 824.

Protron nuclear magnetic resonance spectrum (δ ppm in acetone-$d_6$): 2.88 (2H, m), 3.07 (2H, m), 3.74 (3H, s), 3.78 (3H, s), 3.82 (3H, s), 4.74 (2H, s), 6.26 (1H, d, J=2.0 Hz), 6.29 (1H, d, J=2.0 Hz), 6.81 (2H, d, J=8.8 Hz), 7.15 (2H, d, J=8.8 Hz).

Mass Spectrum: M/Z (%) 374 (M+, 7), 312 (7), 299 (8), 239 (50), 212 (49), 195 (8), 181 (55), 137 (8), 135 (14), 134 (100), 122 (8), 121 (58), 77 (8).

The reaction of Specific Example 11 is illustrated below.

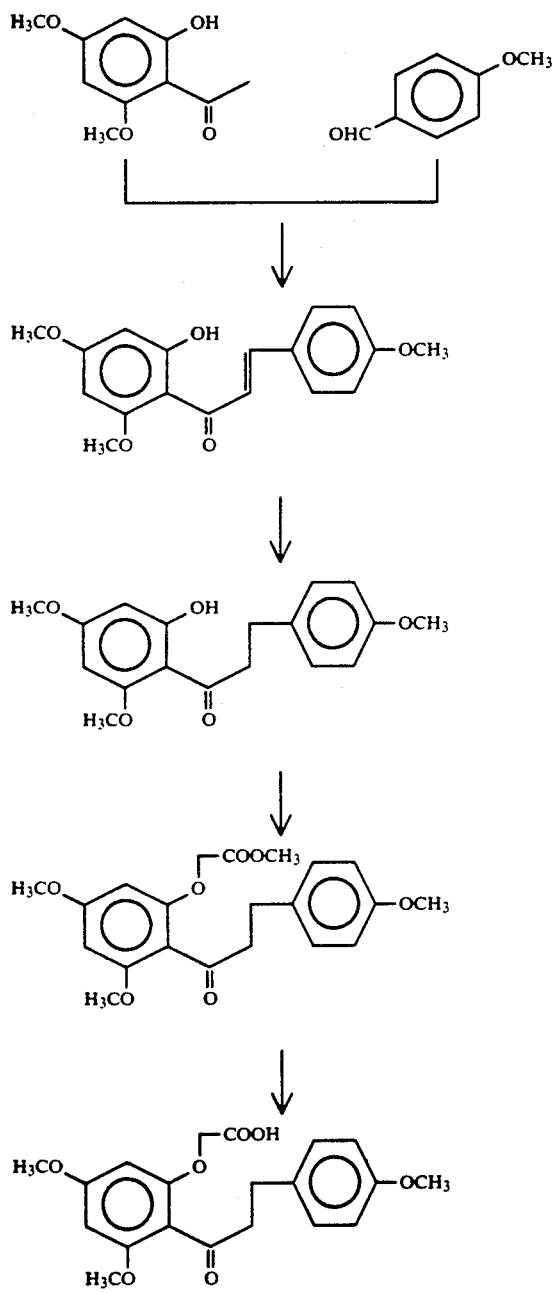

Specific Example 12

To a mixture of 16.4 g of the 2'-hydroxy-4',6'-dimethoxy-3'-(3-methyl-2-butenyl)acetophenone, obtained in Production Example 3, 8.9 g of p-ansialdehyde and 150 ml of ethanol was added 100 ml of a saturated solution of potassium hydroxide in ethanol, and the mixture was stirred at room temperature overnight to effect a reaction. After the reaction, the reaction mixture was made acidic by dilute hydrochloric acid, and the formed precipitate was washed with water, filtered and recrystallized from a mixed solvent of methanol and ethyl acetate to obtain 20.0 g (yield=83.9%) of 2'-hydroxy-4,4',6'-trimethoxy-3'-(3-methyl-2-butenyl)-chalcone in the form of a yellow needle.

Infrared absorption spectrum $\nu_{max}^{KBr}$ cm$^{-1}$: 3124, 2932, 1632, 1608, 1554, 1512, 1470, 1454, 1422, 1376, 1302, 1288, 1226, 1170, 1142, 1114, 1074, 980, 824.

Protron nuclear magnetic resonance spectrum (δ ppm in acetone-$d_6$) 1.63 (3H, d, J=1.5 Hz) 1.75 (3H, d, J=1.5 Hz) 3.26 (2H, d, J=7.3 Hz) 3.85 (3H, s), 3.95 (3H, s), 4.02 (3H, s), 5.19 (1H, t, septet, J=7.3, 1.5 Hz), 6.27 (1H, s) 6.99 (2H, dd, J=6.8, 2.0 Hz), 7.68 (2H, dd, J=6.8, 2.0 Hz), 7.75 (1H, d, J=15.1 Hz), 7.91 (1H, d, J=15.1 Hz), 14.34 (1H, s).

Mass spectrum M/Z (%) 382 (M+, 77), 367 (22), 339 (73), 327 (29), 233 (73), 205 (40), 193 (100), 191 (44), 161 (20), 134 (14), 133 (13), 121 (29), 77 (11), 69 (11), 41 (10).

Then, a liquid mixture of 16.2 g of 2'-hydroxy-4,4',6'-trimethoxy-3'-(3-methyl-2-butenyl)chalcone, 4.0 g of potassium hydroxide and 180 ml of ethanol was added to a suspension of 1.5 g of 5% palladium/carbon in 20 ml of ethyl acetate, in which a hydrogen gas had been sufficiently absorbed in advance, and the mixture was stirred at room temperature in a hydrogen gas atmosphere for 5 hours. After the reaction, the reaction mixture was made acidic by dilute hydrochloric acid, filtered, extracted with ethyl acetate and filtered, and the solvent was removed from the filtrate by distillation. The obtained residue was recrystallized from methanol to obtain 15.4 g (yield=94.6%) of 1-[4,6-dimethoxy-2-hydroxy-3-(3-methyl-2-butenyl)phenyl]-3-(4-methoxyphenyl)-1-propane in the form of a colorless needle.

Infrared absorption spectrum $\nu_{max}^{KBr}$ cm$^{-1}$: 1614, 1582, 1514, 1470, 1454, 1410, 1294, 1276, 1248, 1226, 1212, 1180, 1136, 1112, 1038.

Proton nuclear magnetic resonance spectrum (δ ppm in CDCl$_3$): 1.66 (3H, s), 1.77 (3H, s), 2.92 (2H, m), 3.27 (2H, m), 3.27 (2H, d, J=7.3 Hz), 3.79 (3H, s), 3.87 (3H, s), 3.88 (3H, s), 5.18 (1H, t, J=7.3 Hz), 5.95 (1H, s), 6.84 (2H, d, J=8.8 Hz), 7.16 (2H, d, J=8.8 Hz), 13.93 (1H, s, disappeared by addition of D$_2$O).

Mass spectrum: M/Z (%) 384 (M+, 43), 341 (3), 329 (29), 249 (15), 222 (28), 207 (14), 207 (14), 193 (59), 167 (16), 134 (18), 121 (100).

Then, 30 ml of dimethylformamide was added to 5.2 g of 1-[4,6-dimethoxy-2-hydroxy-3-(3-methyl-2-butenyl)phenyl]-3-(4-methoxyphenyl)-1-propanone and 355 mg of sodium hydride, and the mixture was stirred at 0° C. for 1 hour. Then, 2.2 g of methyl α-bromoacetate was added to the mixture, and the mixture was stirred at 0° C. for 1 hour and at room temperature for 2 hours to effect reaction. After the reaction, the reaction mixture was extracted with ethyl acetate and filtered, and the solvent was removed from the filtrate by distillation. The obtained residue was subjected to the silica gel column chromatography [230-400 mesh silica gel; eluting solvent=n-hexane/ethyl acetate (4/1)] to obtain 5.6 g (yield=91.0%) of 1-[4,6-dimethoxy-2-methoxycarbonylmethoxy-3-(3-methyl-2-butenyl)-phenyl]-3-(4-methoxyphenyl)-1-propanone in the form of a colorless oil.

Infrared absorption spectrum $\nu_{max}^{KBr}$ cm$^{-1}$: 1764, 1698, 1600, 1512, 1464, 1440, 1328, 1246, 1214, 1168, 1116.

Proton nuclear magnetic resonance spectrum (δ ppm in CDCl$_3$): 1.66 (3H, d, J=1.0 Hz), 1.70 (3H, s), 2.92 (2H, m), 3.13 (2H, m), 3.27 (2H, d, J=6.6 Hz), 3.77 (9H, s), 3.84 (3H, s), 4.41 (2H, s), 5.08 (1H, m), 6.27 (1H, m), 6.80 (2H, d, J=8.5 Hz), 7.14 (2H, d, J=8.5 Hz).

Mass spectrum: M/Z (%) 456 (M$^+$, 11), 384 (27), 383 (100) 321 (16), 294 (13), 193 (18), 121 (7).

Then, 1.9 g of 1-[4,6-dimethoxy-2-methoxycarbonyl-methoxy-3-(3-methyl-2-butenyl)phenyl]-3-(4-methoxyphenyl)-1-propanone was dissolved in 20 ml of methanol, and 20 ml of a 5% aqueous solution of potassium hydroxide was added to the solution and the mixture was stirred at room temperature for 30 minutes to effect a reaction. After the reaction, the reaction mixture was made acidic by dilute hydrochloric acid, extracted with diethyl ether and filtered, and the solvent was removed from the filtrate by distillation. The obtained residue was recrystallized from a mixed solvent of ethyl acetate and diethyl ether to obtain 1.7 g (yield=92.4%) of 1-[2-carboxymethoxy-4,6-dimethoxy-3-(3-methyl-2-butenyl)phenyl]-3-(4-methoxyphenyl) -propanone in the form of a colorless prism.

Melting point: 101.5° to 102.0° C.

Infrared absorption spectrum $\nu_{max}^{KBr}$ cm$^{-1}$: 2900, 2852, 1680, 1606, 1514, 1454, 1436, 1406, 1374, 1346, 1244, 1228, 1168, 1128, 1114, Proton nuclear magnetic resonance spectrum (δ ppm in acetone-d$_6$): 1.64 (3H, d, J=1.2 Hz), 1.72 (3H, s), 2.87 (2H, m), 3.05 (2H, m), 3.29 (2H, d, J=6.8 Hz), 3.75 (3H, s), 3.84 (3H, s), 3.90 (3H, s), 4.41 (2H, s), 5.14 (1H, s), 6.57 (1H, s), 6.81 (2H, d, J=8.6 Hz), 7.16 (2H, d, J=8.6 Hz).

Mass spectrum: M/Z (%) 442 (M$^+$, 14), 396 (22), 384 (25), 383 (89), 367 (42), 307 (46), 280 (49), 265 (24), 247 (15), 219 (15), 212 (16), 205 (14), 193 (80), 134 (24), 121 (100).

The reaction of Specific Example 12 is illustrated below.

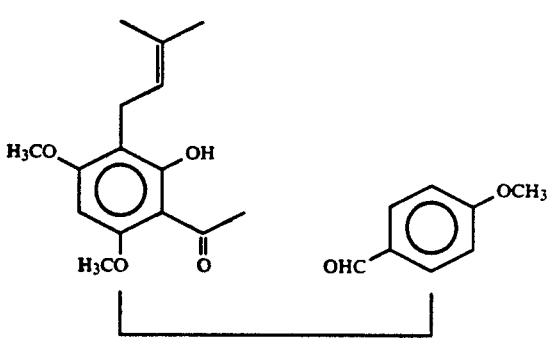

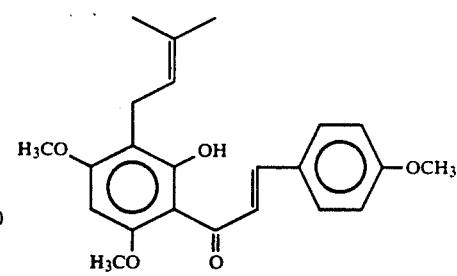

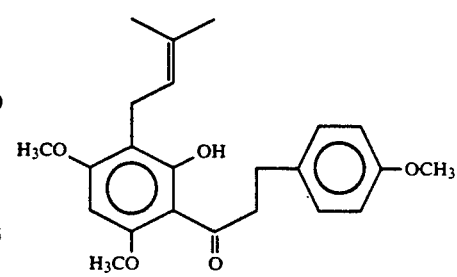

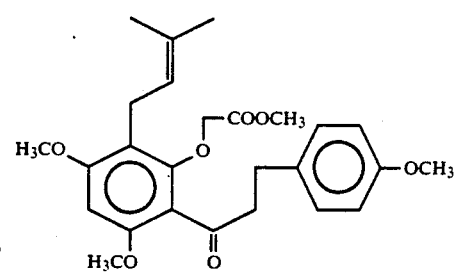

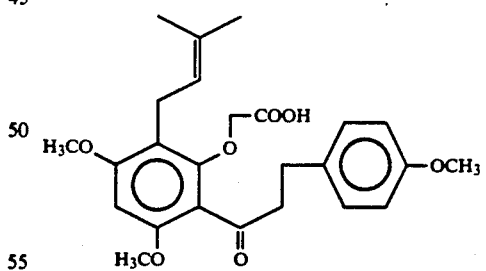

Specific Example 13

To a mixture of 17.0 g of the 2'-hydroxy-4,4',6'-trimethoxychalcone obtained as the intermediate in Specific Example 11, 2.2 g of potassium iodide and 110 ml of dimethylformamide was added 7.3 g of ethyl α-chloroacetate, and the mixture was stirred at room temperature overnight. After the reaction, the reaction mixture was extracted with ethyl acetate and the solvent was removed from the extract by distillation. The obtained residue was recrystallized from a mixed solvent of diethyl ether and ethyl acetate to obtain 19.3 g (yield=89.3%) of 2'-ethoxycarbonylmethoxy-4,4',6'-trimethoxychalcone in the form of a yellow prism.

Infrared absorption spectrum $\nu_{max}^{KBr}$ cm$^{-1}$: 1726, 1638, 1600, 1512, 1468, 1452, 1424, 1298, 1254, 1226, 1196, 1180, 1162, 1130, 1084, 1044, 1024, 990, 836.

Proton nuclear magnetic resonance spectrum ($\delta$ ppm in CDCl$_3$): 1.23 (3H, t, J=7.1 Hz), 3.77 (3H, s), 3.82 (3H, s), 3.83 (3H, s), 4.20 (2H, q, J=7.1 Hz), 4.59 (2H, s), 6.03 (1H, d), 6.20 (1H, d, J=2.2 Hz), 6.88 (2H, d, J=8.8 Hz), 6.91 (1H, d, J=15.9 Hz), 7.42 (1H, d, J=15.9 Hz), 7.50 (2H, d, J=8.8 Hz).

Mass spectrum: M/Z (%) 400 (M+, 36), 382 (60), 373 (34), 372 (100), 327 (33), 309 (52), 308 (40), 181 (36), 161 (32), 133 (34), 121 (85).

Then, 15.1 g of 2'-ethoxycarbonylmethoxy-4,4',6'-trimethoxychalcone was dissolved in 80 ml of dioxane, and 80 ml of a 5% aqueous solution of potassium hydroxide was added to the solution and the mixture was stirred at room temperature for 1 hour to effect a reaction. After the reaction, the reaction mixture was made acidic by hydrochloric acid, extracted with ethyl acetate and filtered, and the solvent was removed from the filtrate by distillation. The residue was recrystallized from a mixed solvent of diethyl ether and ethyl acetate to obtain 11.4 g (yield=81.0%) of 2'-carboxymethoxy-4,4',6'-trimethoxychalcone in the form of a yellow prism.

Melting point: 145° to 146° C.

Infrared absorption spectrum $\nu_{max}^{KBr}$ cm$^{-1}$: 2984, 1762, 1648, 1602, 1586, 1574, 1510, 1468, 1454, 1418, 1364, 1350, 1306, 1286, 1256, 1234, 1204, 1174, 1160, 1126, 1026, 978, 830, 814, 554.

Proton nuclear magnetic resonance spectrum ($\delta$ ppm in acetone-d$_6$): 3.79 (3H, s), 3.84 (3H, s), 3.86 (3H, s), 4.76 (2H, s), 6.33 (1H, d, J=2.0 Hz), 6.36 (1H, d, J=2.0 Hz), 6.95 (1H, d, J=16.1 Hz), 6.97 (2H, d, J=8.6 Hz), 7.45 (1H, d, J=16.1 Hz), 7.61 (2H, d, J=8.6 Hz).

Mass spectrum: M/Z (%) 372 (M+, 12), 344 (47), 310 (98), 309 (31), 279 (33), 181 (56), 161 (32), 134 (37), 133 (30), 121 (100), 77 (30, 43 (65).

The reaction of specific Example 13 is illustrated below.

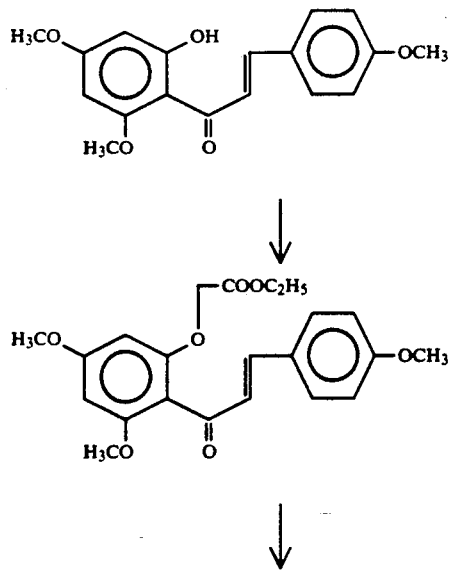

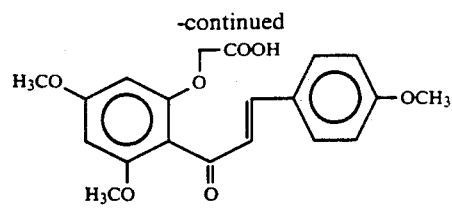

Specific Example 14

To a mixture of 29.0 g of the 2'-hydroxy-4,4',6'-trimethoxy-3'-(3-methyl-2-butenyl)chalcone obtained as the intermediate in Specific Example 12, 21.0 g of anhydrous potassium carbonate, 3.0 g of potassium iodide and 160 ml of dimethylformamide was added 10.2 g of ethyl α-chloroacetate, and the mixture was stirred at room temperature overnight to effect a reaction. After the reaction, the reaction mixture was extracted with ethyl acetate and filtered, and the solvent was removed from the filtrate by distillation. The obtained residue was recrystallized from a mixed solvent of diethyl ether and n-hexane to obtain 33.0 g (yield=92.8%) of 2'-ethoxycarbonylmethoxy-4,4',6'-trimethoxy-3'-(3-methyl-2-butenyl)chalcone in the form of a light-yellow prism.

Melting point: 85° to 86° C.

Infrared absorption spectrum $\nu_{max}^{KBr}$ cm$^{-1}$: 1762, 1632, 1600, 1514, 1462, 1440, 1426, 1272, 1248, 1210, 1180, 1172, 1158, 1116, 1034.

Proton nuclear magnetic resonance spectrum ($\delta$ ppm in CDCl$_3$): 1.24 (3H, t, J=7.1 Hz), 1.67 (3H, d, J=1.2), 1.71 (3H, d, J=1.0 Hz), 3.35 (2H, d, J=6.6 Hz), 3.78 (3H, s), 3.83 (3H, s), 3.88 (3H, s), 4.18 (2H, q, J=7.1 Hz), 5.14 (1H, m), 6.34 (1H, s), 6.88 (2H, d, J=8.6 Hz), 6.88 (1H, d, J=16.1 Hz), 7.33 (1H, d, J=16.1 Hz), 7.47 (2H, d, J=8.6 Hz).

Mass spectrum: M/Z (%) 468 (M+, 5), 450 (15), 382 (13), 381 (37), 248 (12), 247 (100), 193 (11), 161 (15), 121 (11).

Then, 23.7 g of 2'-ethoxycarbonylmethoxy-4,4',6'-trimethoxy-3'-(3-methyl-2-butenyl)chalcone was dissolved in 100 ml of dioxane, and 100 ml of a 5% aqueous solution of potassium hydroxide was added to the solution and the mixture was stirred at room temperature for 30 minutes to effect a reaction. After the reaction, the reaction mixture was made acidic by hydrochloric acid to obtain a yellow precipitate. The precipitate was recovered by filtration, washed with water, dried and recrystallized from ethyl acetate to obtain 18.5 g (yield=83.0%) of 2'-carboxymethoxy-4,4',6'-trimethoxy-3'-(3-methyl-2-butenyl)chalcone in the form of a light-yellow prism.

Melting point: 176° to 177° C.

Infrared absorption spectrum $\nu_{max}^{KBr}$ cm$^{-1}$: 3000, 2968, 2912, 2840, 1704, 1598, 1514, 1464, 1428, 1330, 1308, 1276, 1252, 1222, 1178, 1164, 1116, 1100, 830.

Proton nuclear magnetic resonance spectrum ($\delta$ ppm in acetone-d$_6$): 1.65 (3H, d, J=1.0 Hz), 1.72 (3H, s), 3.34 (2H, d), 3.83 (3H, s), 3.84 (3H, s), 3.94 (3H, s), 4.48 (2H, s), 5.18 (1H, m), 6.63 (1H, s), 6.90 (1H, d, J=16.1 Hz), 6.97 (2H, d, J=9.0 Hz), 7.33 (1H, d, J=16.1 Hz), 7.61 (2H, d, J=9.0 Hz).

Mass spectrum: M/Z (%) 440 (M+, 9), 381 (39), 378 (50), 247 (100), 193 (49), 161 (41), 121 (41), 43 (41).

The reaction of Specific Example 14 is illustrated below.

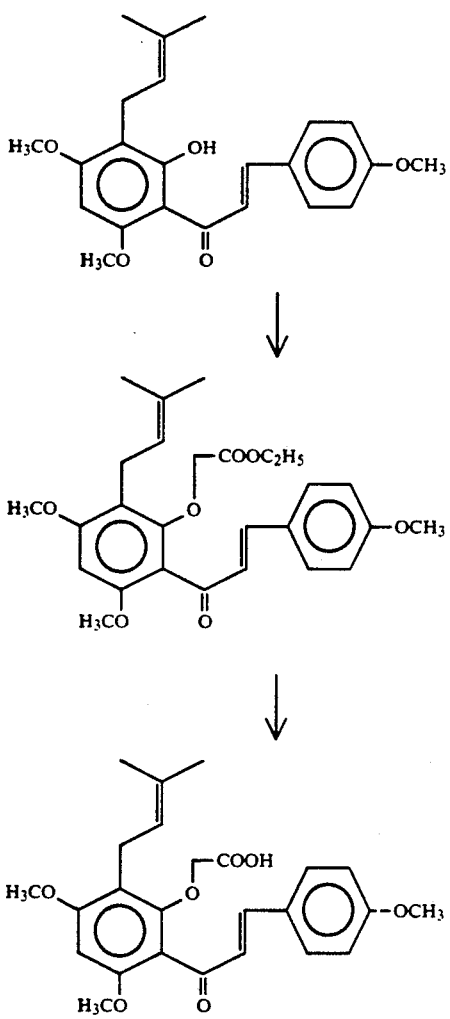

Specific Example 15

To a liquid mixture of 2.08 g of the 2'-hydroxy-4'-methoxymethoxyacetophenone obtained in Production Example 8, 1.94 g of the p-methoxymethoxybenzaldehyde obtained in Production Example 25 and 5 ml of ethanol was added 15 ml of a saturated solution of potassium hydroxide in ethanol under cooling, and the mixture was stirred under ice cooling for 30 minutes and at room temperature overnight to effect a reaction.

After the reaction, the reaction mixture was made acidic by dilute hydrochloric acid to obtain a yellow solid, and the solid was recrystallized from methanol to obtain 2.11 g (yield=57.8%) of 2'-hydroxy-4,4'-bis(methoxymethoxy)chalcone in the form of a yellow prism.

Infrared absorption spectrum $\nu_{max}^{KBr}$ cm$^{-1}$: 1642, 1602, 1568, 1510, 1358, 1278, 1232, 1196, 1172, 1158, 1142, 1076, 1000, 920, 832, 798.

Proton nuclear magnetic resonance spectrum: (δ ppm in CDCl$_3$): 3.49 (6H, s), 5.22 (4H, s), 6.58 (1H, dd, J=8.8, 2.4 Hz), 6.64 (1H, d, J=2.4 Hz), 7.08 (2H, d, J=8.8 Hz), 7.47 (1H, d, J=15.6 Hz), 7.60 (2H, d, J=8.8 Hz), 7.84 (1H, d, J=8.8 Hz), 7.86 (1H, d, J=15.6 Hz), 13.36 (1H, s, eliminated by addition of D$_2$O).

Mass spectrum: M/Z (%) 344 (M+, 100), 343 (28), 299 (15), 167 (15), 166 (16), 164 (19), 151 (78), 147 (55), 134 (18), 46 (30).

Then, 1.0 g of 2'-hydroxy-4,4'-bis(methoxymethoxy)-chalcone was dissolved in 7 ml of tetrahydrofuran, and a 5-15% hydrochloric acid/methanol reagent was added to the solution and the mixture was heated at 50° C. for 30 minutes to effect a reaction. After the reaction, the reaction mixture was neutralized with a saturated aqueous solution of sodium hydrogencarbonate and extracted with 300 ml of ethyl acetate, and the ethyl acetate layer was washed with water (100 ml×3 times), shaken with a saturated aqueous solution of sodium chloride (50 ml×2 times), dried with anhydrous sodium sulfate and filtered. The solvent was removed from the filtrate by distillation, and the obtained residue was subjected to the silica gel column chromatography using a mixed solvent of n-hexane and ethyl acetate to obtain 521 mg (yield=70%) of 2',4,4'-trihydroxychalcone in the form of a yellow grain.

Infrared absorption spectrum $\nu_{max}^{KBr}$ cm$^{-1}$: 3288, 1634, 1590, 1554, 1514, 1370, 1276, 1220, 1198, 1174, 1166, 1126.

Proton nuclear magnetic resonance spectrum (δ ppm in acetone-d$_6$): 6.37 (1H, d, J=2.4 Hz), 6.47 (1H, dd, J=9.0, 2.4 Hz), 6.93 (2H, d, J=8.5 Hz), 7.74 (2H, d, J=8.5 Hz), 7.75 (1H, d, J=15.6 Hz), 7.86 (1H, d, J=15.6 Hz), 8.12 (1H, J=9.0 Hz).

Mass spectrum: M/Z (%) 256 (M+, 98), 255 (61), 163 (41), 150 (30), 137 (100), 120 (49), 107 (28), 91 (20), 45 (86).

The reaction of Specific Example 15 is illustrated below.

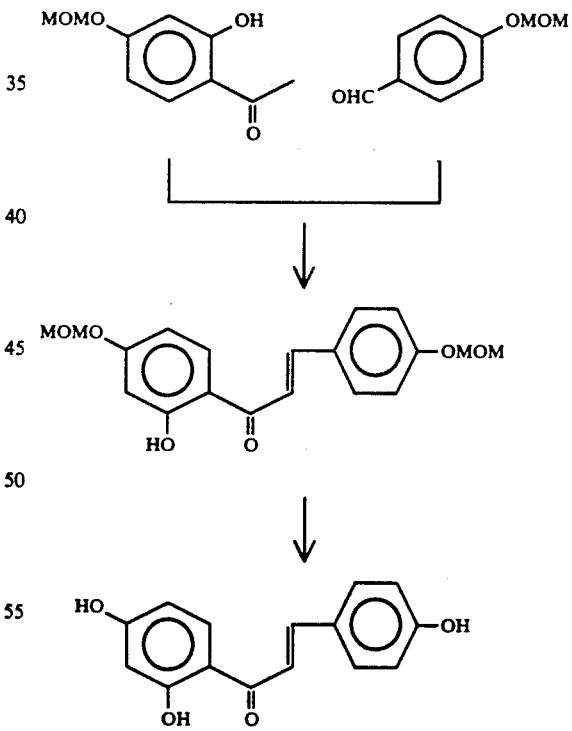

Specific Example 16

In 5 ml of ethanol were dissolved 0.48 g of 2'-hydroxy-4'-methoxy-3'-(3-methyl-2-butenyl)acetophenone obtained in production Example 9 and 0.35 ml of p-anisaldehyde. The solution was cooled to 0° C. and 7.5 ml of a saturated ethanol solution of potassium hydroxide was added to the solution, and the mixture was stirred at 0° C for 30 minutes and at room temperature for 4 days. After the reaction, 3N hydrochloric acid was added to the reaction liquid under cooling to gradually make the liquid acidic, and the formed precipitate was recovered by filtration and recrystallized from methanol to obtain 0.47 g (yield=64.7%) of 2'-hydroxy-4,4'-dimethoxy-3'-(3-methyl-2-butenyl)chalcone in the form of a yellow needle.

Infrared absorption spectrum $\nu_{max}^{KBr}$ cm$^{-1}$: 3440, 3000, 2972, 2916, 2848, 1634, 1606, 1574, 1514, 1494, 1462, 1444, 1416, 1372, 1322, 1310, 1294, 1282, 1262, 1238, 1194, 1174, 1116, 1096, 1070, 1022, 978, 832, 810, 794, 626.

Proton nuclear magnetic resonance spectrum (δ ppm in CDCl$_3$): 1.68 (3H, d, J=1.5 Hz), 1.80 (3H, d, J=1.5 Hz), 3.39 (2H, d, J=6.8 Hz), 3.85 (3H, s), 3.90 (3H, s), 5.23 (1H, t, septet, J=6.8 Hz, J=1.5 Hz), 6.49 (1H, d, J=8.8 Hz), 6.93 (2H, d, J=8.8 Hz), 7.47 (1H, d, J=15.6 Hz), 7.60 (2H, d, J=8.8 Hz), 7.79 (1H, d, J=8.8 Hz), 7.85 (1H, d, J=15.6 Hz), 13.47 (1H, s, eliminated by addition of D$_2$O).

Mass spectrum: M/Z (%) 352 (M$^+$, 76), 310 (21), 309 (100), 297 (35), 203 (25), 190 (21), 175 (32), 163 (92), 161 (43), 133 (20), The reaction of Specific Example 16 is illustrated below.

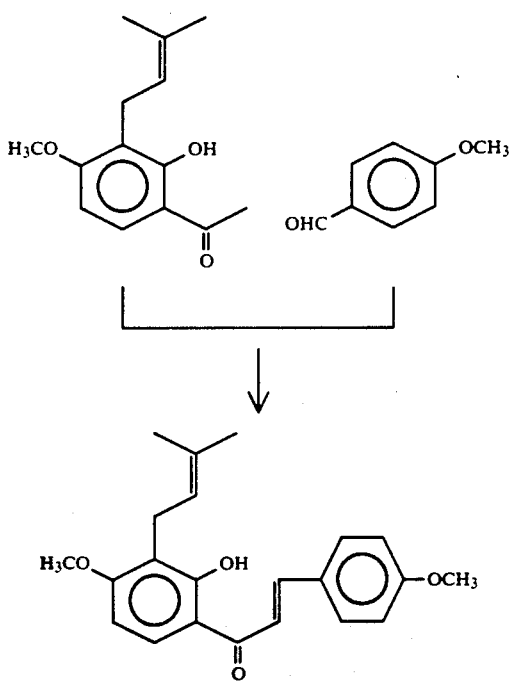

Specific Example 17

In 30 ml of methanol were dissolved 14.73 g of the 2'-hydroxy-4',6'-bis(methoxymethoxy)-3'-(3-methyl-2-butenyl)acetophenone obtained in Production Example 13 and 7.55 g of the p-methoxymethoxybenzaldehyde obtained in Production Example 25, and a saturated solution of sodium hydroxide in methanol was added to the solution and the mixture was stirred at room temperature for 1 day to effect a reaction. After the reaction, the reaction mixture was carefully neutralized with dilute hydrochloric acid and extracted with 1.5 l of ethyl acetate, and the ethyl acetate layer was washed with water (500 ml×4 times), shaken with a saturated aqueous solution of sodium chloride (300 ml×2 times), dried with anhydrous sodium sulfate and filtered. The solvent was removed from the filtrate by distillation to obtain 18.94 g (yield=88.2%) of 2'-hydroxy-4,4',6'-tris(methoxymethoxy)-3'-(3-methyl-2-butenyl)chalcone in the form of a yellow oil.

Infrared absorption spectrum $\nu_{max}^{KBr}$ cm$^{-1}$: 2956, 2920, 1626, 1614, 1584, 1564, 1510, 1424, 1410, 1332, 1316, 1284, 1232, 1206, 1172, 1154, 1132, 1106, 1080, 1068, 986, 960, 922, 832.

Proton nuclear magnetic resonance spectrum (δ ppm in CDCl$_3$): 1.69 (3H, s), 1.79 (3H, s), 3.33 (2H, d, J=7.3 Hz), 3.48 (6H, s), 3.51 (3H, s), 5.20 (2H, s), 5.24 (2H, s), 5.26 (2H, s), 6.39 (1H, s), 7.05 (2H, d, J=8.8 Hz), 7.54 (2H, d, J=8.8 Hz), 7.74 (1H, d, J=13.0 Hz), 7.83 (1H, d, J=13.0 Hz), 13.84 (1H, s, eliminated by addition of D$_2$O).

Mass spectrum: M/Z (%) 472 (M$^+$, 6), 427 (19), 395 (6), 263 (14), 231 (7), 219 (8), 205 (7), 191 (19), 58 (7), 46 (100).

Then, 121 mg of the so-obtained 2'-hydroxy-4,4',6'-tris(methoxymethoxy)-3'-(3-methyl-2-butenyl)chalcone was heated and refluxed for 10 minutes in 2 ml of a hydrochloric acid/methanol reagent, and the reaction mixture was cooled to 0° C. and neutralized with potassium hydrogencarbonate. Then, the mixture was filtered, and the filtrate was distilled under reduced pressure to obtain a dark red residue. The residue was subjected to the silica gel column chromatography (diameter=2.0 cm, length=15 cm, 0.3 kg/cm$^2$, solvent =ethyl acetate), and the yellow band was collected and the solvent was removed by distillation to obtain 83.5 mg of a residue. The residue was purified by the thin layer chromatography (developing solvent: ethyl acetate/n-hexane=1/1) to obtain 23.0 mg (yield=27%) of 2',4,4',6'-tetrahydroxy-3'-(3-methyl-2-butenyl)chalcone.

Infrared absorption spectrum $\nu_{max}^{KBr}$ cm$^{-1}$: 3404, 1626, 1606, 1552, 1512, 1438, 1346, 1232.

Proton nuclear magnetic resonance spectrum (δ ppm in acetone-d$_6$): 1.63 (3H, s), 1.74 (3H, s), 3.27 (2H, d, J=6.9 Hz), 5.25 (1H, bt, J=6.9 Hz), 6.10 (1H, s), 6.89 (2H, d, J=8.7 Hz), 7.56 (2H, d, J=8.7 Hz), 7.73 (1H, d, J=15.4 Hz), 8.14 (1H, d, J=15.4 Hz), 9.00 (2H, bs), 14.39 (1H, s, eliminated by addition of D$_2$O).

Mass spectrum: M/Z (%) 340 (M$^+$, 100), 285 (40), 220 (26), 205 (50), 192 (33), 177 (24), 165 (90), 120 (25).

The reaction of Specific Example 17 is illustrated below.

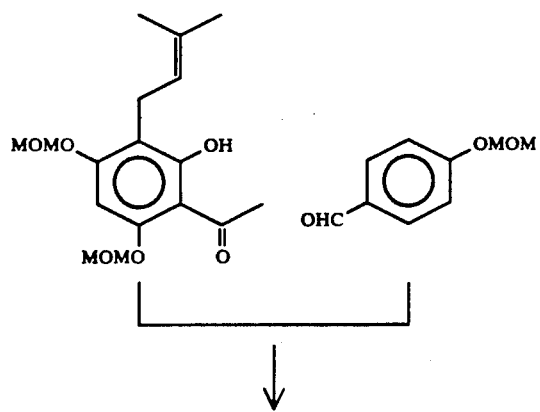

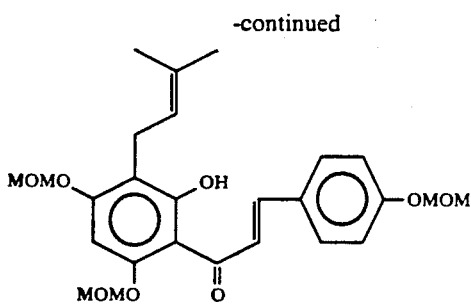

↓

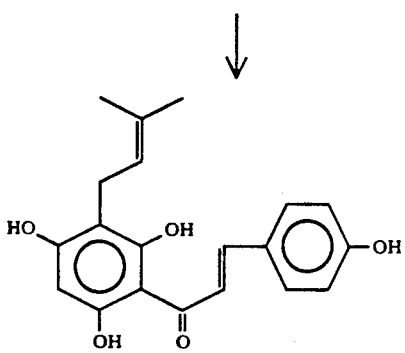

Specific Example 18

A liquid mixture of 13.75 g of the 2'-hydroxy-4,4',6'-tris(methoxymethoxy)-3'-(3-methyl-2-butenyl)chalcone, 40 ml of acetic anhydride and 40 ml of anhydrous pyridine was stirred at room temperature to effect a reaction. Then, the reaction mixture was added into 200 ml of a cooled saturated solution of sodium hydrogen-carbonate and the mixture was stirred at 0° C. for 30 minutes. The mixture was extracted with 1500 ml of ether, and the ether layer was washed with water, shaken with a saturated aqueous solution of copper sulfate, washed with water, shaken with a saturated aqueous solution of sodium chloride, dried with anhydrous sodium sulfate and filtered. The solvent was removed from the filtrate by distillation, and the residue was subjected to the silica gel column chromatography (300 g of 230–400 mesh silica gel, n-hexane/ethyl acetate=4/1, 0.3 kg/cm$^2$). Fractions of 100 ml were collected and the 35th to 37th fractions were combined to obtain 12.58 g (yield=84.0%) of 2'-acetoxy-4,4',6'-tris(methoxymethoxy)-3'-(3-methyl-2-butenyl)chalcone in the form of a yellow oil.

Infrared absorption spectrum $\nu_{max}^{KBr}$ cm$^{-1}$: 2956, 2912, 1770, 1644, 1602, 1574, 15110, 1480, 1446, 1428, 1368, 1318, 1292, 1238, 1206, 1152, 1126, 1080, 1050, 994, 962, 922, 832.

Proton nuclear magnetic resonance spectrum (δ ppm in CDCl$_3$): 1.66 (3H, d, J=1.0 Hz), 1.72 (3H, s), 2.17 (3H, s), 3.20 (2H, d, J=7.3 Hz), 3.39 (3H, s), 3.47 (3H, s), 3.49 (3H, s), 5.12 (2H, s), 5.19 (2H, s), 5.22 (2H, s), 6.87 (1H, s) 6.89 (1H, d, J=15.5 Hz), 7.02 (2H, d, J=8.8 Hz), 7.42 (1H, d, J=15.5 Hz), 7.48 (2H, d, J=8.8 Hz).

Mass spectrum: M/Z (%) 514 (M+, 1), 427 (6), 395 (5) 231 (7), 195 (15), 194 (7), 191 (15), 46 (100).

Then, a liquid mixture of 4.95 g of 2'-acetoxy4,4',6'-tris(methoxymethoxy)-3'-(3-methyl-2-butenyl)chalcone and 8 ml of a hydrochloric acid/methanol reagent was heated and refluxed for 10 minutes, and the temperature of the reaction mixture was lowered to room temperature and the reaction mixture was neutralized with an aqueous solution of sodium hydrogen-carbonate and extracted with 1 l of ethyl acetate. The ethyl layer was washed with water, shaken with a saturated aqueous solution of sodium chloride, dried with anhydrous sodium sulfate and filtered. The solvent was removed from the filtrate by distillation and the obtained residue was subjected to the silica gel column chromatography (130 g of [230–400 mesh silica gel, n-hexane/ethyl acetate=3/1, 0.3 kg/cm$^2$). Fractions of 100 ml were collected and the 13th to 26th fractions were combined to obtain 2.0 g (yield=54.3%) of 2'-acetoxy-4,4',6'-trihydroxy-3'-(3-methyl-butenyl)chalcone in the form of a yellow powder.

Infrared absorption spectrum $\nu_{max}^{KBr}$ cm$^{-1}$: 3380, 2968, 2912, 1776, 1740, 1630, 1606, 1554, 1512, 1440, 1354, 1278, 1212, 1168, 1142, 1102, 1052, 1028, 984, 958, 938.

Proton nuclear magnetic resonance spectrum (δ ppm in CDCl$_3$) 1.72 (3H, s), 1.76 (3H, s), 2.15 (3H, s), 3.18 (2H, d, J=6.3 Hz), 5.13 (1H, t, J=6.3 Hz), 6.32 (1H, s), 6.84 (2H, d, J=8.3 Hz), 7.33 (1H, d, J=15.6 Hz), 7.48 (2H, d, J=8.3 Hz), 7.65 (1H, d, J=15.6 Hz), 12.74 (1H, s, eliminated by addition of D$_2$O).

Mass spectrum: M/Z (%) 382 (M+, 31), 341 (22), 340 (93), 339 (86), 325 (29), 297 (34), 285 (54), 220 (55), 219 (65), 205 (70), 192 (39), 177 (29), 165 (100), 120 (40), 45 (30), 43 (37).

The reaction of Specific Example 18 is illustrated below.

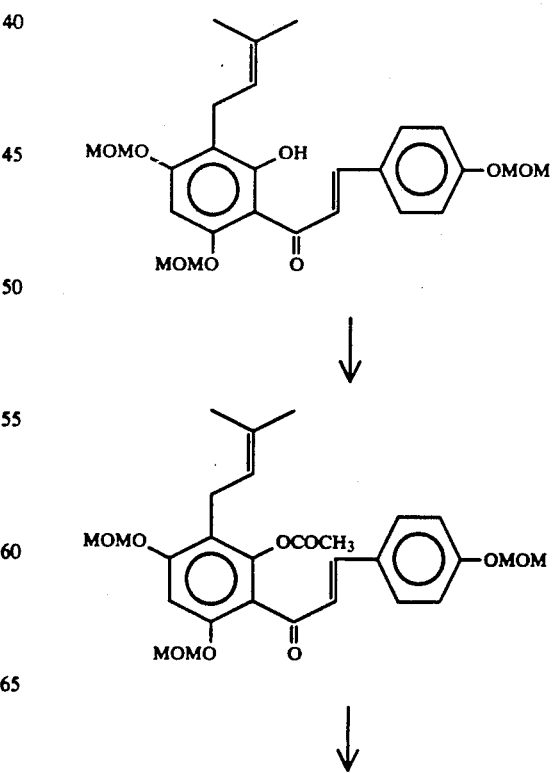

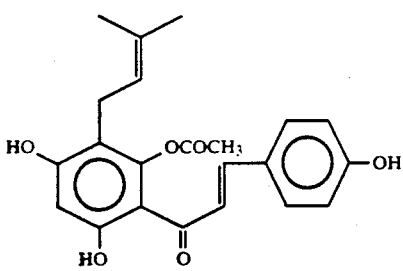

Specific Example 19

In 131 ml of ethanol were dissolved 15.0 g of the 3,4-bis(methoxymethoxy)benzaldehyde obtained in Production Example 24 and 16.0 g of the 2′,4′-bis(methoxymethoxy)acetophenone, and the solution was cooled with ice water and 150 ml of a saturated solution of potassium hydroxide in ethanol was added to the solution. The mixture was stirred at room temperature overnight. After the reaction, the reaction liquid was diluted with water and the pH value was adjusted to about 6 under ice cooling by 6N hydrochloric acid, and the formed precipitate was recovered by filtration, washed with water and dried to obtain 23.39 g (yield - 7.3%) of 2′,3,4,4′-tetrakis(methoxymethoxy)chalcone.

Infrared absorption spectrum $\nu_{max}^{KBr}$ cm$^{-1}$: 2936, 2904, 2824, 1648, 1602, 1590, 1510, 1402, 1316, 1256, 1242, 1194, 1152, 1000, 916.

Proton nuclear magnetic resonance spectrum (δ ppm in CDCl$_3$): 3.49 (3H, s), 3.50 (3H,s), 3.52 (6H, s), 5.21 (2H, s), 5.25 (4H, s), 5.27 (2H, s), 6.77 (1H, dd, J=8.8, 2.2 Hz), 6.86 (1H, d, J=2.2 Hz), 7.20 (1H, dd, J=8.1, 1.2 Hz), 7.21 (1H, d, J=8.1 Hz), 7.36 (1H, d, J=15.9 Hz), 7.45 (1H, d, J=1.2 Hz), 7.59 (1H, d, J=15.9 Hz), 7.67 (1H, d, J=8.8 Hz).

Mass spectrum: M/Z (%) 448 (M+, 2), 327 (2), 299 (3), 211 (1), 181 (2), 179 (2), 135 (1), 46 (2), 45 (100).

Then, 4.0 g of the so-obtained 2′,3,4,4′-tetrakis(methoxymethoxy)chalcone was dissolved in 36 ml of a hydrochloric acid/methanol reagent, and the solution was refluxed for 10 minutes. The reaction liquid was poured into ice water, and the precipitated crystal was recovered by filtration, washed with water, dried and subjected to the column chromatography 280 g of 230–400 mesh Kieselgel, eluting solvent=hexane/ethyl acetate (1/1), 0.4 kg/cm$^2$). Fractions of 50 ml were collected, and the 32th to 70th fractions were combined to obtain 543.2 mg (yield=22.1%) of 2′,3,4,4′-tetrahydroxychalcone.

Infrared absorption spectrum $\nu_{max}^{KBr}$ cm$^{-1}$: 3372, 3248, 1632, 1612, 1594, 1550, 1512, 1370, 1284, 1256, 1220, 1182, 1144, 1112, 1032.

Proton nuclear magnetic resonance spectrum (δ ppm in CDCl$_3$): 6.30 (1H, d, J=2.44 Hz), 6.42 (1H, dd, J=2.44, 8.79 Hz), 6.82 (1H, d, J=8.3 Hz), 7.11 (1H, dd, J=8.3, 1.95 Hz), 7.18 (1H, d, J=1.96 Hz), 7.52 (1H, d, J=15.13 Hz), 7.73 (1H, d, J=15.39 Hz), 7.93 (1H, d, J=9.03 Hz).

Mass spectrum: M/Z (%) 272 (M+, 66), 271 (23), 163 (27), 150 (29), 137 (100), 123 (12), 108 (17), 89 (31), 69 (18), 51 (31), 45 (18).

The reaction of Specific Example 19 is illustrated below.

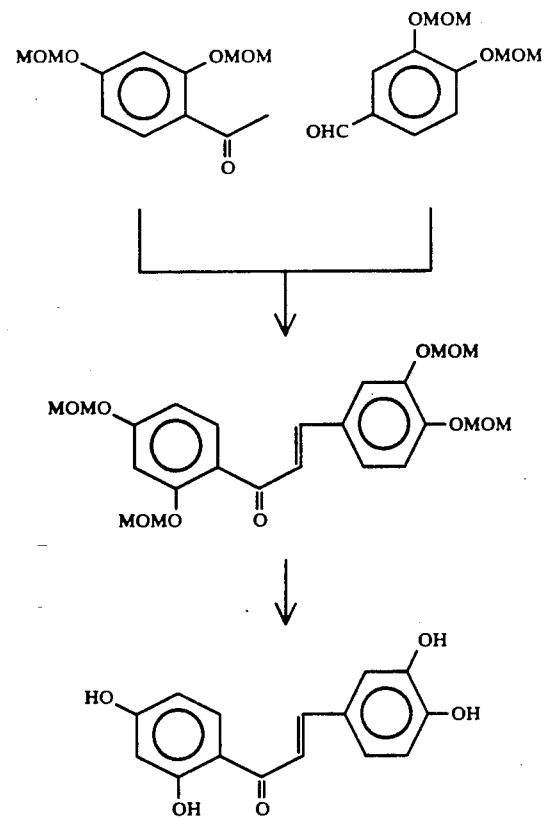

Specific Example 20

In 260 ml of ethanol were dissolved 33.37 g of the 2′-hydroxy-4′,6′-bis(methoxymethoxy)acetophenone obtained in Production Example 11 and 32.20 g of the 3,4-bis(methoxymethoxy)benzaldehyde obtained in Production Example 24, and 300 ml of a saturated solution of potassium hydroxide in ethanol was added to the solution and the mixture was stirred for 24 hours to effect a reaction. After the reaction, the pH value of the reaction liquid was adjusted to about 6 by 6N hydrochloric acid, and the formed precipitate was recovered by filtration, washed with water and dried to obtain 53.17 g (yield=87.9%) of 2′-hydroxy-3,4,4′,6′-tetrakis(methoxymethoxy)chalcone.

Infrared absorption spectrum $\nu_{max}^{KBr}$ cm$^{-1}$: 3464, 2948, 2828, 1626, 1582, 1562, 1510, 1446, 1430, 1418, 1352, 1256, 1226, 1156, 1130, 1082, 1056, 1040, 996, 962, 914.

Proton nuclear magnetic resonance spectrum (δ ppm in CDCl$_3$): 3.48 (3H, s), 3.52 (3H, s), 3.54 (3H, s), 3.55 (3H, s), 5.18 (2H, s), 5.28 (4H, s), 5.30 (2H, s), 6.27 (1H, d, J=2.0 Hz), 6.31 (1H, d, J=2.0 Hz), 7.19 (2H, s), 7.51 (1H, s), 7.73 (1H, d, J=15.6 Hz), 7.87 (1H, d, J=15.6 Hz), 13.23 (1H, s).

Mass spectrum: M/Z (%) 464 (M+, 5), 343 (4), 315 (5), 179 (7), 175 (5), 58 (5), 45 (100), Then, 20 ml of methanol was added to 5.19 g of the so-obtained 2′-hydroxy-3,4,4′,6′-tetrakis(methoxymethoxy)chalcone, and 40 ml of a hydrochloric acid/methanol reagent was added to the formed suspension and the mixture was stirred at 60° C. for 15 minutes. After the reaction, the reaction liquid was poured into water, and the precipitated crystal was recovered by filtration, washed with water and dried to obtain 2.81 g (yield=87.2%) of a crude crystal. The crude crystal was subjected to the column chromatography (200 g of 240-400 mesh Kieselgel 60; 0.3 kg/cm²; eluting solvent hexane/ethyl acetate=2/1, 2700 ml, hexane/ethyl acetate=1/1). Fractions of 50 ml were collected and the 92nd to 149th fractions were combined and concentrated to dryness to obtain 1.06 g (yield=32.9%) of 2′,3,4,4′,6′-pentahydroxychalcone.

Infrared absorption spectrum $\nu_{max}^{KBr}$ cm$^{-1}$: 3304, 1632, 1602, 1546, 1502, 1448, 1220, 1192, 1170, 1082, 1028, 972, 822.

Proton nuclear magnetic resonance spectrum (δ ppm in CD₃OD): 5.87 (2H, s), 6.81 (1H, d, J=8.3 Hz), 7.00 (1H, dd, J=8.3, 1.95 Hz), 7.13 (1H, d, J=1.96 Hz), 7.65 (1H, d, J=15.6 Hz), 8.05 (1H, d, J=15.6 Hz).

Mass spectrum: M/Z (%) 288 (M⁺, 59), 287 (27), 179 (42), 166 (67), 153 (100), 136 (45), 123 (26), 69 (10), 58 (22), 43 (50).

The reaction of Specific Example 20 is illustrated below.

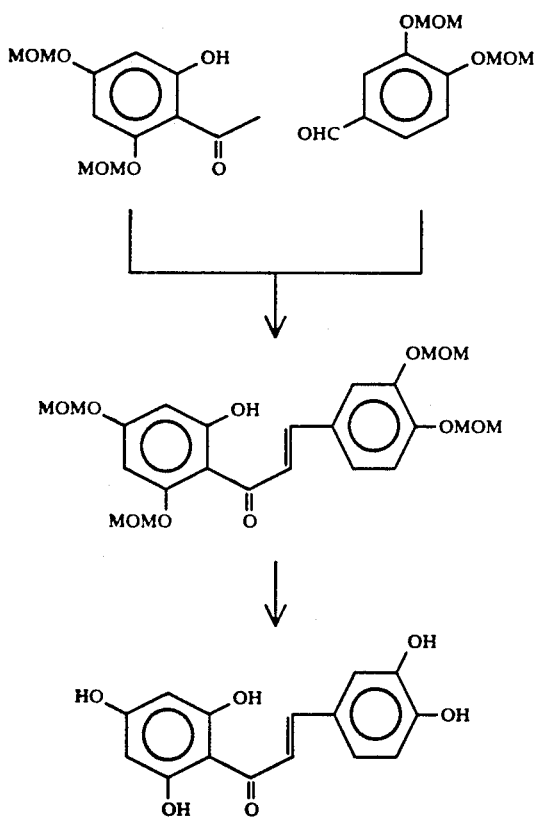

Specific Example 21

In 3 ml of methanol were dissolved 1.40 g of the 2′-hydroxy-4′,6′-bis(methoxymethoxy)-3′-isopentylacetophenone obtained in Production Example 16 and 715 mg of the p-methoxymethoxybenzaldehyde obtained in Production Example 25, and a 50% ethanol solution of sodium hydroxide (4.0 g/8 ml) was added to the solution and the mixture was stirred at room temperature for 1 day to effect a reaction.

After the reaction, the reaction mixture was carefully neutralized with dilute hydrochloric acid and extracted with 300 ml of ether, and the ether layer was washed with water (100 ml×3 times), shaken with a saturated aqueous solution of sodium chloride (100 ml×2 times), dried with anhydrous sodium sulfate and filtered. The solvent was removed from the filtrate by distillation, and the obtained residue was subjected to the silica gel column chromatography (diameter=3.0 cm, 55 g of silica gel, 0.3 kg/cm²) using a mixed solvent of n-hexane and ethyl acetate (n-hexane/ethyl acetate=5/1). Fractions of 100 ml were collected and the 3rd to 10th fractions were combined to obtain 1.75 g (yield=86.0%) of 2′-hydroxy-4,4′,6′-tris(methoxymethoxy)-3′-isopentylchalcone in the form of a yellow oil.

Infrared absorption spectrum $\nu_{max}^{KBr}$ cm$^{-1}$: 2952, 1626, 1610, 1584, 1562, 1510, 1468, 1452, 1424, 1408, 1316, 1284, 1232, 1204, 1172, 1154, 1134, 1080, 1062, 976, 956, 946, 924, 832.

Proton nuclear magnetic resonance spectrum (δ ppm in CDCl₃): 0.95 (6H, d, J=6.4 Hz), 1.37 (2H, m), 1.61 (1H, m), 2.63 (2H, t, J=7.8 Hz), 3.48 (3H, s), 3.49 (3H, s), 3.52 (3H, s), 5.20 (2H, s), 5.23 (2H, s), 5.26 (2H, s), 6.38 (1H, s), 7.05 (2H, d, J=8.8 Hz), 7.54 (2H, d, J=8.8 Hz), 7.74 (1H, d, J=15.6 Hz), 7.84 (1H, d, J=15.6 Hz), 13.81 (1H, s).

Mass spectrum: M/Z (%) 474 (M⁺, 8), 385 (13), 195 (7), 191 (15), 45 (100).

Then, a liquid mixture of 1.45 g of 2′-hydroxy-4,4′,6′-tris(methoxymethoxy)-3′-isopentylchalcone and 4 ml of a hydrochloric acid/methanol reagent was heated and refluxed for 10 minutes. The temperature of the reaction mixture was lowered to room temperature, and the reaction mixture was neutralized with a saturated aqueous solution of sodium bicarbonate, extracted with 500 ml of ethyl acetate, washed with water, shaken with a saturated aqueous solution of sodium chloride, dried with anhydrous sodium sulfate and filtered. The solvent was removed from the filtrate by distillation and the obtained residue was subjected to the silica gel column chromatography (diameter=4.5 cm, 130 g of silica gel, 9.3 kg/cm²) using a mixed solvent of n-hexane and ethyl acetate (n-hexane/ethyl acetate=3/1). Fractions of 100 ml were collected, and the 42nd to 56th fractions were combined, and the solvent was removed by distillation and the residue was recrystallized from a mixed solvent of chloroform and methanol to obtain 620 mg (yield=59.3%) of 2′,4,4′,6′-tetrahydroxy-3′-isopentylchalcone in the form of a yellow prism.

Infrared absorption spectrum $\nu_{max}^{KBr}$ cm$^{-1}$: 3340, 2952, 2864, 1626, 1604, 1550, 1512, 1442, 1346, 1292, 1232, 1168, 1144, 1118, 1074, 1040, 978, 826.

Proton nuclear magnetic resonance spectrum (δ ppm in acetone-d₆): 0.94 (6H, d, J=6.4 Hz), 1.35=1.46 (2H, m), 1.59 (1H, m), 2.60 (2H, t, J=7.8 Hz), 6.10 (1H, s), 6.91 (2H, d, J=8.4 Hz), 7.57 (2H, d, J=8.4 Hz), 7.76 (1H, d, J=15.6 Hz), 8.14 (1H, d, J=15.6 Hz).

Mass spectrum: M/Z (%) 342 (M⁺, 43), 286 (21), 285 (64), 223 (14), 179 (12), 166 (38), 165 (100), 138 (12), 123 (16), 120 (17), 55 (12).

The reaction of Specific Example 21 is illustrated below.

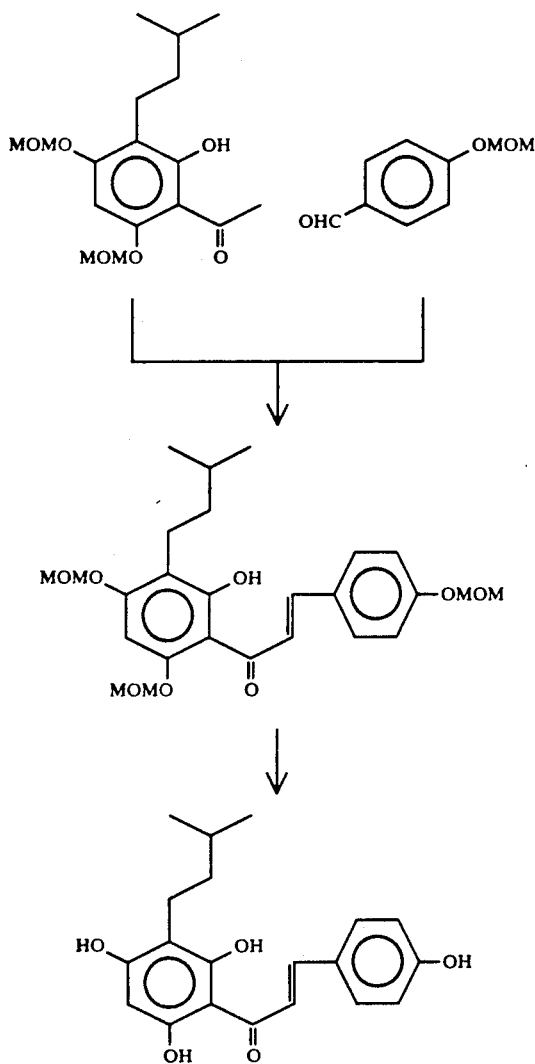

Specific Example 22

In 50 ml of ethanol were dissolved 6.31 g of the 2',4'-bis(methoxymethoxy)acetophenone obtained in Production Example 10 and 4.00 g of the p-methoxymethoxybenzaldehyde obtained in Production Example 25, and the solution was cooled to 0° C. and 30 ml of a saturated solution of potassium hydroxide in ethanol was added to the solution. The temperature of the reaction liquid was elevated to room temperature and the liquid was stirred for 2 days. The reaction liquid was diluted with water, neutralized with 6N hydrochloric acid and extracted with ethyl acetate, and the organic layer was dried with sodium sulfate and concentrated under reduced pressure to obtain a reaction mixture in the form of a syrup. The syrup was subjected to the column chromatography (320 g of 270–400 mesh Kieselgel 60; 0.5 kg/cm²; eluting solvent: hexane/ethyl acetate=1). Fractions of 50 ml were collected and the 66th to 87th fractions were combined to obtain 5.64 g (yield=55.9%) of 2',4,4'-tris(methoxymethoxy)chalcone.

Infrared absorption spectrum $\nu_{max}^{NaCl}$ cm$^{-1}$: 2952, 2904, 1654, 1604, 1574, 1510, 1328, 1314, 1242, 1206, 1154, 1080, 994, 922.

Proton nuclear magnetic resonance spectrum (δ ppm in CDCl₃): 3.47 (3H, s), 3.49 (6H, s), 5.20 (2H, s), 5.20 (2H, s), 5.23 (2H, s), 6.76 (1H, dd, J=8.55, 1.95 Hz), 6.85 (1H, d, J=1.95 Hz), 7.04 (2H, d, J=8.30 Hz), 7.34 (1H, d, J=15.63 Hz), 7.53 (2H, d, J=8.79 Hz), 7.62 (1H, d, J=15.63 Hz), 7.65 (1H, d, J=8.55 Hz).

Mass spectrum: M/Z (%) 389 (1), 388 (M⁺, 4), 195 (13), 194 (14), 45 (100).

Then, a suspension of 2.52 g of 5% palladium/carbon in 50 ml of ethyl acetate was hydrogenated for 2 hours, and a solution of 5.11 g of 2',4,4'-tris(methoxymethoxy)-chalcone in 50 ml of ethyl acetate was added to the suspension and hydrogenation was carried out. After the reaction, the palladium/carbon was removed by filtration and the filtrate was concentrated under a reduced pressure to obtain 1-[2,4-bis(methoxymethoxy)-phenyl]-3-(4-methoxymethoxyphenyl)-1-propanone.

Infrared absorption spectrum $\nu_{max}^{KBr}$ cm$^{-1}$: 2952, 1668, 1602, 1574, 1512, 1444, 1400, 1312, 1246, 1234, 1200, 1154, 1122, 1078, 1008.

Proton nuclear magnetic resonance spectrum (δ ppm in CDCl₃): 3.00 (2H, t, J=7.32 Hz), 3.30 (2H, t, J=7.32 Hz), 3.47 (9H, s), 5.13 (2H, s), 5.18 (2H, s), 5.22 (2H, s), 6.71 (1H, dd, J=8.3, 2.44 Hz), 6.82 (1H, d, J=2.44 Hz), 6.94 (2H, d, J=8.3 Hz), 7.14 (2H, d, J=8.3 Hz), 7.72 (1H, d, J=8.3 Hz).

Mass spectrum: M/Z (%) 390 (M⁺, 2), 330 (11), 181 (68), 151 (16, 45 (100), 43 (17).

Then, 4.44 g of the so-obtained 1-[2,4-bis(methoxymethoxy)phenyl]-3-(4-methoxymethoxyphenyl)-1-propanone was dissolved in methanol, and 38 ml of a hydrochloric acid/methanol reagent was added to the solution and the mixture was stirred at 60° C. for 30 minutes. After the reaction, the reaction liquid was poured into ice water, neutralized with a saturated solution of sodium hydrogencarbonate and extracted with ethyl acetate, and the organic layer was washed with water, dried with sodium sulfate and concentrated under a reduced pressure to obtain a reaction mixture The reaction mixture was subjected to the column chromatography [69 g of 270–400 mesh Kieselgel 60; 0.5 kg/cm²; eluting solvent=hexane/ethyl acetate (1/1)] to obtain 2.55 g (yield=86.7%) of 1-(2,4-dihydroxyphenyl)-3-(4-hydroxyphenyl)-1-propanone.

Infrared absorption spectrum $\nu_{max}^{KBr}$ cm$^{-1}$: 3456, 3272, 1626, 1598, 1514, 1434, 1320, 1294, 1212, 1162, 1134, 986, 778, 746, 620.

Proton nuclear magnetic resonance spectrum (δ ppm in acetone-d₆): 2.92 (2H, t), 3.22 (2H, t), 6.37 (1H, d, J=1.95 Hz), 6.42 (1H, dd, J=8.79, 1.95 Hz), 6.76 (2H, d, J=8.3 Hz), 7.11 (2H, d, J=8.3 Hz), 7.78 (1H, d, J=8,79 Hz), 12.82 (1H, br).

Mass spectrum: M/Z (%) 259 (6), 258 (M⁺, 36), 239 (11), 152 (10), 137 (100), 120 (24), 107 (35), 42 (23), The reaction of Specific Example 22 is illustrated below.

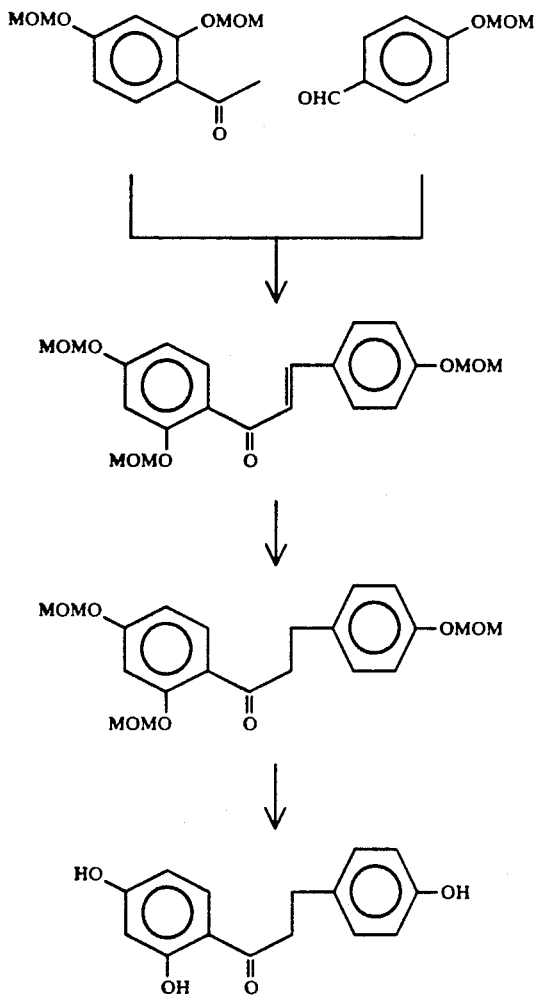

Specific Example 23

In 45 ml of ethanol were dissolved 6.00 g of the 2'-hydroxy-4',6'-bis(methoxymethoxy)acetophenone obtained in Production Example 11 and 3.65 g of the p-methoxybenzaldehyde obtained in Production Example 25, and the solution was cooled to 0° C. and 55 ml of a saturated solution was cooled to 0° C. and 55 ml of a saturated solution of potassium hydroxide in ethanol was added to the solution. The mixture was stirred for 24 hours. After the reaction, the reaction liquid was diluted with water and neutralized with 6N hydrochloric acid, and the formed precipitate was recovered by filtration to obtain 8.17 g (yield=86.3%) of 2'-hydroxy-4,4',6'-tris(methoxymethoxy)chalcone.

Infrared absorption spectrum $v_{max}^{NaCl}$ cm$^{-1}$: 2948, 2824, 1626, 1604, 1574, 1548, 1510, 1486, 1474, 1222, 1202, 1172, 1152, 1056, 1018, 1004, 942, 920.

Proton nuclear magnetic resonance spectrum (6 ppm in CDCl$_3$): 3.48 (3H, s), 3.49 (3H, s), 3.53 (2H, s), 5.18 (2H, s), 5.20 (2H, s), 5.28 (2H, s), 6.24 (1H, d, J=1.96 Hz), 6.31 (1H, d, J=1.96 Hz), 7.08 (2H, d, J=8.79 Hz), 7.55 (2H, d, J=8.79 Hz), 7.75 (1H, d, J=15.6 Hz), 7.85 (1H, d, J=15.6 Hz), 13.85 (1H, s).

Mass spectrum: M/Z (%) 405 (2), 404 (8), 359 (8), 331 (6), 195 (10), 194 (4), 191 (4), 45 (100).

Then, a suspension of 4.10 g of 5% palladium/carbon in 50 ml of ethyl acetate was saturated with hydrogen, and 60 ml of an ethyl acetate solution of 6.61 g of 2'-hydroxy-4,4',6'-tris(methoxymethoxy)chalcone was added to the suspension and hydrogenation was carried out. After the reaction, the reaction liquid was filtered and concentrated under a reduced pressure to obtain 6.10 g (yield=91.8%) of 1-[2-hydroxy-4,6-bis(methoxymethoxy)phenyl]-3-(4-methoxymethoxyphenyl)-1-propanone.

Infrared absorption spectrum $v_{max}^{KBr}$ cm$^{-1}$: 2952, 2828, 2072, 1622, 1512, 1486, 1432, 1416, 1400, 1226, 1198, 1156, 1080, 1022, 924, 830.

Proton nuclear magnetic resonance spectrum (δ ppm in CDCl$_3$): 2.96 (2H, t, J=7.81 Hz), 3.34 (2H, t, J=7.81 Hz), 3.465 (9H, s), 3.472 (9H, s), 5.15 (2H, s), 5.16 (2H, s), 5.22 (2H, s), 6.25 (1H, d, J=2.44 Hz), 6.27 (1H, d, J=2.44 Hz), 6.96 (2H, d), 7.15 (2H, d), 13.67 (1H, s).

Mass spectrum: M/Z (%) 406 (M$^+$, 3), 374 (1), 197 (26), 45 (100), 43 (30) TM

Then, 5.94 g of 1-[2-hydroxy-4,6-bis(methoxymethoxy)phenyl]-3-(4-methoxymethoxyphenyl)-1-propanone was stirred with 87 ml of methanol and 52 ml of a hydrochloric acid/ethanol reagent at 60° C. for 35 minutes. Then, the reaction mixture was poured into ice water and the precipitated crystal was recovered by filtration and dried. The crystal was subjected to the column chromatography [330 g of 270-400 mesh Kieselgel 60; 0.5 kg/cm$^2$; eluting solvent=hexane/ethyl acetate (2/1)]. Fractions of 50 ml were collected and the 11th to 42nd fractions were combined to obtain 2.58 g (yield=64.4%) of 1-(2,4,6-trihydroxyphenyl)-3-(4-hydroxyphenyl)-1-propanone.

Infrared absorption spectrum $v_{max}^{KBr}$ cm$^{-1}$: 3264, 1636, 1606, 1574, 1530, 1512, 1476, 1246, 1210, 1162, 1076, 828, 526.

Proton nuclear magnetic resonance spectrum (δ ppm in acetone-d$_6$): 2.88 (2H, t, J=8.3 Hz), 3.34 (2H, t, J=8.3 Hz), 5.93 (2H, s), 6.74 (2H, d, J=8.3 Hz), 7.09 (2H, d, J=8.3 Hz).

Mass spectrum: M/Z (%) 275 (6), 274 (M$^+$, 35), 255 (11), 153 (100), 120 (67), 107 (59), 59 (12), 42 (21).

The reaction of Specific Example 23 is illustrated below.

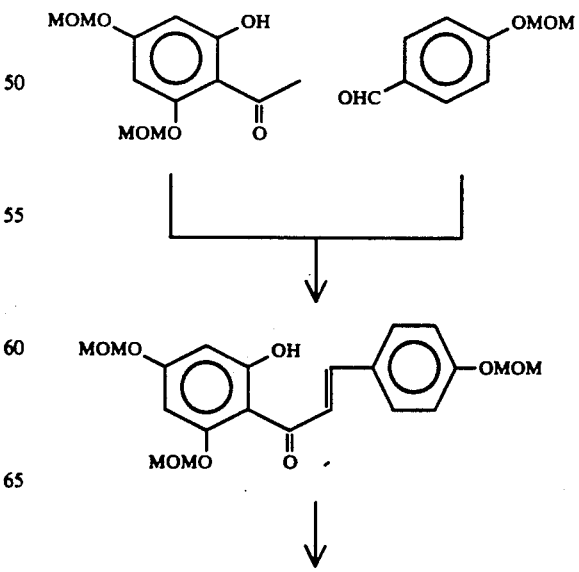

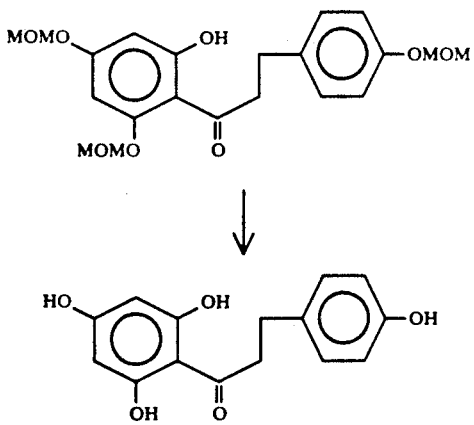

Specific Example 24

An ethanol solution (100 ml) of the 9.89 g of the 2'-acetoxy-4,4',6'-tris(methoxymethoxy)-3'-(3-methyl-2-butenyl)chalcone obtained as the intermediate in Specific Example 18 was added into a suspension of 5.0 g of 5% palladium/carbon in 70 ml of ethanol, in which a hydrogen gas had been sufficiently absorbed in advance, and hydrogen was absorbed by stirring the mixture at 0° C. under atmospheric pressure in a hydrogen gas atmosphere for 1.5 hours with 430.55 ml of a hydrogen gas. After the reaction, the reaction mixture was filtered and the solvent was removed from the filtrate by distillation. The obtained residue was subjected to the silica gel column chromatography [280 g of [230–400 mesh silica gel; n-hexane/ethyl acetate (5/1); 0.3 kg/cm$^2$]. Fractions of 100 ml were collected and the 30th to 52nd fractions to obtain 4.58 g (yield=46.1%) of 1-[2-acetoxy-4,6-bis(methoxymethoxy)-3-(3-methyl-2-butenyl)phenyl]-3-(4-methoxymethoxyphenyl)-1-propanone.

Infrared absorption spectrum $\nu_{max}^{KBr}$ cm$^{-1}$: 3576, 3444, 2928, 1770, 1692, 1610, 1582, 1512, 1480, 1444, 1404, 1368, 1316, 1294, 1232, 1200, 1154, 1124, 1078, 1056, 1006, 962, 922, 876, 828.

Proton nuclear magnetic resonance spectrum (δ ppm in CDCl$_3$): 1.65 (3H, s), 1.72 (3H, s), 2.16 (3H, s), 2.92 (2H, t, J=7.0 Hz), 3.12 (2H, t, J=7.0 Hz), 3.17 (2H, d, J=6.8 Hz), 3.40 (3H, s), 3.45 (6H, s), 5.07 (1H, t, J=6.8 Hz), 5.09 (2H, s), 5.13 (2H, s), 5.19 (2H, s), 6.82 (1H, s), 6.94 (2H, d, J=8.6 Hz), 7.14 (2H, d, J=8.6 Hz).

Mass spectrum M/Z (%) 516 (M+, 1), 471 (5), 429 (4), 397 (4), 307 (6), 265 (7), 249 (7), 247 (12), 219 (5), 217 (4), 209 (4), 205 (19), 165 (4), 151 (9), 121 (6), 45 (100).

Then, a liquid mixture of 1.82 g of the so-obtained 1-[2-acetoxy-4,6-bismethoxymethoxy-3-(3-methyl-2-butenyl)phenyl]-3-(4-methoxymethoxyphenyl)-1-propanone and 5 ml of a hydrochloric acid/methanol reagent was heated and refluxed for 10 minutes. The temperature of the reaction mixture was lowered to room temperature and the reaction mixture was neutralized with a saturated solution of sodium hydrogencarbonate, extracted with 500 ml of ethyl acetate, washed with water (300 ml×3 times), shaken with a saturated aqueous solution of sodium chloride (200 ml×2 times), dried with anhydrous sodium sulfate and filtered. The solvent was removed from the filtrate by distillation, and the residue was recrystallized from chloroform to obtain 710 mg (yield =52.4%) of 1-[2-acetoxy-4,6-hydroxy-3-(3-methyl-2-butenyl)phenyl]-3-(4-hydroxyphenyl)-1-propanone in the form of a colorless prism.

Infrared absorption spectrum $\nu_{max}^{KBr}$ cm$^{-1}$: 3512, 3464, 2968, 2924, 1752, 1722, 1630, 1594, 1514, 1438, 1370, 1282, 1264, 1246, 1224, 1206, 1180, 1140, 1100, 1050, 978, 834.

Proton nuclear magnetic resonance spectrum (δ ppm in acetone-d$_6$): 1.63 (3H, d, J=1.4 Hz), 1.71 (3H, s), 2.26 (3H, s), 2.89 (2H, t, J=7.3 Hz), 3.12 (2H, d, J=5.9 Hz), 3.18 (2H, t, J=7.3 Hz), 5.09 (1H, td, J=5.9, 1.4 Hz), 6.36 (1H, s), 6.76 (2H, d, J=8.3 Hz), 7.10 (2H, d, J=8.3 Hz).

Mass spectrum: M/Z (%) 384 (M+, 14), 341 (32), 221 (30, 194 (32), 165 (77), 107 (100), 55 (33), 43 (85), 41 (46).

The reaction of Specific Example 24 is illustrated below.

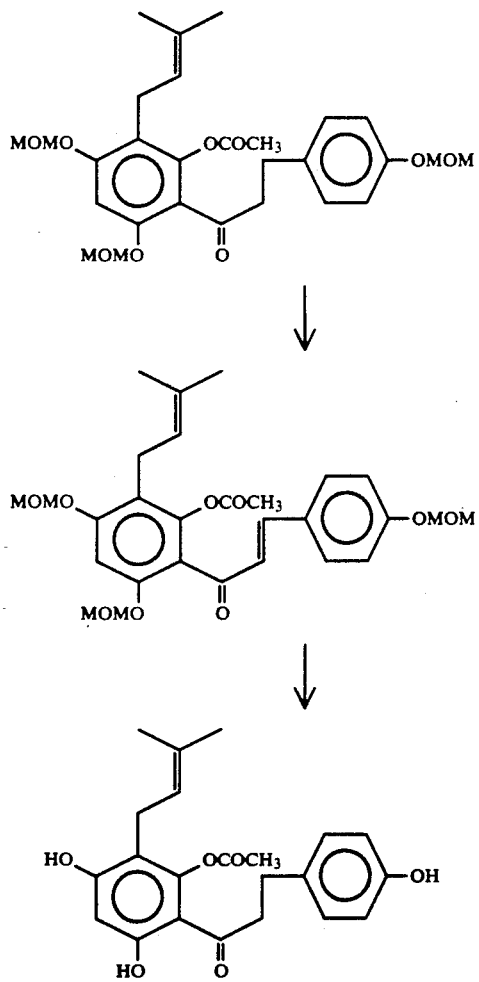

Specific Example 25

To 10 ml of a methanol solution of 500 mg of the 1-[2-acetoxy-4,6-dihydroxy-3-(3-methyl-2-butenyl)phenyl]-3-(4-hydroxyphenyl)-1-propanone obtained in Specific Example 24 was added an aqueous solution of potassium hydroxide (1.5 g/5 ml), and the mixture was stirred at room temperature for 45 minutes. After the reaction, the reaction mixture was carefully neutralized wit dilute hydrochloric acid, extracted with 300 ml of ethyl acetate, washed with water (100 ml×4 times), shaken with a saturated aqueous solution of sodium chloride (100 ml×2 times), dried with anhydrous sodium sulfate and filtered. The solvent was removed from the filtrate by distillation, and the obtained residue was recrystallized from a mixed solvent of chloroform and methanol to obtain 325 mg (yield=73.0%) of 1-[2,4,6-trihydroxy-3-(3-methyl-2-butenyl)phenyl]-3-(4-hydroxyphenyl)-1-propanone in the form of a colorless prism.

Infrared absorption spectrum $\nu_{max}^{KBr}$ cm$^{-1}$: 3340, 2952, 2864, 1626, 1604, 1550, 1512, 1442, 1346, 1292, 1232, 1168, 1144, 1118, 1074, 1040, 978, 826.

Proton nuclear magnetic resonance spectrum ($\delta$ ppm in acetone-d$_6$): 1.63 (3H, s), 1.74 (3H, s), 2.88 (2H, t, J=7.3 Hz), 3.25 (2H, d, J=6.8 Hz), 3.34 (2H, t, J=7.3 Hz), 5.23 (1H, t, J=6.8 Hz), 6.07 (1H, s), 6.75 (2H, d, J=8.3 Hz), 7.09 (2H, d, J=8.3 Hz), 8.07 (1H, brs), 9.08 (1H, brs), 9.52 (1H, brs), 13.99 (1H, s, eliminated by addition of D$_2$O).

Mass spectrum: M/Z (%) 342 (M$^+$, 54), 287 (19), 221 (26), 194 (25), 181 (20), 165 (68), 139 (27), 107 (65), 44 (100).

The reaction of Specific Example 25 is illustrated below.

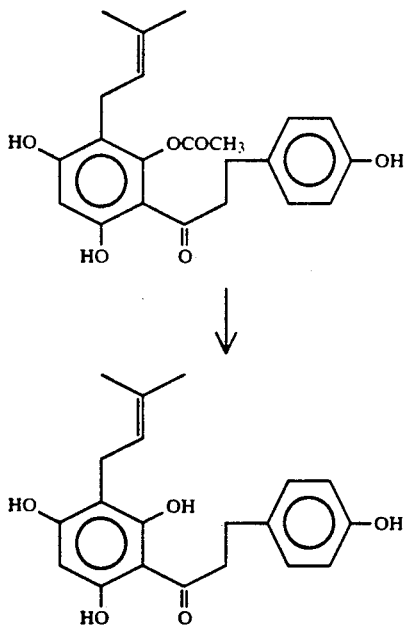

Specific example 26

An ethanol solution (60 ml) of 6.0 g of the 2'-hydroxy-4,4',6'-tris(methoxymethoxy)-3'-(3-methyl-2-butenyl)chalcone obtained as the intermediate in Production Example 17 was added to a suspension of 3.0 g of 5% palladium/carbon in 40 ml of ethanol, in which a hydrogen gas had been sufficiently absorbed in advance, and the mixture was stirred at room temperature under atmospheric pressure in a hydrogen gas atmosphere for 1 hour. After the reaction, the reaction was filtered and the solvent was removed from the filtrate by distillation. The obtained residue was subjected to the silica gel chromatography (116 g of 230–400 mesh silica gel; n-hexane/ethyl acetate=5/1; 0.3 kg/cm$^2$) Fractions of 100 ml were collected, and the 6th to 10th fractions were combined to obtain 5.08 g (yield=84.0%) of 1-[2-hydroxy-4,6-bis(methoxymethoxyphenyl)-3-isopentylphenyl]-3-(4-methoxymethoxyphenyl)-1-propanone in the form of a yellow oil.

Infrared absorption spectrum $\nu_{max}^{KBr}$ cm$^{-1}$: 3576, 3464, 2952, 1616, 1512, 1486, 1468, 1446, 1424, 1402, 1286, 1232, 1202, 1154, 1134, 1080, 1064, 1006, 974, 942, 922, 826.

Proton nuclear magnetic resonance spectrum ($\delta$ ppm in CDCl$_3$): 0.94 (6H, d, J=6.4 Hz), 1.38 (2H, m), 1.59 (1H, m), 2.64 (2H, t, J=7.6 Hz), 2.96 (2H, t, J=8.3 Hz), 3.34 (2H, t, J=8.3 Hz), 3.46 (2H, s), 3.47 (3H, s), 3.48 (3H, s), 5.14 (2H, s), 5.21 (2H, s), 5.22 (2H, s), 6.39 (1H, s), 6.96 (1H, d, J=8.3 Hz), 7.15 (1H, d, J=8.3 Hz), 13.77 (1H, s, eliminated by addition of D$_2$O).

Mass spectrum: M/Z (%) 476 (M$^+$, 7), 399 (4), 368 (4), 284 (4), 267 (17), 252 (6), 207 (12), 196 (6), 165 (5), 164 (6), 151 (9), 121 (8), 45 (100).

Then, 2.55 g of the so-obtained 1-[2-hydroxy-4,6-bis(methoxymethoxy)-3-isopentylphenyl]-3-(4-methoxymethoxyphenyl)-1-propanone was dissolved in 2 ml of methanol, and 4 ml of a hydrochloric acid/methanol reagent was added to the solution and the mixture was heated and refluxed for 20 minutes. The temperature of the reaction mixture was lowered to room temperature, and the reaction mixture was neutralized with a saturated solution of sodium hydrogencarbonate and extracted with 500 ml of ethyl acetate. The ethyl acetate layer was washed with water (200 ml×4 times), shaken with a saturated aqueous solution of sodium chloride (200 ml×2 times), dried with anhydrous sodium sulfate and filtered. The solvent was removed from the filtrate by distillation, and the residue was recrystallized from a mixed solvent of chloroform and methanol to obtain 1.3 g (yield=70.7%) of 1-(2,4,6-trihydroxy-3-isopentylphenyl)-3-(4-hydroxyphenyl)-1-propanone in the form of a yellow prism.

Infrared absorption spectrum $\nu_{max}^{KBr}$ cm$^{-1}$: 3392, 2952, 2900, 2868, 1620, 1608, 1570, 1514, 1440, 1386, 1368, 1324, 1306, 1264, 1216, 1174, 1144, 1126, 1114, 1068, 1046, 822, 638, 622, 598, 572, 516.

Proton nuclear magnetic resonance spectrum ($\delta$ ppm in acetone-d$_6$): 0.93 (6H, d, J=6.3 Hz), 1.40 (2H, m), 1.54 (1H, m), 2.58 (2H, t, J=7.6 Hz), 2.89 (2H, t, J=7.3 Hz), 3.35 (2H, t, J=7.3 Hz), 6.06 (1H, s), 6.75 (2H, d, J=8.6 Hz), 7.09 (2H, d, J=8.6 Hz).

Mass spectrum: M/Z (%) 344 (M$^+$, 61), 287 (37), 269 (11), 224 (12), 223 (89), 196 (64), 182 (18), 181 (85), 165 (18), 163 (18), 140 (14), 139 (53), 120 (46).

The reaction of Specific Example 26 is illustrated below.

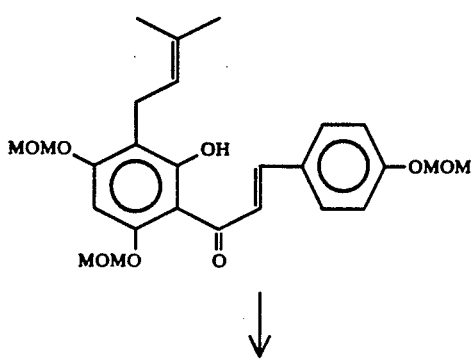

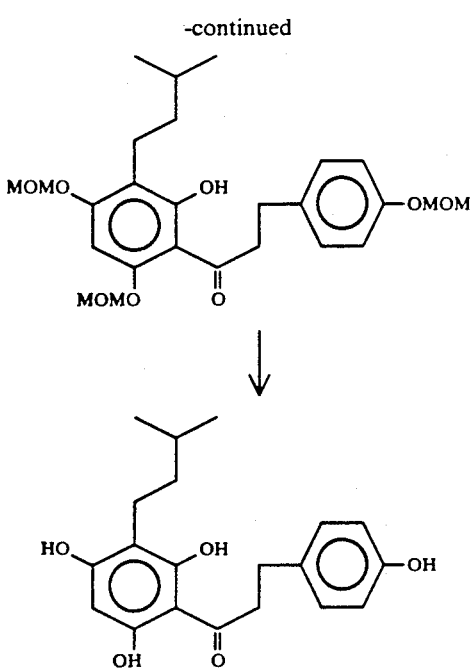

Specific Example 27

Catalytic reduction of 5.05 g of the 2',3,4,4'-tetrakis(methoxymethoxy)chalcone obtained as the intermediate in Specific Example 19 was carried out by using 1.76 g of 5% palladium/carbon according to customary procedures. After the reaction, the reaction liquid was filtered and the solvent was removed from the filtrate by distillation to obtain 4.94 g (yield=97.3%) of 1-[2,4-bis(methoxymethoxy)phenyl]-3-[3,4-bis(methoxymethoxy)phenyl]-1-propanone.

Infrared absorption spectrum $\nu_{max}^{nijol}$ cm$^{-1}$: 2952, 2904, 1666, 1602, 1512, 1402, 1260, 1246, 1190, 1154, 1128, 1110, 1076, 1004, 992, 920.

Proton nuclear magnetic resonance spectrum ($\delta$ ppm in CDCl$_3$): 2.95 (2H, t, J=7.3 Hz), 3.27 (2H, t, J=7.3 Hz), 3.47 (3H, s), 3.48 (3H, s), 3.51 (6H, s), 5.19 (4H, s), 5.21 (2H, s), 5.25 (2H, s), 6.72 (1H, dd, J=8.8, 2.0 Hz), 6.82 (1H, dd, J=8.3, 2.0 Hz), 6.83 (1H, d, J=2.0 Hz), 7.04 (1H, d, J=1.5 Hz), 7.06 (1H, d, J=8.3 Hz), 7.74 (1H, d, J=8.3 Hz).

Mass spectrum: M/Z (%) 450 (M$^+$, 2), 211 (2), 181 (16), 151 (3), 148 (3), 135 (4), 46 (2), 45 (100).

Then, 4.94 g of 1-[2,4-bis(methoxymethoxy)phenyl]-3-[3,4-bis(methoxymethoxy)phenyl]-1-propanone was dissolved in 48 ml of a hydrochloric acid/methanol reagent, and the solution was refluxed for 8 minutes and the reaction liquid was poured into ice water and extracted with ethyl acetate two times. The organic layer was washed with water three times, shaken with a saturated aqueous solution of sodium chloride, dried with anhydrous sodium sulfate and filtered, and the solvent was removed from the filtrate by distillation. The obtained residue was subjected to the column chromatography (400 g of [230–400 mesh silica gel, n-hexane/ethyl acetate=3/2, 0.5 kg/cm$^2$). Fractions of 50 ml were collected, and the 96th to 120th fractions were combined and the solvent was removed by distillation. The residue was recrystallized from n-hexane and chloroform to obtain 453.6 mg (yield=39.0%) of 1-(2,4-dihydroxyphenyl)-3-(3,4-dihydroxyphenyl)-1-propanone.

Infrared absorption spectrum $\nu_{max}^{KBr}$ cm$^{-1}$: 3400, 3312, 1612, 1514, 1440, 1378, 1346, 1310, 1282, 1220, 1190, 1180, 1138, 1108, 968, 848, 792.

Proton nuclear magnetic resonance spectrum ($\delta$ ppm in CD$_3$OD): 2.84 (2H, t, J=6.8 Hz), 3.16 (2H, t, J=6.8 Hz), 6.24 (1H, d, J=2.4 Hz), 6.33 (1H, dd, J=8.8, 2.5 Hz), 6.54 (1H, dd, J=7.8, 2.0 Hz), 6.66 (1H, d, J=7.8 Hz), 6.67 (1H, d, J=2.0 Hz), 7.42 (1H, d, J=8.8 Hz).

Mass spectrum: M/Z (%) 274 (M$^+$, 26), 152 (19), 137 (100), 123 (25), 91 (12), 81 (26), 77 (16), 53 (19), 51 (17).

The reaction of Specific Example 27 is illustrated below.

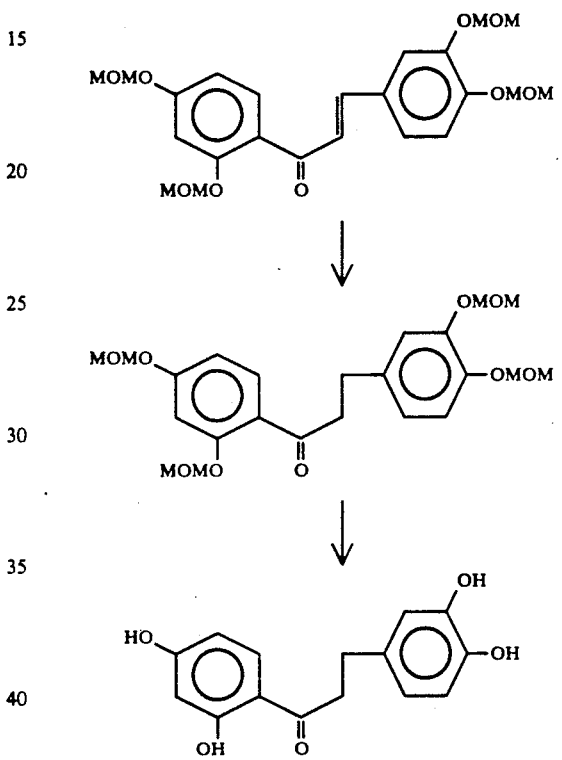

Specific Example 28

To a suspension of 2.57 g of 5% palladium/carbon in 100 ml of ethyl acetate, in which a hydrogen gas had been sufficiently absorbed in advance, 100 ml of an ethyl acetate solution of 5.04 g of the 2'-hydroxy3,4,4',6'-tetrakis(methoxymethoxy)chalcone was added and catalytic reduction was carried out for 2 hours. The reaction liquid was filtered and the solvent was removed from the filtrate by distillation to quantitatively obtain 4.98 g of 1-[2-hydroxy-4,6-bis(methoxymethoxy)phenyl]-3-[3,4-bis(methoxymethoxy)phenyl]-1-propanone.

Infrared absorption spectrum $\nu_{max}^{KBr}$ cm$^{-1}$: 2952, 2828, 1620, 1514, 1432, 1414, 1370, 1316, 1264, 1222, 1190, 1156, 1008, 960.

Proton nuclear magnetic resonance spectrum ($\delta$ ppm in CDCl$_3$): 2.99 (2H, t, J=8.3 Hz), 3.34 (2H, t, J=8.3 Hz), 3.46 (3H, s), 3.48 (3H, s), 3.51 (6H, s), 5.17 (2H, s), 5.20 (2H, s), 5.22 (2H, s), 5.25 (2H, s), 6.27 (2H, s), 6.83 (1H, dd, J=8.3, 2.4 Hz), 7.06 (1H, d, J=2.4 Hz), 7.07 (1H, d, J=8.3 Hz), 13.69 (1H, s).

Mass spectrum:: M/Z (%) 466 (M$^+$, 7), 389 (21), 345 (10), 227 (12), 197 (73), 167 (15), 148 (22), 135 (25), 45 (100).

Then, 4.3 g of 1-[2-hydroxy-4,6-bis(methoxymethoxy)phenyl]-3-[3,4-bis(methoxymethoxy)phenyl]-1-propanone was dissolved in 16 ml of methanol, and 33 ml of a hydrochloric acid/methanol reagent was added to the solution and the mixture was refluxed for 10 minutes. Then, the reaction liquid was poured into ice water and extracted with ethyl acetate, and the ethyl acetate layer was washed with water, dried with anhydrous sodium sulfate and filtered and the solvent was removed from the filtrate by distillation. The obtained residue was subjected to the silica gel column chromatography (160 g of 240–400 mesh silica gel, n-hexane/ethyl acetate=1/1, 0.3 kg/cm²). Fractions of 40 ml were collected and the 28th to 49th fractions were combined, and the solvent was removed by distillation to obtain 933.6 mg (yield=34.9%) of 1-(2,4,6-trihydroxyphenyl)-3-(3,4-dihydroxyphenyl)-1-propanone.

Infrared absorption spectrum $\nu_{max}^{KBr}$ cm$^{-1}$: 3272, 1640, 1610, 1570, 1526, 1476, 1462, 1446, 1390, 1272, 1246, 1204, 1164, 1074, 818.

Proton nuclear magnetic resonance spectrum (δ ppm in CD$_3$OD): 2.81 (2H, t, J =8.3 Hz), 3.32 (2H, t, J =8.3 Hz), 5.83 (2H, s), 6.56 (1H, dd, J =7.8, 2.0 Hz), 6.69 (1H, d, J =2.0 Hz), 6.69 (1H, d, J =7.8 Hz).

Mass spectrum: M/Z (%) 290 (M+, 32), 168 (15), 153 (100), 136 (47), 123 (37), 43 (16) .

The reaction of Specific Example 28 is illustrated below.

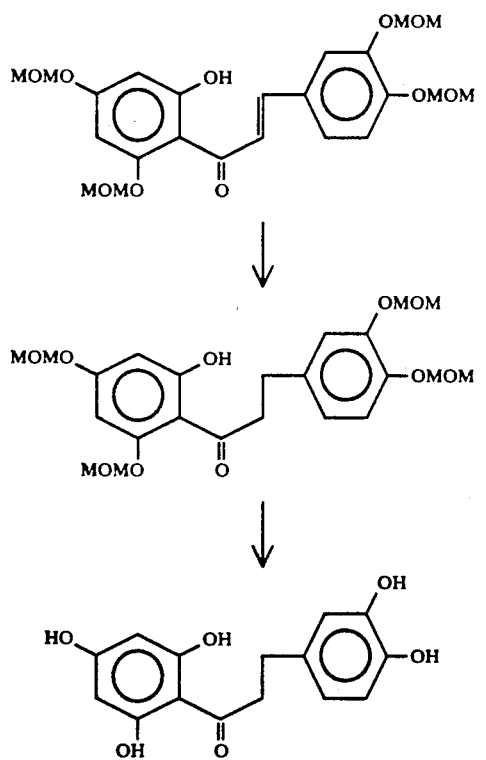

Specific Example 29

A solution of 1.55 g of the 2'-acetoxy-4,4',6'-trihydroxy-3'-(3-methyl-2-butenyl)chalcone obtained in Specific Example 18 in ethanol (30 ml) was added to a suspension of 1.5 g of 5% palladium/carbon in 30 ml of ethanol, in which hydrogen had been sufficiently absorbed in advance, and the mixture was stirred under atmospheric pressure in a hydrogen gas atmosphere for 1 hour. After the reaction, the reaction mixture was filtered and the solvent was removed from the filtrate by distillation. The obtained residue was subjected to the silica gel column chromatography (25 g of 230–400 mesh silica gel, n-hexane/ethyl acetate=3/1, 0.3 kg/cm²). Fractions of 50 ml were collected and the 5th to 9th fractions were combined The solvent was removed by distillation and the obtained residue was recrystallized from a mixed solvent of n-hexane and ethyl acetate to obtain 1.22 g (yield=77.7%) of 1-(2-acetoxy-4,6-dihydroxy-3-isopentylphenyl)-3-(4-hydroxyphenyl)-1-propanone in the form of a colorless prism.

Infrared absorption spectrum $\nu_{max}^{KBr}$ cm$^{-1}$: 3512, 3328, 2948, 2868, 1756, 1632, 1598, 1514, 1474, 1440, 1366, 1296, 1280, 1270, 1240, 1216, 1196, 1152, 1108, 1042, 980, 834, 544.

Protone nuclear magnetic resonance spectrum (δ ppm in acetone-d$_6$): 0.92 (6H, d, J =6.4 Hz), 1.36 (2H, m), 1.58 (1H, m), 2.28 (3H, s), 2.39 (2H, m), 2.90 (2H, t, J =7.6 Hz), 3.18 (2H, t, J =7.6 Hz), 6.34 (1H, s), 6.76 (2H, d, J =8.8 Hz), 7.10 (2H, d, J =8.8 Hz).

Mass spectrum:: M/Z (%) 386 (M+, 23), 344 (26), 343 (18), 327 (11), 326 (11), 287 (26), 224 (11), 223 (71), 197 (11), 196 (65), 190 (11), 182 (11), 181 (39), 165 (14), 163 (13), 139 (33), 120 (36), 107 (57), 44 (100).

The reaction of Specific Example 29 is illustrated below.

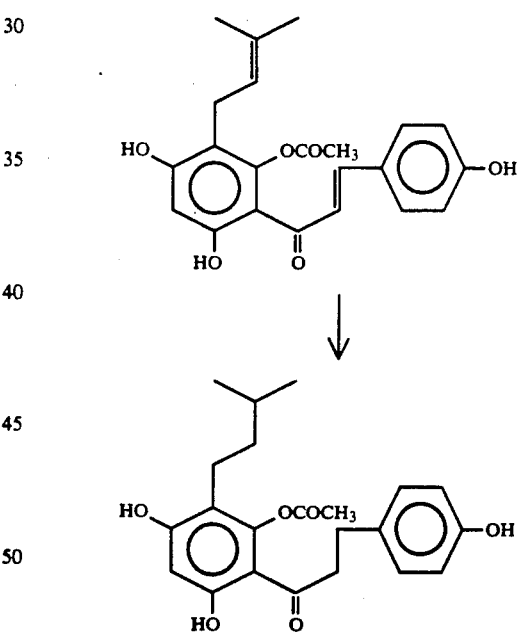

Specific Example 30

In 80 ml of ethanol were dissolved 13.76 g of the 2'-hydroxy-4',6'-dimethoxy-3'-(3-methyl-2-butenyl)acetophenone obtained in Production Example 14 and 7.5 ml of p-anisaldehyde, and the solution was cooled to 0° C. and 120 ml of a saturated ethanol solution of potassium hydroxide was added to the solution. The mixture was stirred for 38 hours. After the reaction, the reaction liquid was diluted with water and neutralized with 6N hydrochloric acid, and the precipitated crystal was recovered by filtration, washed with water, dried and recrystallized from methanol to obtain 16.20 g (yield=81.4%) of 2'-hydroxy-4,4',6'-trimethoxy-3'-(3- methyl-2-butenyl)chalcone in the form of a yellow needle.

Infared red absorption spectrum $\nu_{max}^{KBr}$ cm$^{-1}$: 3124, 2932, 1632, 1608, 1554, 1512, 1470, 1454, 1422, 1376, 1302, 1288, 1226, 1170, 1142, 1114, 1074, 980, 824.

Proton nuclear magnetic resonance spectrum ($\delta$ ppm in acetone-d$_6$): 1.63 (3H, d, J =1.5 Hz), 1.75 (3H, d, J =1.5 Hz), 3.26 (2H, d, J =7.3 Hz), 3.85 (3H, s), 3.95 (3H, s), 4.02 (3H, s), 5.19 (1H, t, septet, J =7.3, 1.5 Hz), 6.27 (1H, s), 6.99 (2H, dd, J =6.8, 2.0 Hz), 7.68 (2H, dd, J =6.8, 2.0 Hz), 7.75 (1H, d, J =15.1 Hz), 7.91 (1H, d, J =15.1 Hz), 14.34 (1H, s).

Mass spectrum:: M/Z (%) 382 (M+, 77), 367 (22), 339 (73), 327 (29), 233 (73), 205 (40), 193 (100), 191 (44), 161 (20), 134 (14), 133 (13), 121 (29), 77 (11), 69 (11), 41 (10).

Then, 13.05 g of the so-obtained 2'-hydroxy4,4',6'-trimethoxy-3'-(3-methyl-2-butenyl)chalcone was catalytically reduced by using 410 ml of ethyl acetate and 4.0 g of 5% palladium/carbon according to customary procedures, and after the reaction was conducted for 3 hours, the reaction liquid mixture was filtered, and the solvent was removed from the filtrate by distillation. The obtained residue was recrystallized from methanol to obtain 12.45 g (yield=94.11%) of 1-(2-hydroxy-4,6-dimethoxy-3-isopentylphenyl)-3-(4-methoxyphenyl)-1-propanone in the form of a light-yellow needle.

Infrared absorption spectrum $\nu_{max}^{KBr}$ cm$^{-1}$: 2948, 2864, 2828, 1614, 1588, 1514, 1470, 1454, 1418, 1384, 1286, 1250, 1226, 1210, 1140, 1094, 1040, 984, 824, 782.

Proton nuclear magnetic resonance spectrum ($\delta$ ppm in acetone-d$_6$): 0.92 (6H, d, J=6.6 Hz), 1.33 (2H, m), 1.54 (1H, nona., J=6.6 Hz), 2.56 (1H, t, J=7.6 Hz), 2.56 (1H, dd, J=9.5, 5.9 Hz), 2.89 (1H, t, J=8.3 Hz), 2.89 (1H, dd, J=8.3, 6.6 Hz), 3.28 (1H, t, J=8.3 Hz), 3.28 (1H, dd, J=8.3, 6.4 Hz), 3.75 (3H, s), 3.93 (3H, s), 3.95 (3H, s), 6.25 (1H, s), 6.84 (2H, dd, J=6.6, 2.2 Hz), 7.18 (2H, dd, J=6.6, 2.2 Hz), 14.03 (1H, s).

Mass spectrum:: M/Z (%) 386 (M+, 46), 329 (54), 251 (73), 224 (83), 167 (46), 121 (100).

The reaction of Specific Example 30 is illustrated below.

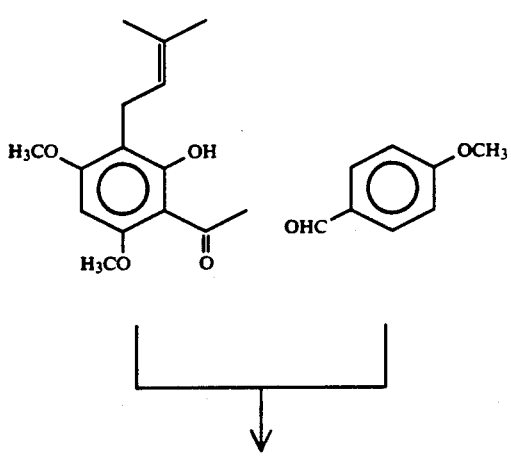

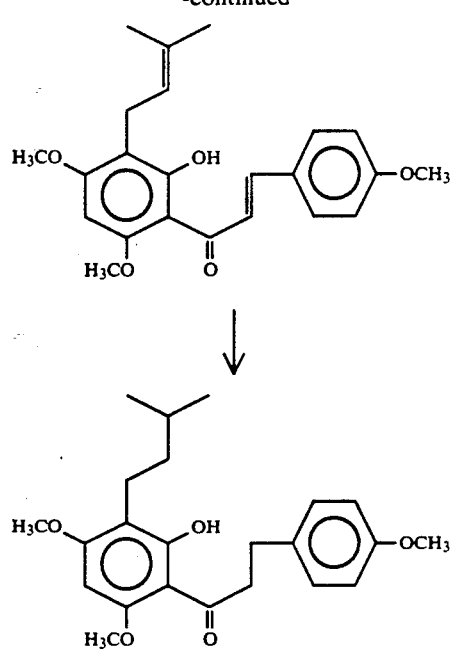

Specific Example 31

In 20 ml of anhydrous acetone was dissolved 2.26 g of the 1-[2-hydroxy-4,6-bis(methoxymethoxy)-3-isopentylphenyl]-3-(4-methoxymethoxyphenyl)-1-propanone obtained as the intermediate in Specific Example 26, and 4.3 g of anhydrous potassium carbonate was added to the solution and the mixture was stirred at room temperature for 20 minutes. Then, 2.18 g of methyl bromoacetate was added to the reaction mixture, and the mixture was stirred at room temperature for 2 hours to effect reaction. After the reaction, the reaction mixture was extracted with 500 ml of ether, washed with water, shaken with a saturated aqueous sodium chloride, dried with anhydrous sodium sulfate and filtered. The solvent was removed from the filtrate by distillation and the obtained residue was subjected to the silica gel column chromatography 28 g of 230 –400 mesh silica gel, solvent=n-hexane/ethyl acetate (5/1), 0.3 kg/cm$^2$. Fractions of 50 ml were collected and the 3rd to 7th fractions were combined to obtain 2.24 g (yield=86.2%) of 1-[2-isopentylphenyl-3-(4-methoxymethoxyphenyl)-1-3-isopentylphenyl]-3-(4-methoxymethoxyphenyl)-1-propanone in the form of a colorless oil.

Infrared absorption spectrum $\nu_{max}^{KBr}$ cm$^{-1}$: 2952, 2824, 1766, 1702, 1600, 1512, 1476, 1440, 1404, 1230, 1206, 1154, 1128, 1078, 1038, 1008.

Proton nuclear magnetic resonance spectrum ($\delta$ ppm in CDCl$_3$): 0.93 (6H, d, J=6.6 Hz), 1.38 (2H, m), 1.61 (1H, m), 2.56 (2H, m), 2.95 (2H, t, J=6.6 Hz), 3.12 (2H, t, J=6.6 Hz), 3.40 (3H, s), 3.46 (3H, s), 3.48 (3H, s), 3.80 (3H, s), 4.43 (2H, s), 5.05 (2H, s), 5.14 (2H, s), 5.18 (2H, s), 6.72 (1H, s), 6.94 (2H, d, J=8.5 Hz), 7.14 (2H, d, J=8.5 Hz).

Mass spectrum:: M/Z (%) 548 (M+, 2), 487 (9), 356 (13), 339 (20), 151 (12), 121 (9), 45 (100).

Then, 1.30 g of 1-[2-methoxycarbonylmethoxy-4,6-bis(methoxymethoxy)-3-isopentylphenyl]-3-(4-methoxymethoxyphenyl)-1-propanone was dissolved in 3 ml of methanol, and 10 ml of a hydrochloric acid/methanol reagent was added to the solution and the mixture was heated and refluxed for 40 minutes. The temperature of the reaction mixture was lowered to room temperature and the reaction mixture was neutralized with a saturated aqueous solution of sodium hydrogencarbonate and extracted with 500 ml of ethyl acetate. The ethyl acetate layer was washed with water, shaken with a saturated aqueous solution of sodium chloride, dried with anhydrous sodium sulfate and filtered. The solvent was removed from the filtrate by distillation. The obtained residue was recrystallized from chloroform to obtain 918 mg (yield=93.0%) of 1-(4,6-dihydroxy-2-methoxycarbonylmethoxy-3-isopentylphenyl)-3-(4-hydroxyphenyl)-1-propanone in the form of a colorless prism.

Infrared absorption spectrum $\nu_{max}^{KBr}$ cm$^{-1}$: 3306, 2952, 1738, 1622, 1514, 1370, 1248, 1220, 1206, 1154, 1118, 1088.

Proton nuclear magnetic resonance spectrum ($\delta$ ppm in CDCl$_3$): 0.93 (6H, d, J=6.4 Hz), 1.47 (2H, m), 1.51 (2H, m), 2.58 (2H, m), 2.88 (2H, t, J=7.0 Hz), 3.40 (2H, t, J=7.0 Hz), 3.71 (3H, s), 4.50 (2H, s), 6.24 (1H, s), 6.73 (2H, d, J=8.5 Hz), 7.07 (2H, d, J=8.5 Hz).

Mass spectrum:: M/Z (%) 416 (M+, 43), 327 (60), 295 (47), 268 (100), 211 (62), 179 (45), 169 (47), 107 (65), 69 (64).

The reaction of Specific Example 31 is illustrated below.

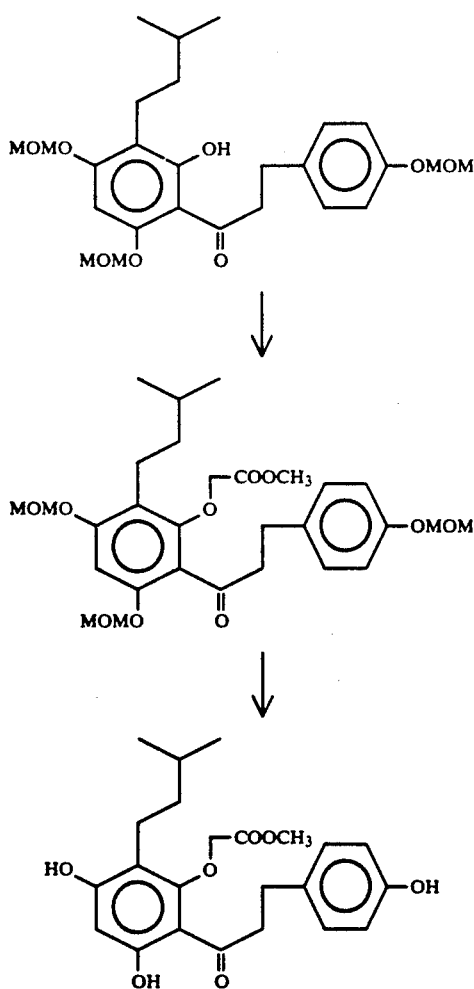

Specific Example 32

In 4 ml of methanol was dissolved 400 mg of the 1-(4,6-dihydroxy-2-methoxycarbonylmethoxy-3-isopentylphenyl)-3-(4-hydroxyphenyl)-1-propanone, and 4 ml of a 5% aqueous solution of potassium hydroxide was added to the solution and the mixture was stirred at room temperature for 10 minutes to effect a reaction. After the reaction, the reaction mixture was made weakly acidic with dilute hydrochloric acid and extracted with 300 ml of ethyl acetate, and the ethyl acetate layer was washed with water (100 ml×4 times), shaken with a saturated aqueous solution of sodium chloride (100 ml×2 times), dried with anhydrous sodium sulfate and filtered. The solvent was removed from the filtrate by distillation and the obtained residue was recrystallized from chloroform to quantitatively obtain 385 mg of 1-(2-carboxymethoxy-4,6-dihydroxy-3-isopentylphenyl)-3-(4-hydroxyphenyl)-1-propanone in the form of a colorless prism.

Infrared absorption spectrum $\nu_{max}^{KBr}$ cm$^{-1}$: 3416, 3260, 2952, 1726, 1620, 1514, 1378, 1366, 1248, 1216, 1152, 1120, 1090, 832.

Proton nuclear magnetic resonance spectrum ($\delta$ ppm in acetone-d$_6$): 0.94 (6H, d, J=5.9 Hz), 1.46 (2H, m), 1.61 (1H, m), 2.61 (2H, m), 2.89 (2H, t, J=7.6 Hz), 3.44 (2H, t, J=7.6 Hz), 4.50 (2H, s), 6.24 (1H, s), 6.72 (2H, d, J=8.5 Hz), 7.08 (2H, d, J=8.5 Hz).

Mass spectrum: M/Z (%) 402 (M+, 22), 327 (45), 281 (21), 254 (36), 239 (18), 223 (22), 197 (51), 179 (36), 165 (16), 120 (26), 107 (75), 44 (100).

The reaction of Specific Sample 32 is illustrated below.

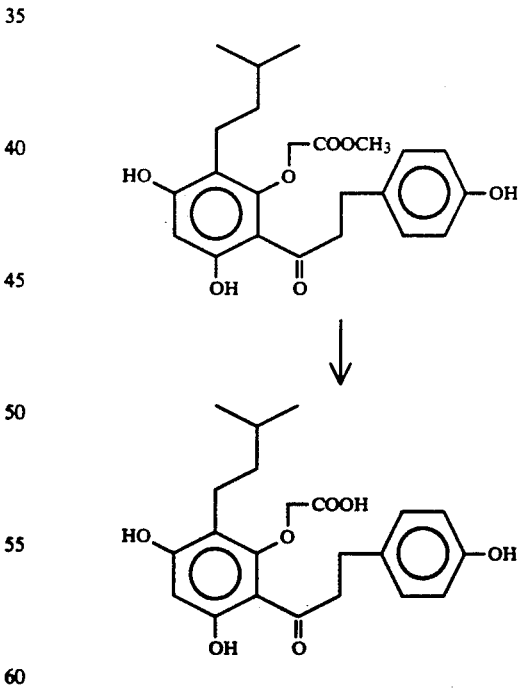

Specific Example 33

To 20 ml of a suspension of 0.31 g of 5% palladium/carbon in ethyl acetate, in which hydrogen had been adsorbed in advance, was added 1.03 g of the 2'-hydroxy-4,4'-dimethoxy-3'-(3-methyl-2-butenyl)chalcone obtained in Specific Example 16, and the mixture was stirred at room temperature for 5 hours and hydrogen was absorbed. After the reaction, the suspension was filtered to remove the palladium/carbon, and the solvent was removed from the filtrate by distillation to obtain 1.03 g (yield 98.7%) of 1-(2-hydroxy-4-methoxy-3-isopentylphenyl)-3-(4-methoxyphenyl)-1-propanone in the form of a white solid.

Infrared absorption spectrum $\nu_{max}^{KBr}$ cm$^{-1}$: 3440, 2948, 2864, 2836, 1624, 1584, 1514, 1498, 1460, 1436, 1418, 1384, 1368, 1344, 1314, 1304, 1274, 1252, 1222, 1190, 1176, 1134, 1098, 1066, 1040, 832, 798, 786, 626.

Proton nuclear magnetic resonance spectrum (δ ppm in CDCl$_3$): 0.94 (6H, d, J=6.4 Hz), 1.36 (2H, m), 1.59 (1H, m), 2.64 (1H, dd, J=6.4, 10.3 Hz), 2.64 (1H, t, J=8.3 Hz), 2.99 (1H, dd, J=6.4, 7.8 Hz), 2.99 (1H, t, J=7.8 Hz), 3.21 (1H, dd, J=6.4, 7.8 Hz), 3.21 (1H, t, J=7.8 Hz), 3.78 (3H, s), 3.87 (3H, s), 6.42 (1H, d, J=8.8 Hz), 6.84 (2H, d, J=8.8 Hz), 7.16 (2H, d, J=8.8 Hz), 7.60 (1H, d, J=8.8 Hz), 12.78 (1H, s).

Mass spectrum:: M/Z (%) 356 (M+21), 300 (10), 221 (38), 179 (10), 134 (37), 121 (100).

The reaction of Specific Example 33 is illustrated below.

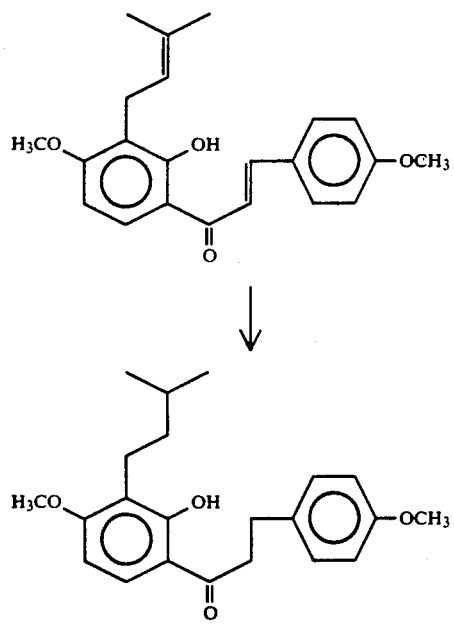

Specific Example 34

To 6.03 g of the 1-(2-hydroxy-4,6-dimethoxy-3-isopentylphenyl)-3-(4-methoxyphenyl)-1-propanone obtained in Specific Example 30 and 12.68 g of anhydrous potassium carbonate was added 60 ml of anhydrous acetone, and the mixture was stirred and 5.7 ml of methyl bromoacetate was gradually added to the mixture. The mixture was stirred for 5 days, poured into ice water and extracted with ether, and the extract was dried with anhydrous sodium sulfate and filtered. The solvent was removed from the filtrate by distillation and the obtained residue was subjected to the silica gel chromatography (310 g of 230-400 mesh silica gel, n-hexane/ethyl acetate =6/1, 0.4 kg/cm$^2$). Fractions of 50 ml were collected and the 29th to 45th fractions were combined to obtain 5.16 g (yield=72.2%) of 1-(4,6-dimethoxy-2-methoxycarbonylmethoxy-3-isopentylphenyl)-3-(4-methoxyphenyl)-1-propanone.

Infrared absorption spectrum $\nu_{max}^{KBr}$ cm$^{-1}$: 2948, 2836, 1758, 1694, 1602, 1514, 1484, 1460, 1444, 1436, 1280, 1244, 1212, 1202, 1140, 1112, 1096, 1036, 836.

Proton nuclear magnetic resonance spectrum (δ ppm in acetone-d$_6$): 0.92 (6H, d, J=6.5 Hz), 1.36 (2H, m), 1.57 (1H, none., J=6.5 Hz), 2.56 (1H, t, J=8.2 Hz), 2.56 (1H, dd, J=11.1, 5.0 Hz), 2.86 (1H, t, J=6.6 Hz), 2.87 (1H, dd, J=9.9, 6.6 Hz), 3.04 (1H, t, J=6.6 Hz), 3.04 (1H, dd, J=9.9, 6.6 Hz), 3.74 (3H, s), 3.75 (3H, s), 3.83 (3H, s), 3.89 (3H, s), 4.40 (2H, s), 6.56 (1H, s), 6.82 (2H, dd, J=6.5, 2.2 Hz), 7.16 (2H, dd, J=6.5, 2.2 Hz).

Mass spectrum:: M/Z (%) 458 (M$^+$, 11), 440 (10), 427 (23), 369 (42), 323 (68), 296 (81), 239 (81), 121 (100).

The reaction of Specific Example 34 is illustrated below.

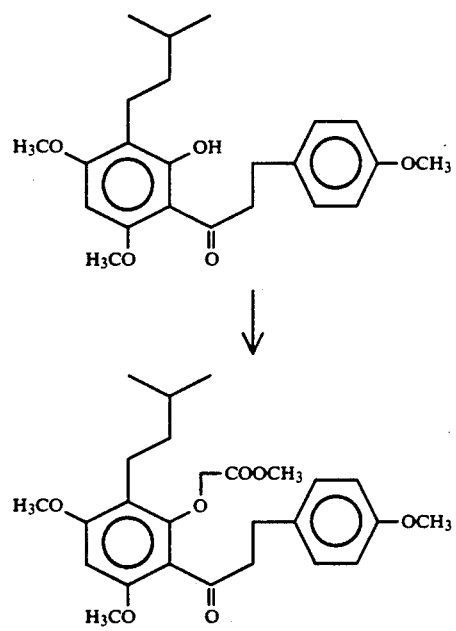

Specific Example 35

In 40 ml of methanol was dissolved 2.05 g of the 1-(4,6-dimethoxy-2-methoxycarbonylmethoxy-3-isopentylphenyl)-3-(4-methoxyphenyl)-1-propanone obtained in Specific Example 34, and 40 ml of a 5% solution of potassium hydroxide was dropped into the solution over a period of 2 minutes. The liquid mixture was neutralized with 3N hydrochloric acid and extracted with ether, and the ether layer was washed with water, dried with anhydrous sodium sulfate and filtered. The solvent was removed from the filtrate by distillation and the obtained residue was recrystallized from a mixed solvent of hexane and ethyl acetate to obtain 1.51 g (yield=75.9%) of 1-(2-carboxymethoxy-4,6-dimethoxy-3-isopentylphenyl)-3-(4-methoxyphenyl)-1-propanone in the form of a colorless grain.

Infrared absorption spectrum $\nu_{max}^{KBr}$ cm$^{-1}$: 3000, 2952, 2840, 2696, 2576, 1742, 1712, 1696, 1600, 1584, 1514, 1462, 1416, 1320, 1250, 1200, 1136, 1098, 828, 808.

Proton nuclear magnetic resonance spectrum (δ ppm in acetone-d$_6$): 0.92 (6H, d, J=6.5 Hz), 1.38 (2H, m), 1.58 (1H, none., J=6.5 Hz), 2.58 (1H, t, J=7.9 Hz), 2.58 (1H, dd, J=11.0, 4.9 Hz), 2.87 (1H, t, J=6.8 Hz), 2.87 (1H, dd, J=10.0, 6.8 Hz), 3.05 (1H, t, J=6.8 Hz), 3.05 (1H, dd, J=10.0, 6.8 Hz), 3.74 (3H, s), 3.83 (3H, s), 3.89

(3H, s), 4.43 (2H, s), 6.56 (1H, s), 6.82 (2H, dd, J=6.6, 2.2 Hz), 7.16 (2H, dd, J=6.6, 2.2 Hz).

Mass spectrum: M/Z (%) 444 (M+, 4), 369 (21), 309 (27), 282 (37), 225 (44), 134 (24), 121 (100), 44 (40).

The reaction of Specific Example 35 is illustrated below.

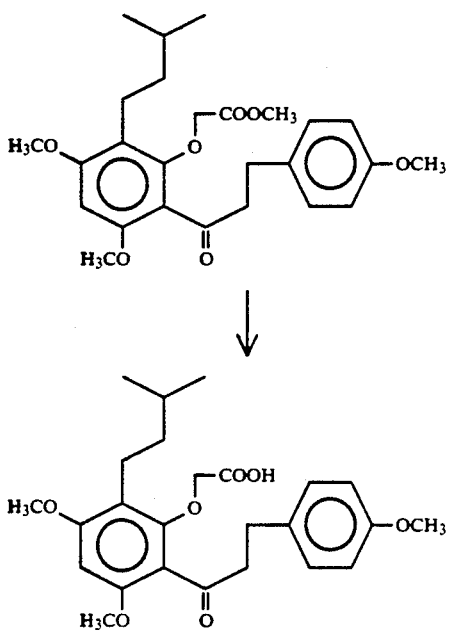

Specific Example 36

In 65 ml of dimethylsulfoxide were dissolved 20.01 g of the 4'-benzyloxy-2'-hydroxy-3'-(3-methyl-2-butenyl-)acetophenone obtained in Production Example 15 and 15.00 g of the 4-benzyloxybenzaldehyde obtained in Production Example 27, and 130 ml of a saturated ethanol solution of potassium hydroxide was added to the solution and the mixture was stirred at room temperature in a nitrogen current for 2.5 hours. After the reaction, the reaction liquid was diluted with water and was gradually made acidic by addition of 3N hydrochloric acid under cooling. The formed precipitate was recovered by filtration and recrystallized from a mixed solvent of benzene and ethanol to obtain 23.64 g (yield =72.7%) of 4,4'-dibenzyloxy-2'-hydroxy-3'-(3-methyl-2-butenyl)chalcone in the form of a yellow needle.

Infrared absorption spectrum $\nu_{max}^{KBr}$ cm$^{-1}$: 3028, 2912, 2852, 1638, 1608, 1566, 1514, 1498, 1450, 1426, 1388, 1376, 1356, 1312, 1292, 1260, 1242, 1182, 1164, 1114, 1080, 1066, 1028, 978, 858, 826, 780.

Proton nuclear magnetic resonance spectrum (δ ppm in CDCl$_3$): 1.67 (3H, s), 1.72 (3H, s), 3.45 (2H, d, J=7.3 Hz), 5.10 (2H, s), 5.17 (2H, s), 5.27 (1H, brt, J=7.3 Hz), 6.51 (1H, d, J=8.8 Hz), 7.00 (2H, d, J=8.8 Hz), 7.29-7.44 (10H, m), 7.44 (1H, d, J=15.1 Hz), 7.58 (2H, d, J=8.8 Hz), 7.74 (1H, d, J=8.8 Hz), 7.83 (1H, d, J=15.1 Hz), 13.47 (1H, s).

Mass spectrum:: M/Z (%) 504 (M+, 10), 414 (6), 413 (17), 203 (27), 92 (8), 91 (100), 65 (6), 44 (9).

Then, 21.03 g of the so-obtained 4,4'-dibenzyloxy2'-hydroxy-3'-(3-methyl-2-butenyl)chalcone was added to 200 ml of an ethyl acetate suspension of 7.01 g of 5% palladium/carbon, in which hydrogen had been adsorbed in advance, and the mixture was stirred at room temperature for 6 hours and hydrogen was absorbed. After the reaction, the suspension was filtered to remove the palladium/carbon, and the solvent was removed from the filtrate by distillation and the obtained residue was recrystallized from benzene to obtain 11.85 g (yield=86.6%) of 1-(2,4-dihydroxy-3-isopentyl-phenyl)-3-(4-hydroxyphenyl)-1-propanone in the form of a colorless needle.

Infrared absorption spectrum $\nu_{max}^{KBr}$ cm$^{-1}$: 3172, 2952, 2864, 1616, 1584, 1514, 1496, 1454, 1366, 1324, 1294, 1260, 1240, 1174, 1152, 1118, 1092, 1028, 890, 854, 826, 792, 760, 666, 642, 618.

Proton nuclear magnetic resonance spectrum (δ ppm in acetone-d$_6$): 0.94 (6H, d, J=6.8 Hz), 1.36-1.47 (2H, m), 1.59 (1H, t, septet, J=6.8 Hz, J=6.8 Hz), 2.66 (1H, dd, J=5.4, 10.3 Hz), 2.66 (1H, t, J=7.8 Hz), 2.92 (2H, t, J=7.3 Hz), 3.24 (2H, t, J=7.3 Hz), 6.47 (1H, d, J=8.8 Hz), 6.75 (2H, d, J=8.8 Hz), 7.12 (2H, d, J=8.8 Hz), 7.68 (1H, d, J=8.8 Hz), 8.48 (1H, brs), 13.47 (1H, s, eliminated by addition of D$_2$O).

Mass spectrum: M/Z (%) 328 (M+, 41), 272 (21), 254 (20), 208 (12), 207 (93), 189 (12), 166 (30), 165 (46), 151 (21), 149 (20), 147 (11), 120 (57), 107 (100).

The reaction of Specific Example 36 is illustrated below.

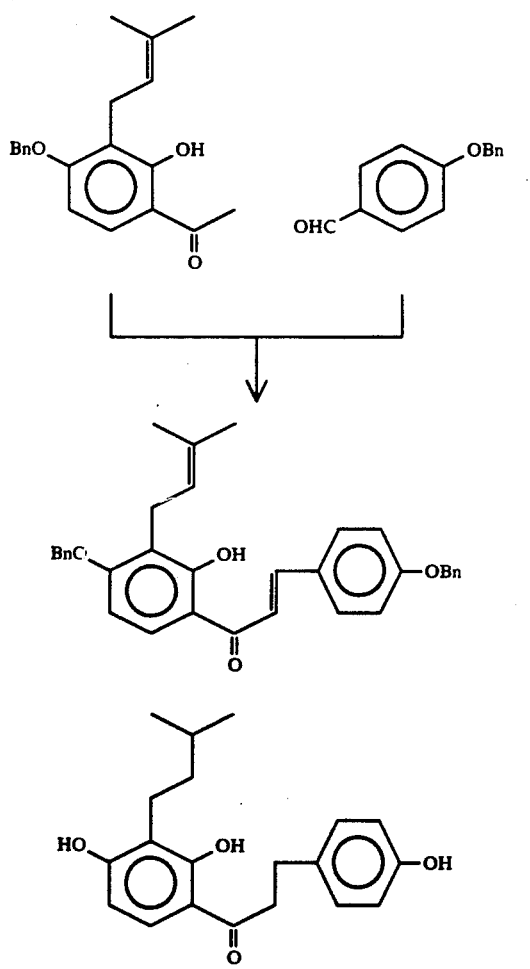

Specific Example 37

In 45 ml of ethanol were dissolved 6.99 g of the 2'-hydroxy-4',6'-bis(methoxymethoxy)-3'-(3-methyl2- butenyl)acetophenone obtained in Production Example 13 and 5.01 of the 4-methoxymethoxy-3-(3-methyl-2-butenyl)benzaldehyde, and the solution was cooled to 0° C. Then, 65 ml of a saturated solution of potassium hydroxide in ethanol was added to the solution and the mixture was stirred at room temperature overnight. The reaction liquid was neutralized with 6N hydrochloric acid and extracted with ethyl acetate, and the ethyl acetate layer was washed with water, dried with anhydrous sodium sulfate and filtered. The solvent was removed from the filtrate by distillation and the residue was recrystallized from n-hexane to obtain 7.22 g (yield=61.7%) of 2'-hydroxy-4,4',6'-tris(methoxymethoxy)-3,3'-bis(3-methyl-2-butenyl)chalcone.

Infrared absorption spectrum $\nu_{max}^{KBr}$ cm$^{-1}$: 2956, 2908, 2852, 1630, 1612, 1590, 1562, 1494, 1426, 1412, 1314, 1244, 1152, 1132, 1110, 1064, 1038, 1006, 988, 972.

Proton nuclear magnetic resonance spectrum ($\delta$ ppm in acetone-d$_6$): 1.64, 1.74, 1.76, 1.77 (each 3H, s), 3.31 (2H, d, J=7.3 Hz), 3.38 (2H, d, J=7.8 Hz), 3.46 (3H, s), 3.47 (3H, s), 3.55 (3H, s), 5.22 (1H, m), 5.31 (2H, s), 5.32 (2H, s), 5.35 (1H, m), 5.40 (2H, s), 7.14 (1H, d, J=9.3 Hz), 7.55–7.50 (2H, m), 7.76 (1H, d, J=15.6 Hz), 7.95 (1H, d, J=15.6 Hz), 14.08 (1H, s).

Mass spectrum:: M/Z (%) 540 (M+, 4), 496 (5), 495 (9), 263 (14), 231 (7), 219 (13), 165 (5), 69 (8), 45 (100).

Then, 80 ml of an ethyl acetate solution of 7.22 g of 2'-hydroxy-4,4',6'-tris(methoxymethoxy)-3,3'-bis(3-methyl-2-butenyl)chalcone was added to a suspension of 1.67 g of 5% palladium/carbon in 50 ml of ethyl acetate, in which a hydrogen gas had been sufficiently absorbed in advance, and the mixture was stirred at room temperature under atmospheric pressure in a hydrogen gas atmosphere for 4 hours. After the reaction, the suspension was filtered and the solvent was removed from the filtrate by distillation to obtain 6.23 g (yield=85.3%) of 1-[2-hydroxy-4,6-bis(methoxymethoxy)-3-isopentylphenyl]-3-(3-isopentyl-4-methoxymethoxyphenyl)-1-propanone in the form of a syrup.

Infrared absorption spectrum $\nu_{max}^{KBr}$ cm$^{-1}$: 3580, 2952, 2864, 2824, 1616, 1500, 1468, 1450, 1424, 1404, 1384, 1366, 1242, 1204, 1202, 1154, 1132, 1064, 1014, 974, 956, 940, 924.

Proton nuclear magnetic resonance spectrum ($\delta$ ppm in acetone-d$_6$): 0.94 (12H, d, J=5.7 Hz), 1.20–1.70 (6H, m), 2.61 (4H, t, J=7.8 Hz), 2.92 (2H, t, J=7.8 Hz), 3.39 (2H, t, J=8.3 Hz), 3.44 (3H, s), 3.47 (3H, s), 3.48 (3H, s), 5.17 (2H, s), 5.29 (2H, s), 5.32 (2H, s), 6.48 (1H, s), 6.96 (1H, d, J=8.3 Hz), 7.01–7.07 (2H, m), 13.90 (1H, s, eliminated by addition of D$_2$O).

Mass spectrum:: M/Z (%) 546 (M+, 2), 267 (9), 252 (3), 207 (7), 196 (3), 195 (3), 165 (3), 164 (5), 151 (3), 135 (3), 58 (3), 46 (3), 45 (100), 43 (10).

Then, 7.00 g of 1-[2-hydroxy-4,6-bis(methoxymethoxy)-3-isopentylphenyl]-3-(3-isopentyl-4-methoxymethoxyphenyl)-1-propanone was dissolved in 17.5 ml of methanol, and 52.0 ml of a hydrochloric acid/methanol reagent was added to the solution and the mixture was refluxed for 30 minutes. The reaction liquid was poured into ice water and extracted with ethyl acetate, and the organic layer was washed with a saturated aqueous solution of sodium hydrogencarbonate, water and a saturated aqueous solution of sodium chloride in sequence and dried with anhydrous sodium sulfate. The solvent was removed by distillation and the obtained residue was recrystallized from chloroform to obtain 3.84 g (yield=72.4%) of 1-(2,4,6-trihydroxy-3-isopentylphenyl)-3-(4-hydroxy-3-isopentylphenyl)-1-propanone.

Infrared absorption spectrum $\nu_{max}^{KBr}$ cm$^{-1}$: 3288, 2952, 2864, 1630, 1574, 1504, 1442, 1384, 1366, 1304, 1280, 1250, 1212, 1144, 1122, 1070, 816.

Proton nuclear magnetic resonance spectrum ($\delta$ ppm in acetone-d$_6$): 0.93 (12H, d, J=6.4 Hz), 1.30–1.70 (6H, m), 2.53–2.63 (4H, m), 2.87 (2H, m), 3.34 (2H, m), 6.06 (1H, s), 6.72 (1H, d, J=7.8 Hz), 6.90 (1H, dd, J=7.8, 2.0 Hz), 7.00 (1H, d, J=2.0 Hz), 7.92 (1H, s), 9.01 (1H, s), 9.49 (1H, s), 13.99 (1H, s).

Mass spectrum: M/Z (%) 414 (M+, 30), 223 (52), 196 (20), 191 (16), 190 (100), 182 (21), 181 (62), 177 (32), 175 (16), 165 (15), 163 (19), 139 (12), 134 (12), 121 (32), 45 (28).

The reaction of Specific Example 37 is illustrated below.

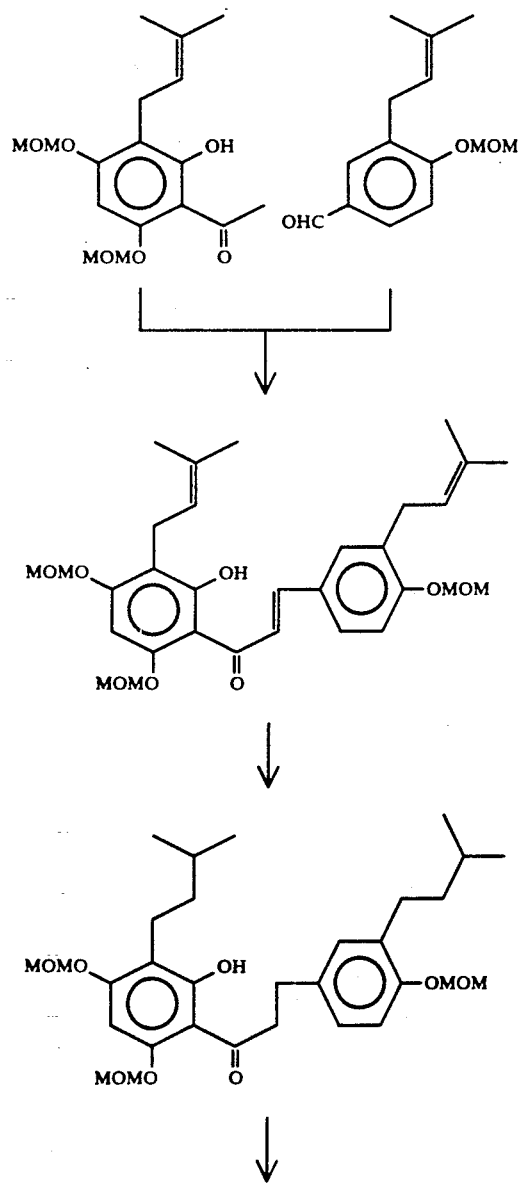

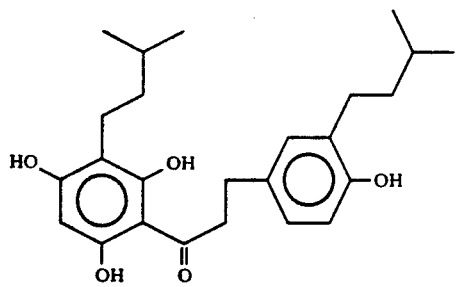

Industrial Applicability

According to the present invention, an anti-ulcer agent having excellent anti-ulcer action and reduced side effects, which can be continuously administered for a long time, and a novel chalcone derivative valuable for use as this anti-ulcer agent are provided.

The anti-ulcer actions of the compounds of formula I obtained in the above-mentioned specific examples will now be described with reference to the following experimental examples.

Experimental Example 1

A suspension of a compound of formula I in a 0.5% solution of CMC (carboxymethyl cellulose) was intraabdominally or orally administered in male rats of the Wister line (each group consisting of 10 rats) having a body weight of 180 to 200 g, which had made to fast for 24 hours, and after 30 minutes, 1 ml of 100% ethanol was orally administered. After 1 hour from the administration of 100% ethanol, the abdominal operation was carried out, and the length of the damaged region on the gastric mucous membrane was measured as the mucous membrane damage coefficient and compared with the value obtained in the control group. Note, a 0.5% solution of CMC not containing a compound of formula I was intraabdominally or orally administered in the control group. Data of the inhibition ratio calculated according to the following formula is shown in Tables 1 through 4:

$$\text{Inhibition ratio (\%)} = \frac{A - B}{A} \times 100$$

wherein A stands for the value obtained in the control group and B stands for the value obtained in the group in which the compound of formula I had been administered.

TABLE 1

| Chemical Tested | Administered Amount (mg/kg) | Administration Course | Mucous Membrane Damage Coefficient (mm) | Inhibition Ratio (%) |
|---|---|---|---|---|
| control | — | i.p. | 102.6 | — |
| compound obtained in Specific Example 3 | 100 | i.p. | 37.6 | 63.4 |
| compound obtained in Specific Example 35 | 35 | i.p. | 33.7 | 67.2 |

TABLE 2

| Chemical Tested | Administered Amount (mg/kg) | Administration Course | Mucous Membrane Damage Coefficient (mm) | Inhibition Ratio (%) |
|---|---|---|---|---|
| control | — | p.o. | 87.7 | — |
| compound obtained in Specific Example 3 | 100 | p.o. | 6.0 | 93.2 |
| compound obtained in Specific Example 35 | 100 | p.o. | 16.5 | 81.2 |

TABLE 3

| Chemical Tested | Administered Amount (mg/kg) | Administration Course | Mucous Membrane Damage Coefficient (mm) | Inhibition Ratio (%) |
|---|---|---|---|---|
| control | — | i.p. | 72.63 | — |
| compound obtained in Specific Example 9 | 100 | i.p. | 5.00 | 93.1 |
| compound obtained in Specific Example 11 | 100 | i.p. | 5.25 | 92.8 |
| compound obtained in Specific Example 12 | 100 | i.p. | 41.25 | 43.2 |
| compound obtained in Specific Example 5 | 100 | i.p. | 52.38 | 27.9 |
| compound obtained in Specific Example 6 | 100 | i.p. | 49.13 | 32.4 |
| compound obtained in Specific Example 7 | 100 | i.p. | 49.00 | 32.5 |
| compound obtained in Specific Example 8 | 100 | i.p. | 15.63 | 78.5 |

TABLE 4

| Chemical Tested | Administered Amount (mg/kg) | Administration Course | Mucous Membrane Damage Coefficient (mm) | Inhibition Ratio (%) |
|---|---|---|---|---|
| control | — | i.p. | 72.3 | — |
| compound obtained in Specific Example 16 | 100 | i.p. | 46.0 | 36.4 |
| compound obtained in Specific Example 23 | 100 | i.p. | 45.8 | 36.7 |
| compound obtained in Specific Example 24 | 100 | i.p. | 55.7 | 23.0 |
| compound obtained in Specific Example 28 | 100 | i.p. | 7.2 | 90.0 |
| compound obtained in Specific | 100 | i.p. | 28.0 | 61.3 |

TABLE 4-continued

| Chemical Tested | Administered Amount (mg/kg) | Administration Course | Mucous Membrane Damage Coefficient (mm) | Inhibition Ratio (%) |
|---|---|---|---|---|
| Example 32 compound obtained in Specific Example 33 | 100 | i.p. | 3.3 | 40.1 |
| compound obtained in Specific Example 37 | 100 | i.p. | 49.8 | 31.1 |

Experimental Example 2

A suspension of a compound of formula I in a 5% solution of CMC (carboxymethyl cellulose) was intraabdominally administered in male rats of the Wister line (each group consisting of 10 rats) having a body weight of 180 to 200 g, which had been made to fast for 24 hours. and after 30 minutes, 1 ml of 0.6N hydrochloric acid was orally administered. After 1 hour from the administration of 0.6N hydrochloric acid, the abdominal operation was carried out, and the length of the damage on the gastric mucous membrane was measured as the mucous membrane damage coefficient and compared with the value obtained in the control group in the control group. Note, a 0.5% solution of CMC was intraabdominally administered. Data of the inhibition ratio calculated according to the following formula is shown in Tables 5 through 7:

$$\text{Inhibition ratio (\%)} = \frac{A - B}{A} \times 100$$

wherein A stands for the value obtained in the control group and B stands for the value obtained in the group in which the compound of formula I had been administered.

TABLE 5

| Chemical Tested | Administered Amount (mg/kg) | Administration Course | Mucous Membrane Damage Coefficient (mm) | Inhibition Ratio (%) |
|---|---|---|---|---|
| control | — | i.p. | 65.8 | — |
| compound obtained in Specific Example 3 | 100 | i.p. | 61.8 | 68.1 |

TABLE 6

| Chemical Tested | Administered Amount (mg/kg) | Administration Course | Mucous Membrane Damage Coefficient (mm) | Inhibition Ratio (%) |
|---|---|---|---|---|
| control | — | i.p. | 106.3 | — |
| compound obtained in Specific Example 9 | 100 | i.p. | 39.6 | 62.3 |
| compound obtained in Specific Example 11 | 100 | i.p. | 36.6 | 65.6 |
| compound obtained in | 100 | i.p. | 76.6 | 27.8 |

TABLE 6-continued

| Chemical Tested | Administered Amount (mg/kg) | Administration Course | Mucous Membrane Damage Coefficient (mm) | Inhibition Ratio (%) |
|---|---|---|---|---|
| Specific Example 12 compound obtained in Specific Example 8 | 100 | i.p. | 62.4 | 41.3 |

TABLE 7

| Chemical Tested | Administered Amount (mg/kg) | Administration Course | Mucous Membrane Damage Coefficient (mm) | Inhibition Ratio (%) |
|---|---|---|---|---|
| control | — | i.p. | 133.8 | — |
| compound obtained in Specific Example 35 | 100 | i.p. | 65.8 | 50.8 |

Experimental Example 3

A suspension of a compound of formula I in a 0.5 % solution of CMC (carboxymethyl cellulose) was intraabdominally or orally administered in male rats of the Wister line (each group consisting of 10 rats) having a body weight of 180 to 200 g, which had been made to fast for 24 hours, and after 30 minutes, 1 ml of a liquid mixture of 150 mM hydrochloric acid and 60% ethanol was orally administered. After 1 hour from the administration of the liquid mixture of 150 mM hydrochloric acid and 60% ethanol, the abdominal operation was carried out, and the length of the damage on the gastric mucous membrane was measured as the mucous membrane damage coefficient and compared with the value obtained in the control group. Note, a 0.5% solution of CMC not containing a compound of formula I was intra-abdominally or orally administered in the control group. Data of the inhibition ratio calculated according to the following formula is shown in Tables 8 through 10:

$$\text{Inhibition ratio (\%)} = \frac{A - B}{A} \times 100$$

wherein A stands for the value obtained in the control group and B stands for the value obtained in the group in which the compound of formula I had been administered.

TABLE 8

| Chemical Tested | Administered Amount (mg/kg) | Administration Course | Mucous Membrane Damage Coefficient (mm) | Inhibition Ratio (%) |
|---|---|---|---|---|
| control | — | p.o. | 119.0 | — |
| compound obtained in Specific Example 22 | 100 | p.o. | 1.4 | 98.8 |
| compound obtained in Specific Example 23 | 100 | p.o. | 67.9 | 43.0 |
| compound obtained in | 100 | p.o. | 15.7 | 86.8 |

TABLE 8-continued

| Chemical Tested | Administered Amount (mg/kg) | Administration Course | Mucous Membrane Damage Coefficient (mm) | Inhibition Ratio (%) |
|---|---|---|---|---|
| Specific Example 28 | | | | |

TABLE 9

| Chemical Tested | Administered Amount (mg/kg) | Administration Course | Mucous Membrane Damage Coefficient (mm) | Inhibition Ratio (%) |
|---|---|---|---|---|
| control | — | p.o. | 84.3 | — |
| compound obtained in Specific Example 15 | 30 | p.o. | 30.0 | 64.4 |
| compound obtained in Specific Example 19 | 30 | p.o. | 10.5 | 87.5 |
| compound obtained in Specific Example 22 | 30 | p.o. | 57.2 | 32.1 |
| compound obtained in Specific Example 27 | 30 | p.o. | 1.5 | 98.2 |

TABLE 10

| Chemical Tested | Administered Amount (mg/kg) | Administration Course | Mucous Membrane Damage Coefficient (mm) | Inhibition Ratio (%) |
|---|---|---|---|---|
| control | — | i.p. | 110.7 | — |
| compound obtained in Specific Example 15 | 30 | i.p. | 49.5 | 55.3 |
| compound obtained in Specific Example 22 | 30 | i.p. | 54.2 | 51.0 |
| compound obtained in Specific Example 27 | 30 | i.p. | 60.0 | 45.8 |

As apparent from the results obtained in Experimental Examples 1 through 3, compounds of the formula I have an excellent anti-ulcer action.

Accordingly, a medicine of the present invention comprising a compound of the formula I as the effective ingredient is an excellent anti-ulcer agent.

When compounds of the formula I were orally administered in amounts of 1 g/kg to male mice of the ddY line, none of the mice died.

Accordingly, compounds of the formula I have a low toxicity and a very high safety factor.

The doses and formulations of compounds of the formula I will now be described.

The compound of formula I, which is the effective ingredient of the medicine of the present invention, can be administered to animals and men directly or together with a customary pharmaceutical carrier. The administration mode is not particularly limited and an appropriate administration mode can be freely selected. For example, there can be mentioned oral drugs such as tablets, capsules, granules, fine granules and powders, and non-oral drugs such as injections and suppositories.

For the oral drug to exert an intended effect, preferably the drug is administered at a dose of 100 to 450 mg as the compound of formula I for an adult, several times per day, although the preferred dose differs according to the age, body weight, and disease conditions of a patient.

In the present invention, oral drugs such as tablets, capsules and granules are prepared according to customary procedures by using excipients such as starch, lactose, refined sugar, mannitol, carboxymethyl cellulose, corn starch and inorganic salts.

For these oral drugs, in addition to these excipients, there can be used binders, disintegrating agents, surface active agents, lubricants, flowability improvers, taste improvers, colorants, perfumes and the like according to need. Specific examples of these agents are described below.

Binders

Starch, dextrin, gum arabic powder, gelatin, hydroxypropyl starch, methyl cellulose, sodium carboxymethyl cellulose, hydroxypropyl cellulose, crystalline cellulose, ethyl cellulose, polyvinyl pyrrolidone and Macrogol.

Disintegrating Agents

Starch, hydroxypropyl starch, sodium carboxymethyl cellulose, calcium carboxymethyl cellulose, carboxymethyl cellulose and lowly substituted hydroxypropyl cellulose.

Surface Active Agents

Sodium lauryl sulfate, soybean lecithin, sucrose fatty acid ester and polysorbate 80.

Lubricants

Talc, waxes, hydrogenated vegetable oils, sucrose fatty acid ester, magnesium stearate, calcium stearate, aluminum stearate and polyethylene glycol.

Flowability Improvers

Light anhydrous silicic acid, dry aluminum hydroxide gel, synthetic aluminum silicate and magnesium silicate.

Furthermore, the compound of formula I can be administered in the form of suspensions, emulsions, syrups, and elixirs. These formulations may contain a taste improver, a smell improver, a colorant and the like.

For the non-oral drug to exert an intended effect, preferably the non-oral drug is administered in an amount of 2 to 30 mg per day as the compound of formula I for an adult, by intravenous injection, intravenous dripping, hypodermic injection and intramuscular injection, although the preferred administration amount differs according to the age, body weight, and disease conditions of a patient.

Non-oral drugs are prepared according to customary procedures. As the diluent, there can be used distilled water for injection, physiological saline solution, an aqueous solution of glucose, a vegetable oil for injection, sesame oil, peanut oil, soybean oil, corn oil, propylene glycol and polyethylene glycol. Furthermore, a fungicide, an anti-septic agent and a stabilizer may be incorporated according to need. From the viewpoint of the stability of the non-oral drug, a method can be adopted in which the non-oral drug is filled in a vial and frozen, water is removed by an ordinary freeze-drying technique, and just before administration, a liquid preparation is formed from the freeze-dried product. An isotonic agent, a stabilizer, an anti-septic agent, an analgesic agent and the like may be incorporated according to need.

As other non-oral drugs, there can be mentioned cendermic liniments such as lotions and ointments, and suppositories for intrarectal administration.

The present invention will now be described in detail with reference to the following examples that by no means limit the scope of the invention.

Example 1

In 150 ml of polysorbate 80 was dissolved 7.5 g of the compound obtained in Specific Example 3, and 4.85 l of sterilized physiological saline solution heated at 60° C. was added to the solution and the mixture was sufficiently shaken and sterilely distributed into vials so that 1.5 mg of the compound obtained in Specific Example 3 was contained in each vial. The vials were sealed to obtain an injection unit.

This injection unit was shaken at the time of application and was intravenously injected in an amount of 2 to 20 ml per day according to the disease condition.

Example 2

To a mixture of 5 g of the compound obtained in Specific Example 11 and 10 g of anhydrous silicic acid was added 85 g of corn starch, and the mixture was blended. Then, 50 ml of a 10% ethanol solution of hydroxypropyl cellulose was added to the mixture, and the mixture was kneaded, extruded from an extruder, dried, and sieved according to customary procedures, to obtain a granule having a particle size of 20 to 50 mesh.

The granule was orally administered at a dose of 1 to 2.5 g (50 to 150 mg of the compound obtained in Specific Example 11) three times per day.

Example 3

To a mixture of 42 g of the compound obtained in Specific Example 8 and 20 g of anhydrous silicic acid were added 10 g of microcrystalline cellulose, 3.0 g of magnesium stearate and 65 g of lactose, and the mixture was formed into tablets having a diameter of 7 mm and a weight of 100 mg, by a single-shot tableting machine.

Each of the so-formed tablets contained 30 mg of the compound obtained in Specific Example 8. The tablets were orally administered at a dose of 1 to 5 tablets three times per day.

Example 4

To a mixture of 30 mg of the compound obtained in Specific Example 12 and 150 mg of anhydrous silicic acid was added 70 mg of lactose, and the mixture was blended and filled in capsules of gelatin No. 2 to obtain capsules.

The capsules were orally administered at a dose of 1 to 5 capsules up to three times per day, according to the disease conditions.

Example 5

In 150 ml of polysorbate 80 was dissolved 7.5 g of the compound obtained in Specific Example 6, and 4.85 l of sterilized physiological saline solution heated at 60° C. was added to the solution. The mixture was thoroughly shaken and sterilely distributed into vials so that 1.5 mg of the compound obtained in Specific Example 6 was contained in each vial. The vials were sealed to obtain an injection unit.

The injection unit was shaken at the time of application and intravenously injected in an amount of 2 to 20 ml per day, according to the disease conditions.

Example 6

To a mixture of 5 g of the compound obtained in Specific Example 12 and 10 g of anhydrous silicic acid was added 85 g of corn starch, and the mixture was blended. Then, 50 ml of a 10% ethanol solution of hydroxypropyl cellulose was added to the mixture, and the mixture was kneaded, extruded from an extruder, dried and sieved according to customary procedures to obtain a granule having a particle size of 20 to 50 mesh.

The granule was orally administered at a dose of 1 to 2.5 g (50 to 150 mg of the compound obtained in Specific Example 12) three times per day.

Example 7

To a mixture of 42 g of the compound obtained in Specific Example 5 and 20 g of anhydrous silicic acid were added 10 g of microcrystalline cellulose, 3.0 g of magnesium stearate and 65 g of lactose, and the mixture was formed into tablets having a diameter of 7 mm and a weight of 100 mg, by a single-shot tableting machine.

Each of the obtained tablets contained 30 mg of the compound obtained in Specific Example 5. The tablets were orally administered at a dose of 1 to 5 tablets three times per day.

Example 8

To a mixture of 30 mg of the compound obtained in Specific Example 9 and 150 mg of anhydrous silicic acid was added 70 mg of lactose, and the mixture was filled in capsules of gelatin No. 2 to obtain capsules.

The capsules were orally administered at a dose of 1 to 5 capsules up to three times per day according to the disease conditions.

Example 9

| | | |
|---|---|---|
| (1) | Corn starch | 39 g |
| (2) | Crystalline cellulose | 30 g |
| (3) | Calcium carboxymethyl cellulose | 5 g |
| (4) | Soft anhydrous silicic acid | 0.5 g |
| (5) | Magnesium stearate | 0.5 g |
| (6) | Compound obtained in Specific Example 15 | 25 g |
| | Total | 100 g |

According to the above-mentioned recipe, the components (1) through (6) were homogeneously blended, and the mixture was compression-molded by a tableting machine to obtain tablets, each having a weight of 200 mg.

Each of the so-obtained tablets contained 50 mg of the compound obtained in Example 15, and 2 to 9 tablets were orally administered to an adult several times per day.

Example 10

| | | |
|---|---|---|
| (1) | Crystalline cellulose | 69 g |
| (2) | Magnesium stearate | 1 g |
| (3) | Calcium carboxymethyl cellulose | 5 g |
| (4) | Compound obtained in Specific Example 19 | 25 g |
| | Total | 100 g |

According to the above-mentioned recipe, the components (1) and (4) and a part of the component (2) were homogeneously blended, compression-molded and pulverized, and the component (3) and the remainder of the component (2) were added to the pulverization product and the mixture was compression-molded into tablets, each having a weight of 200 mg.

Each of the so-obtained tablets contained 50 mg of the compound obtained in Specific Example 19.

Example 11

| (1) | Crystalline cellulose | 44.5 g |
|---|---|---|
| (2) | 10% Ethanol solution of hydroxypropyl cellulose | 25 g |
| (3) | Calcium carboxymethyl cellulose | 5 g |
| (4) | Magnesium stearate | 0.5 g |
| (5) | Compound obtained in Specific Example 22 | 25 g |
| | Total | 100 g |

According to the above-mentioned recipe, the components (1), (2) and (5) were homogeneously blended, and the mixture was kneaded, granulated by an extruding granulator, dried and disintegrated. The disintegration product was mixed with the components (3) and (4) and the mixture was compression-molded by a tableting machine to obtain tablets, each having a weight of 200 mg.

Each of the so-obtained tablets contained 50 mg of the compound obtained in Specific Example 22, and the tablets were orally administered to an adult at a dosage of 2 to 9 tablets, several times a day.

Example 12

| (1) | Crystalline cellulose | 85 g |
|---|---|---|
| (2) | 10% Ethanol solution of hydroxypropyl cellulose | 5 g |
| (3) | Compound obtained in Specific Example 27 | 10 g |
| | Total | 100 g |

According to the above-mentioned recipe, the components (1) through (3) were homogeneously blended, kneaded, granulated by an extruding granulator, dried and sieved to obtain a granule.

The obtained granule contained 100 mg of the compound obtained in Specific Example 27 per gram of the granule. The granule was orally administered to an adult at a dosage of 1 to 4.5 g several times a day.

Example 13

| (1) | Corn starch | 74.5 g |
|---|---|---|
| (2) | Light anhydrous silicic acid | 0.5 g |
| (3) | Compound obtained in Specific Example 28 | 25 g |
| | Total | 100 g |

According to the above-mentioned recipe, the components (1) through (3) were homogeneously mixed and distributed in capsules No. 2 so that 200 mg of the mixture was contained in each capsule.

Each capsule contained 50 mg of the compound obtained in Specific Example 28. The capsules were orally administered to an adult at a dosage of 2 to 9 capsules, several times a day.

Example 14

| (1) | Distilled water for injection | appropriate amount |
|---|---|---|
| (2) | Glucose | 200 mg |
| (3) | Compound obtained in Specific Example 35 | 5 mg |
| | | 5 ml |

The components (2) and (3) were dissolved in distilled water for injection, and the solution was poured in a 5-ml ampoule and sterilized under pressure at 121° C. for 15 minutes to obtain an injection unit.

We claim:

1. A compound represented by the following formula

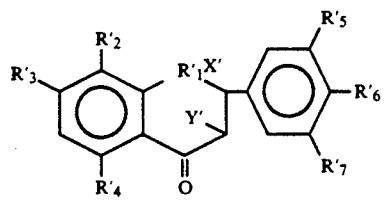

wherein X' and Y' independently represent a hydrogen atom or together form a single bond, $R'_1$ represents a hydroxyl group or a carboxymethoxy group, $R'_2$ represents an isoprenyl group, an isopentyl group or a propyl group, $R'_3$ represents a hydroxyl group or a methoxy group, $R'_4$ represents a hydrogen atom, a hydroxyl group or a methoxy group, $R'_5$ represents a hydrogen atom, a hydroxyl group, a methoxy group or an isopentyl group, $R'_6$ represents a hydroxyl group, a methoxy group or a carboxymethoxy group, and $R'_7$ represents for a hydrogen atom or a methoxy group, provided that (1) when $R'_2$ is a hydrogen atom, at least one of $R'_3$, $R'_4$, $R'_5$ and $R'_6$ is not a methoxy group, (2) when $R'_2$ is an isoprenyl group, $R'_1$ a carboxymethoxy group, (3) when $R'_2$ is an isopentyl group and each of $R'_5$ and $R'_7$ is a hydrogen atom, $R'_4$ is a hydrogen atom and one of $R'_1$ and $R'_6$ is a carboxymethoxy group, (4) when $R'_4$ is not a hydrogen atom, $R'_3$ and $R'_4$ commonly represent a hydroxyl group or a methoxy group, (5) when $R'_5$ is a hydroxyl group, $R'_6$ is a methoxy group, $R'_6$ is a hydroxyl group, (6) when $R'_5$ is a methoxy group, $R'_6$ is a hydroxy group and (7) when $R'_6$ is a carboxymethoxy group, $R'_1$ is a hydroxyl group.

2. A method for treating ulcers in a mammalian organism, said method comprising administering an ulcer treating effective amount of a compound of the formula I':

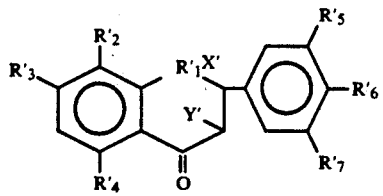

wherein X' and Y' independently represent a hydrogen atom or together form a single bond, $R'_1$ represents a hydroxyl group or a carboxymethoxy group, $R'_2$ represents a hydrogen atom, an isoprenyl group, an isopentyl group or a propyl group, $R'_3$ represents a hydroxyl group or a methoxy group, $R'_4$ represents a hydrogen atom, a hydroxyl group or a methoxy group, $R'_5$ represents a hydrogen atom, a hydroxyl group, a methoxy group or an isopentyl group, $R'_6$ represents a hydroxyl group, a methoxy group or a carboxymethoxy group, and $R'_7$ represents a hydrogen atom or a methoxy group, provided that (1) when $R'_2$ is a hydrogen atom, at least one of $R'_3$, $R'_4$, $R'_5$ and $R'_6$ is not a methoxy group, (2) when $R'_2$ is an isoprenyl group, $R'_1$ is a carboxymethoxy group, (3) when $R'_2$ is an isopentyl group and each of $R'_5$ and $R'_7$ is a hydrogen atom, $R'_4$ is a hydrogen atom and one of $R'_1$ and $R'_6$ is a carboxymethoxy group, (4) when $R'_4$ is not a hydrogen atom, $R'_3$ and $R'_4$ commonly represents a hydroxyl group or a methoxy group, (5) when $R'_5$ is a hydroxyl group, $R'_6$ is a methoxy group, $R'_6$ is a hydroxyl group, (6) when $R'_5$ is a methoxy group, $R'_6$ is a hydroxy group and (7) when $R'_6$ is a carboxymethoxy group, $R'_1$ is a hydroxyl group, to an organism in need of such treatment.

3. A compound as set forth in claim 1 which is selected from the group consisting of 1-(2,4,6-trihydroxy-3-isopentylphenyl)-3-(4-hydroxy-3-methoxyphenyl)-1-propanone, 1-(2,4,6-trihydroxy-3-isopentylphenyl)-3-(4-hydroxy-3,5-dimethoxyphenyl)-1-propanone, 1-(2-carboxymethoxy-4-methoxy-3-isopentylphenyl)-3-(4-methoxyphenyl)-1-propanone, 1-(2-hydroxy-4-methoxy-3-isopentylphenyl)-3-(4-carboxymethoxyphenyl)-1-propanone, 1-(2-carboxymethoxy-4,6-dimethoxy-3-isopentylphenyl)-3-(4-hydroxy-3-methoxyphenyl)-1-propanone, 1-(2-carboxy-methoxy-4,6-dimethoxy-3-isopentylphenyl)-3-(3-hydroxy-4-methoxyphenyl)-1-propanone, 1-(2-carboxymethoxy-4,6-dimethoxy-3-isopentylphenyl)-3-(4-hydroxy-3,5-dimethoxyphenyl)-1-propanone, 2'-carboxymethoxy-4,4'-dimethoxy-3'-(3-methyl-2-butenyl)chalcone, 2'-carboxymethoxy-4,4',6'-trimethoxy-3'-isopentylchalcone, 3-(4-hydroxyphenyl)-1-(2,4,6-trihydroxy-3-n-propylphenyl)-1-propanone, 1-[2-carboxymethoxy4,6-dimethoxy-3-(3-methyl-2-butenyl)phenyl]-3-(4-methoxyphenyl)-1-propanone, and 2'-carboxymethoxy-4,4',6'-trimethoxy-3'-(3-methyl-2-butenyl)chalcone.

4. A compound as set forth in claim 3, which is selected from the group consisting of 1-(2-carboxymethoxy-3-isopentyl-4-methoxyphenyl)-3-(4-methoxyphenyl)-1-propanone, 2'-carboxymethoxy-4,4'-dimethoxy-3'-(3-methyl-2-butenyl)chalcone, 2'-carboxymethoxy-4,4',6'-trimethoxy-3-isopentylchalcone, and 2'-carboxymethoxy-4,4',6'-trimethoxy-3'-(3-methyl-2-butenyl)chalcone.

5. The method according to claim 2, wherein said compound is selected from the group consisting of 1-(2,4,6-trihydroxy-3-isopentylphenyl)-3-(4-hydroxy-3-methoxyphenyl)-1-propanone, 1-(2,4,6,-trihydroxy-3-isopentylphenyl)-3-(4-hydroxy-3,5-dimethoxyphenyl)-1-propanone, 1-(2-carboxymethoxy-4-methoxy-3-isopentylphenyl)-3-(4-methoxyphenyl)-1-propanone, 1-(2-hydroxy-4-methoxy-3-isopentylphenyl)-3-(4-carboxymethoxyphenyl)-1-propanone, 1-(2-carboxymethoxy-4,6-dimethoxy-3-isopentylphenyl)-3-(4-hydroxy-3-methoxyphenyl)-1-propanone, 1-(2-carboxymethoxy-4,6-dimethoxy-3-isopentylphenyl)-3-(3-hydroxy-4-methoxyphenyl)-1-propanone, 1-(2-carboxymethoxy-4,6-dimethoxy-3-isopentylphenyl)-3-(4-hydroxy-3,5-dimethoxyphenyl)-1-propanone, 2'-carboxymethoxy-4,4'-dimethoxy-3'-(3-methyl-2-butenyl)chalcone, 2'-carboxymethoxy-4,4',6'-trimethoxy-3'-isopentylchalcone, 3-(4-hydroxyphenyl)-1-(2,4,6-trihydroxy-3-n-propylphenyl)-1-propanone, 1-[2-carboxymethoxy-4,6-dimethoxy-3-(3-methyl-2-butenyl)phenyl]-3-(4-methoxyphenyl)-1propanone, and 2'-carboxymethoxy-4,4',6'-trimethoxy-3'-(3-methyl-2-butenyl)chalcone.

6. The method according to claim 5, wherein said compound is selected from the group consisting of 1-(2-carboxymethoxy-3-isopentyl-4-methoxyphenyl)-3-(4-methoxyphenyl)-1-propanone, 2'-carboxymethoxy-4,4'-dimethoxy-3'-(3-methyl-2-butenyl)chalcone, 2'-carboxymethoxy-4,4',6'-trimethoxy-3-isopentylchalcone, and 2'-carboxymethoxy-4,4',6'-trimethoxy-3'-(3-methyl-2-butenyl)chalcone.

* * * * *